US011530450B2

(12) United States Patent
Chen et al.

(10) Patent No.: US 11,530,450 B2
(45) Date of Patent: *Dec. 20, 2022

(54) METHODS, COMPOSITIONS, AND KITS FOR DETECTING ALLELIC VARIANTS

(71) Applicant: LIFE TECHNOLOGIES CORPORATION, Carlsbad, CA (US)

(72) Inventors: Caifu Chen, Palo Alto, CA (US); Ruoying Tan, Palo Alto, CA (US)

(*) Notice: Subject to any disclaimer, the term of this patent is extended or adjusted under 35 U.S.C. 154(b) by 177 days.

This patent is subject to a terminal disclaimer.

(21) Appl. No.: 16/745,296

(22) Filed: Jan. 16, 2020

(65) Prior Publication Data

US 2020/0255907 A1    Aug. 13, 2020

Related U.S. Application Data

(60) Continuation of application No. 15/923,954, filed on Mar. 16, 2018, now Pat. No. 10,570,459, which is a division of application No. 14/879,156, filed on Oct. 9, 2015, now abandoned, which is a division of application No. 12/641,321, filed on Dec. 17, 2009, now Pat. No. 9,534,255.

(60) Provisional application No. 61/258,582, filed on Nov. 5, 2009, provisional application No. 61/253,501, filed on Oct. 20, 2009, provisional application No. 61/251,623, filed on Oct. 14, 2009, provisional application No. 61/186,775, filed on Jun. 12, 2009, provisional application No. 61/164,230, filed on Mar. 27, 2009, provisional application No. 61/138,521, filed on Dec. 17, 2008.

(51) Int. Cl.
*C12Q 1/6886* (2018.01)
*C12Q 1/6858* (2018.01)
*C07H 21/04* (2006.01)

(52) U.S. Cl.
CPC ......... *C12Q 1/6886* (2013.01); *C12Q 1/6858* (2013.01); *C07H 21/04* (2013.01); *C12Q 2600/156* (2013.01); *C12Q 2600/172* (2013.01)

(58) Field of Classification Search
CPC ............... C12Q 1/6858; C12Q 1/6886; C12Q 2600/156; C12Q 2600/172; C12Q 2525/107; C12Q 2525/113; C12Q 2525/117; C12Q 2535/125; C12Q 2535/131; C07H 21/04
See application file for complete search history.

(56) References Cited

U.S. PATENT DOCUMENTS

| 5,419,966 A | 5/1995 | Reed et al. |
|---|---|---|
| 5,512,441 A | 4/1996 | Ronai |
| 5,512,677 A | 4/1996 | Chern et al. |
| 5,538,848 A | 7/1996 | Livak et al. |
| 5,585,481 A | 12/1996 | Arnold, Jr. et al. |
| 5,696,251 A | 12/1997 | Arnold, Jr. et al. |
| 5,736,626 A | 4/1998 | Mullah et al. |
| 5,801,155 A | 9/1998 | Kutyavin et al. |
| 5,891,625 A | 4/1999 | Buchardt et al. |
| 5,925,517 A | 7/1999 | Tyagi et al. |
| 5,928,907 A | 7/1999 | Woudenberg et al. |
| 5,942,610 A | 8/1999 | Nelson et al. |
| 5,972,601 A | 10/1999 | Newman |
| 5,972,610 A | 10/1999 | Buchardt et al. |
| 6,015,674 A | 1/2000 | Woudenberg et al. |
| 6,027,889 A | 2/2000 | Barany et al. |
| 6,030,813 A | 2/2000 | Ellis et al. |
| 6,084,102 A | 7/2000 | Kutyavin et al. |
| 6,103,476 A | 8/2000 | Tyagi et al. |
| 6,150,097 A | 11/2000 | Tyagi et al. |
| 6,174,670 B1 | 1/2001 | Wittwer et al. |
| 6,245,533 B1 | 6/2001 | Goldstein et al. |
| 6,303,305 B1 | 10/2001 | Wittwer et al. |
| 6,355,421 B1 | 3/2002 | Coull et al. |
| 6,383,752 B1 | 5/2002 | Agrawal et al. |
| 6,391,592 B1 | 5/2002 | Su et al. |

(Continued)

FOREIGN PATENT DOCUMENTS

| EP | 1905842 A1 | 4/2008 |
|---|---|---|
| EP | 2376659 B1 | 12/2015 |
| EP | 2411543 B1 | 4/2017 |
| EP | 3249053 A1 | 11/2017 |
| JP | 2004511215 A | 4/2004 |
| JP | 2005511096 A | 4/2005 |
| JP | 2006508662 A | 3/2006 |
| WO | WO-9014353 A1 | 11/1990 |

(Continued)

OTHER PUBLICATIONS

Afonina, Irina et al., "Sequence-specific arrest of primer extension on single-stranded DNA by an oligonucleotide-minor groove binder conjugate", Proceedings of the National Academy of Sciences, vol. 93, Biochemistry, USA, Apr. 1996; pp. 3199-3204.

(Continued)

*Primary Examiner* — David C Thomas
(74) *Attorney, Agent, or Firm* — Workman Nydegger; Logan Christenson; John Guynn

(57) ABSTRACT

In some embodiments, the present inventions relates generally to compositions, methods and kits for use in discriminating sequence variation between different alleles. More specifically, in some embodiments, the present invention provides for compositions, methods and kits for quantitating rare (e.g., mutant) allelic variants, such as SNPs, or nucleotide (NT) insertions or deletions, in samples comprising abundant (e.g., wild type) allelic variants with high specificity and selectivity. In particular, in some embodiments, the invention relates to a highly selective method for mutation detection referred to as competitive allele-specific TaqMan PCR ("cast-PCR").

21 Claims, 18 Drawing Sheets

Specification includes a Sequence Listing.

(56) References Cited

U.S. PATENT DOCUMENTS

| | | | |
|---|---|---|---|
| 6,485,901 | B1 | 11/2002 | Gildea et al. |
| 6,492,346 | B1 | 12/2002 | Hedgpeth et al. |
| 6,503,720 | B2 | 1/2003 | Wittwer et al. |
| 6,548,250 | B1 | 4/2003 | Sorge |
| 6,589,250 | B2 | 7/2003 | Schendel |
| 6,589,743 | B2 | 7/2003 | Sorge |
| 6,590,091 | B2 | 7/2003 | Albagli et al. |
| 6,593,091 | B2 | 7/2003 | Keys et al. |
| 6,596,490 | B2 | 7/2003 | Dattagupta |
| 6,605,451 | B1 | 8/2003 | Marmaro et al. |
| 6,727,356 | B1 | 4/2004 | Reed et al. |
| 6,783,934 | B1 | 8/2004 | McMillan et al. |
| 6,814,934 | B1 | 11/2004 | Higuchi |
| 6,818,420 | B2 | 11/2004 | Chou et al. |
| 6,852,487 | B1 | 2/2005 | Barany et al. |
| 7,160,997 | B2 | 1/2007 | Chou et al. |
| 7,228,237 | B2 | 6/2007 | Woo et al. |
| 7,556,923 | B1 | 7/2009 | Hedgpeth et al. |
| 9,512,473 | B2 | 12/2016 | Chen et al. |
| 9,534,255 | B2 | 1/2017 | Chen et al. |
| 10,081,833 | B2 | 9/2018 | Chen et al. |
| 10,570,459 | B2 * | 2/2020 | Chen .................. C12Q 1/6858 |
| 10,689,694 | B2 * | 6/2020 | Chen .................. C12Q 1/6883 |
| 2002/0076767 | A1 | 6/2002 | Su et al. |
| 2003/0082549 | A1 | 5/2003 | Liu |
| 2003/0082600 | A1 | 5/2003 | Olek et al. |
| 2004/0096819 | A1 | 5/2004 | McMillan et al. |
| 2005/0118623 | A1 | 6/2005 | Belousov et al. |
| 2005/0287553 | A1 | 12/2005 | Guetig et al. |
| 2007/0087360 | A1 | 4/2007 | Boyd |
| 2007/0184457 | A1 | 8/2007 | Pont-Kingdon et al. |
| 2008/0090239 | A1 | 4/2008 | Shoemaker et al. |
| 2008/0286778 | A1 | 11/2008 | Lewin et al. |
| 2008/0286787 | A1 | 11/2008 | Campan et al. |
| 2009/0048427 | A1 | 2/2009 | Hedgpeth et al. |
| 2009/0053719 | A1 | 2/2009 | Lo et al. |
| 2009/0054630 | A1 | 2/2009 | Burns et al. |
| 2010/0009355 | A1 | 1/2010 | Kolodney |
| 2010/0221717 | A1 | 9/2010 | Chen et al. |
| 2010/0285478 | A1 | 11/2010 | Chen et al. |
| 2011/0287424 | A1 | 11/2011 | Chen |
| 2012/0214160 | A1 | 8/2012 | Deng et al. |
| 2016/0040256 | A1 | 2/2016 | Chen et al. |
| 2018/0355420 | A1 | 12/2018 | Chen et al. |

FOREIGN PATENT DOCUMENTS

| | | |
|---|---|---|
| WO | WO-9921881 A1 | 5/1999 |
| WO | WO-03050305 A1 | 6/2003 |
| WO | WO-2007044091 A2 | 4/2007 |
| WO | WO-2007106534 A2 | 9/2007 |
| WO | WO-2008104794 A2 | 9/2008 |
| WO | WO-2010014920 A1 | 2/2010 |
| WO | WO-2010077324 A2 | 7/2010 |
| WO | WO-2010080559 A2 | 7/2010 |
| WO | WO-2010111682 A2 | 9/2010 |
| WO | WO-2010077324 A3 | 10/2010 |
| WO | WO-2010080559 A3 | 10/2010 |
| WO | WO-2011139920 A2 | 11/2011 |
| WO | WO-2011150075 A2 | 12/2011 |
| WO | WO-2012001007 A1 | 1/2012 |
| WO | WO-2012097353 A1 | 7/2012 |
| WO | WO-2012151560 A2 | 11/2012 |
| WO | WO-2014004726 A1 | 1/2014 |

OTHER PUBLICATIONS

Aoyagi, "PCR", Molecular Biology Problem Solver: A Laboratory Guide, 2001, 291-329.
Applied Biosystems, "TaqMan PreAmp Master Mix Kit Protocol" downloaded from URL:hhtp://www3.appliedbiosystems.com/cms/groups/mcb_support/documents/generaldocuments/cms_039316.pdf, Jul. 2010, 33 pages.
Ayyadevara et al., "Discrimination of Primer 3'Nucleotide Mismatch by Taq DNA Polymerase during Polymerase Chain Reaction", Analytical Biochemistry, vol. 284, Issue 1, Aug. 15, 2000, 11-18.
Ballantyne et al., "Locked nucleic acids in PCR primers increase sensitivity and performance", Genomics, vol. 91, No. 3, Mar. 2008, 301-305.
Beattie, "PCR Optimization Kit", MP Biomedicals, Catalog No. 824000, Mar. 19, 1998, 1-9.
Benner et al., "Evolution, language and analogy in functional genomics.", Trends in Genetics, vol. 17, No. 7, Jul. 1, 2001, 414-418.
BIO-RAD, "PCR Tips", Real Time PCR, 1999, pp. 94-99.
Blons et al., "181 Accuracy of castPCR-based KRAS testing on paraffin embedded tissues", European Journal of Cancer Supplements, vol. 8, No. 5, Jun. 2010, 47-48.
Brock et al., "*Thermus aquaticus* gen. n. and sp. n., a Nonsporulating Extreme Thermophile", Journal of Bacteriology, vol. 1, No. 1, 1969, 289-297.
Broude et al., "Stem-loop oligonucleotides: a robust tool for molecular biology and biotechnology", Trends in Biotechnolology, vol. 20, No. 6, Jun. 2002, 249-256.
Bustin, et al., "The MIQE: Minimum Information for Publication of Quantative Real-Time PCT Expirements", Clinical Chemistry, vol. 55, No. 4, 2009, pp. 611-622.
Cantera, et al., "Evolutionary relationship of phototrophic bacteria in the alpha-Proteobacteria based on farnesyl diphosphate synthase", Microbiology, vol. 148, No. 6, 2002, pp. 1923-1929.
Chen et al., "Single nucleotide polymorphism genotyping: biochemistry, protocol, cost and throughput", Pharmacogenomics Journal, vol. 3, No. 2, 2003, 77-96.
Coen, et al., "The Polymerase Chain Reaction", Current Protocols in Molecular Biology, Chs. 15, 1501-15.1.14; Suppls. 88 and 56,2009, pp. 1-17.
Cottrell et al., "A real-time PCR assay for DNA-methylation using methylation-specific blockers", Nucleic Acids Research, vol. 32, No. 1, Jan. 13, 2004, e10 (1-8).
Dharmasiri et al., "Microsystems for the Capture of Low-Abundance Cells", Annual Review of Analytical Chemistry, vol. 3, No. 1, Jul. 2010, 409-431.
Diercks, et al., "Resolving Cell Population Heterogeneity: Real-Time PCR for Simultaneous Multiplexed Gene Detection in Multiple Single-Cell Samples", PLoS ONE, vol. 4, No. 7, 2009, pp. 1-9.
Dominguez, P. et al., ""Wild-type Blocking Polymerase Chain Reaction for detection of single nucleotide minority mutations from clinical specimens"", Oncogene, vol. 24, 2005, pp. 6830-6834.
EP09836510.9; Extended European Search Report dated Jan. 2, 2013, 7 pages.
Extended European Search Report for Application No. 10756973.3, dated Jan. 2, 2013, 8 pages.
Extended European Search Report for Application No. 17166862.7 , dated Oct. 19, 2017, 8 pages.
Gineikiene, Egle et al., "Single Nucleotide Polymorphism-Based System Improves the Applicability of Quantitative PCR for Chimerism Monitoring", The Journal of Molecular Diagnostics, vol. 11, No. 1, American Society for Investigative Pathology and the Association for Molecular Pathology, Jan. 2009; pp. 66-74.
Gormall Y, "Circulating free DNA in plasma or serum as biomarker of carcinogenesis: Practical aspects and biological significance", Mutation Research, vol. 635, Nos. 2-3, 2007, pp. 105-117.
Gray-Schopfer et al., "The role of B-RAF in melanoma", Cancer and Metastasis Reviews, vol. 24, No. 1, Jan. 2005, 165-183.
Hecker, et al., "High and Low Annealing Temperatures Increase Both Specificity and Yield in Touchdown and Stepdown PCR", BioTechniques, vol. 20, No. 3, 1996, pp. 478-485.
Henegariu et al., "Multiplex PCR: Critical Parameters and Step-By-Step Protocol", Biotechniques, vol. 23, No. 3, Sep. 1997, pp. 504-511.
Hiratsuka et al., "Competitive allele-specific short oligonucleotide hybridization (CASSOH) with enzyme-linked immunosorbent assay (ELISA) forthe detection of pharmacogenetic single nucleotide polymorphisms (SNPs)", Journal of Biochemical and Biophysical Methods, vol. 67, Nos. 2-3, Jun. 30, 2006, 87-94.

(56) References Cited

OTHER PUBLICATIONS

Huang et al. "Fluorescence Characteristics of Site-Specific and Stereochemically Distinct Benzo[a]pyrene Diol Epoxide-DNA Adducts as Probes of Adduct Conformation", Chemical Research in Toxicology, vol. 15, Issue 2, Feb. 2002, 118-126.
Imyanitov, E N. et al., "Improved Reliability of Allele-specific PCR", BioTechniques, vol. 33, Issue 3, Sep. 2002; pp. 484-490.
Innis, et al. "PCR Protocols A Guide to Methods and Applications"; 1990, Academic Press, Inc. San Diego, CA, US.
Integrated DNA Technologies, "Modified Bases Catalog Page", downloaded from URL: http://www.idtdna.com/Catalog/Modifications/Modifications.aspx?-catid=7, Mar. 13, 2006.
Intl Application No. PCT/US2009/068610, International Preliminary Report on Patentability dated Jun. 30, 2011, 1-5.
Intl Application No. PCT/US2009/068610, International Search Report and Written Opinion dated Aug. 31, 2010, 1-9.
Intl Application No. PCT/U82011/034675, International Preliminary Report on Patentability dated Nov. 8, 2012, 1-6.
Intl Application No. PCT/US2012/021397, International Preliminary Report on Patentability dated Jul. 16, 2013, 1-7.
Intl Application No. PCT/US2013/047984, International Search Report and Written Opinion dated Aug. 23, 2013, 1-11.
Isacsson, J., et al., Rapid and specific detection of PCR products using light-up probes, Molecular and Cellular Probes, 2000, pp. 321-328, vol. 14., Academic Press.
Itabashi, Tetsuya et al., "Quantitative detection of mutant alleles of the K-ras gene with minor groove binder-conjugated fluorogenic DNA probes", International Journal of Oncology, vol. 24, No. 3, Mar. 1, 2004; pp. 687-696.
Johnson, et al., "Locked nucleic acid (LNA) single nucleotide polymorphism (SNP) genotype analysis and validation using real-time PCR", Nucleic Acids Research, vol. 32, No. 6, 2004, pp. e55 (1-9).
Johnson, M. "Italian Researchers Validate CastPCR as Companion to TKI Treatement for BRAF Mutated Melanoma", Genomeweb Jan. 20, 2016, https://www.genomeweb.com/pcr/italian-researchers-validate-castpcr-compan-ion-tki-treatment-braf-mutated-melanoma; downloaded Feb. 24, 2016, pp. 1-4.
Josefsen et al., "Diagnostic PCR: Comparative sensitivity of four probe chemistries", Molecular and Cellular Probes, vol. 23, Nos. 2-4, Jun.-Aug. 2009, 201-203.
Kerkel, K. et al., "Genomic Surveys by methylation-sensitive SNP analysis identify sequence-dependent allele-specific DNA methylation", Nature Genetics, vol. 40 (7), 2008, pp. 904-908.
Koizumi, M et al., "Improvement of single nucleotide polymorphism genotyping by allele-specific PCR using primers modified with an ENA residue", Analytical Biochemistry, vol. 340(2), Mar. 14, 2005; pp. 287-294.
Kubista, Mikael, et al., Light-up probe based real-time Q-PCR, Genomics and proteomics technologies, 2001, pp. 53-58, val. 4264, SPIE, Bellingham, WA.
Kutyavin, Igor V. et al. "3'-Minor groove binder-DNA probes increase sequence specificity at PCR extension temperatures", Nucleic Acids Research, vol. 28, No. 2, 2000; pp. 655-661.
Kwok, "Methods for Genotyping Single Nucleotide Polymorphisms", Annual Review of Genomics and Human Genetics, vol. 2, 2001, pp. 235-258.
Labrenz, et al., "Development and Application of a Real-Time PCR Approach for Quantification of Uncultured Bacteria in the Central Baltic Sea", Applied and Environmental Microbiology, vol. 70, No. 8, 2004, pp. 4971-4979.
Latorra, D. et al., "Enhanced Allele-Specific PCR Discrimination in SNP Genotyping Using 3' Locked Nucleic Acid (LNA) Primers", Human Mutation, vol. 22, No. 1, John Wiley & Sons, Inc., Jul. 1, 2003; pp. 79-85.
Lee et al., "Increased Sensitivity and Specificity of Borrelia burgdorferi 168 Ribosomal DNA Detection", American Journal of Clinical Pathology, vol. 133, No. 4, Apr. 2010, 569-576.
Livak, "Allelic Discrimination Using Fluorogenic Probes and the 5' Nuclease Assay", Genetic Analysis: Biomolecular Engineering, vol. 14, Nos. 5-6, Feb. 1999, 143-149.
Lu, Janice et al., "Isolation of circulating epithelial and tumor progenitor cells with an invasive phenotype from breast cancer patients", International Journal of Cancer, vol. 126, Issue 3, Feb. 1, 2010; pp. 669-683.
Lukhtanov, et al., "Direct, Solid Phase Assembly of Dihydropyrroloindole Peptides with Conjugated Oligonucleotides", Bioconjugate Chemistry, vol. 7, Issue 5, Sep. 26, 1996; pp. 564-567.
Maniatis, et al., "Molecular cloning: a laboratory manual", Cold Spring Harbor Laboratory, 1982, v-x.
Maxwell et al., "Self-Assembled Nanoparticle Probes for Recognition and Detection of Biomolecules", Journal of the American Chemical Society, vol. 124, No. 32, Aug. 14, 2002, 9606-9612.
May, "How Many Species Are There on Earth?", Science, New Series, vol. 241, No. 4872, Sep. 16, 1988, 1441-1449.
McKinzie et al., "ACB-PCR measurement of K-ras codon 12 mutant fractions in livers of Big BlueRTM. rats treated with N-hydroxy-2-acetylaminofluorene", Mutagenesis, vol. 21, No. 6, Sep. 29, 2006, 391-397.
McKinzie et al., "Detection of rare K-ras codon 12 mutations using allele-specific competitive blocker PCR Mutat Res", Mutation Research, vol. 517, May 27, 2002, 209-220.
Mhlanga, Musa M., et al., Using Molecular Beacons to Detect Single-Nucleotide Polymorphisms with Real-Time PCR, Methods, 2001, pp. 463-471, vol. 25(4), Elsevier Science.
Modrek, Barmak et al., "Genome-wide detection of alternative splicing in expressed sequences of human genes", Nucleic Acids Research, vol. 29, No. 13, Oxford University Press, Jul. 1, 2001; pp. 2850-2859.
Morlan, John et al., "Mutation Detection by Real-Time PCR: A Simple, Robust and Highly Selective Method", PLoS One, vol. 4, Issue 2, e4584.doi:10.1371/journal.pone.0004584, Feb. 25, 2009, 11 pages.
Nakitandwe, J. et al., "Reliable allele detection using SNP-based PCR primers containing Locked Nucleic Acid: application in genetic mapping," Plant Methods, vol. 3, No. 2, Feb. 7, 2007, 9 pages.
Noutsias, et al., "Preamplification techniques for real-time RT-PCR analyses of endomyocardial biopsies", BMC Molecular Biology, vol. 9, No. 3, 2008, pp. 1-20.
Nybo, "Troubleshooting Forum: Molecular Biology Techniques Q&A", DNA and General PCR Methods: Allele-specific PCR, vol. 56, Feb. 2010, 101-102.
Orou et al., "Allele-specific competitive blocker PCR: a one-step method with applicability to pool screening", Human Mutation, vol. 6, No. 2, Jun. 1, 1995, 163-169.
Oshima et al., "Description of *Thermus thermophilus* (*Yoshida* and *Oshima*) comb. nov., a Nonsporulating Thermophilic Bacterium from a Japanese Thermal Spa", International Journal of Systematic Bacteriology, vol. 24, No. 1, 1974, 102-112.
Papp et al., "Single Nucleotide Polymorphism Genotyping Using Allele-Specific PCR and Fluorescence Melting Curves", BioTechniques, vol. 34, No. 5, May 2003, 1068-1072.
Parsons, B. et al., "Allele-specific competitive blocker—PCR detection of rare base substitution", Methods in Molecular Biology, vol. 291, 2005; pp. 235-245.
Parsons, B L. et al., "Detection of a mouse H-ras codon 61 mutation using a modified allele-specific competitive blocker PCR genotype selection method Mutagenesis", Mutagenesis, vol. 13, No. 6, Nov. 1998, 581-588.
PCT/US2009/006652; International Preliminary Report on Patentability dated Jun. 30, 2011, 6 pages.
PCT/US2009/006652; International Search Report and Written Opinion dated Aug. 31, 2010, 11 pages.
PCT/US2010/028963; International Preliminary Report on Patentability dated Oct. 6, 2011, 7 pages.
PCT/US2010/028963; International Search Report and Written Opinion dated Jan. 20, 2011, 11 pages.
PCT/US/2011/034675; International Search Report and Written Opinion dated Feb. 8, 2012, 9 pages.
PCT/US2012/021397; International Search Report and the Written Opinion dated Jun. 22, 2012, 13 pages.

(56) References Cited

OTHER PUBLICATIONS

Piggott, et al., "A multiplex pre-amplification method that significantly improves microsatellite amplification and error rates for faecal DNA in limiting conditions", Conservation Genetics, vol. 5, No. 3, 2004, pp. 417-420.
Punzel, M. et al. "The type of stromal feeder used in limiting dilution assays influences frequency and maintenance assessment of human long-term culture initiating cells", Leukemia,vol. 13, 1999, pp. 92-97.
Reddy, B. S. et al., "Synthetic DNA minor groove-binding drugs", Pharmacology & Therapeutics, vol. 84, Issue 1, Oct. 1999; pp. 1-111.
Riccelli, et al., "Melting studies of dangling-ended DNA hairpins: effects of end length, loop sequence and biotynylationof loop bases", Nucleic Acids Research, vol. 30, No. 18,, Sep. 15, 2002, 4088-4093.
Roobol, C et al., "5-fluorouracil and 5-fluoro-2'-deoxyuridine follow different metabolic pathways in the induction of cell lethality in L1210 leukaemia", British Journal of Cancer, vol. 49, Issue 6, Jun. 1984; pp. 739-744.
Roux, "Optimization and Troubleshooting in PCR", PCR Methods and Applications; Downloaded from www.genome.org; Cold Spring Harbor Laboratory Press, 1995, pp. S185-S194.
Ruano, Gualberto et al., "PCR: The First Few Cycles", Amplifications: A Forum for PCR Users, Issue 7, Perkin Elmer Cetus, Oct. 1991; 4 pages.
Saunders, "Quantitative Real-Time PCR", Current PCR, www.horizonpress.com/pcrboooks, 2008, 1-22.
Seela, F. et al, "The N.sup.8-(2'-deoxyribofuranoside) of 8-aza-7-deazaadenine: a universal nucleoside forming specific hydrogen bonds with the four canonical DNA constituents", Nucleic Acids Research, 2000, vol. 28, No. 17, pp. 3224-3232.
Seyama, et al., "A novel blocker-PCR method for detection of rare mutant alleles in the presence of an excess amount of normal DNA", Nucleic Acids Research, vol. 20, No. 10, 1992, pp. 2493-2496.
Shen, et al., "Abnormal CpG island methylation occurs during in vitro differentiation of human embryonic stem cells", Human Molecular Genetics, vol. 15, No. 17, 2006, pp. 2623-2635.
Solinas, et al., "Duplex Scorpion primers in SNP analysis and FRET applications", Nucleic Acids Research, vol. 29, No. 20, Oct. 15, 2001, E96: 1-9.
Stanley, et al., "TaqMan PreAmp Master Mix Kit for Real-Time Gene Expression Analysis with Sample Limited Specimens,", Jun. 11, 2006, http://www.gene-quantification.com/stanley-AB-2006.pdf).
Stathopoulou et al., "Real-Time Quantification of CK-19 mRNA-Positive Cells in Peripheral Blood of Breast Cancer Patients Using the Lightcycler System", Clinical Cancer Research, vol. 9, No. 14, Nov. 1, 2003, 5145-5151.
Svanvik, Nicke et al., "Light-Up Probes: Thiazole Orange-Conjugated Peptide Nucleic Acid for Detection of Target Nucleic Acid in Homogeneous Solution", Analytical Biochemistry, vol. 281, 2000, 26-35.
Tabone et al., "Temperature Switch PCR (TSP): Robust assay design for reliable amplification and genotyping of SNPs", BMC Genomics, vol. 10, No. 580, Dec. 3, 2009, 1-14.
The International SNP Map Workin, , "A map of human genome sequence variation containing 1.42 million single nucleotide polymorphisms", Nature, vol. 409, Macmillan Magazines Ltd, Feb. 15, 2001; pp. 928-933.
Tsourkas, et al., "Structure-function relationships of shared-stem and conventional molecular beacons", Nucleic Acids Research, vol. 30, No. 19, Oct. 1, 2002, 4208-4215.
Tyagi et al., "Molecular Beacons: Probes that Fluoresce upon Hybridization", Nature Biotechnology, vol. 14, No. 3, Mar. 1996, 303-308.
Uknown, "PCR principles and practices", downloaded from URL: http://irc.igd.cornell.edu/Protocols/PCR _principles.htm, Mar. 10, 2005, pp. 1-3.
Van der Auwera, et al., "Circulating tumour cell detection: a direct comparison between the CeiiSearch System, the AdnaTest and CK-19/mammaglobin RT-PCR in patients with metastatic breast cancer", British Journal of Cancer, vol. 102, No. 2, 2010, pp. 276-284.
Van Hoeyveld et al., "Detection of signel nucleotide polymorphisms in the mannose-binding lectin gene using minor groove binder-DNA probes", Journal of Immunological Methods, vol. 287, 2004, 227-230.
Walker, et al., "Progress in the design of DNA sequence-specific lexitropsins", Biopolymers, vol. 44, No. 4, 1997, pp. 323-334.
Weighardt et al., "A simple procedure for enhancing PCR specificity", Genome Research, vol. 3, No. 1, Aug. 1993, 77-80.
Wemmer, D E. et al., "Targeting the minor groove of DNA", Current Opinion in Structural Biology, vol. 7, Issue 3, 1997; pp. 355-361.
Whitcombe et al., "Detection of PCR Products Using Self-Probing Amplicons and Fluorescence," Nature Biotechnology, Aug. 1999, vol. 17(8), pp. 804-807.
Wolffs, et al., "PNA-Based Light-Up Probes for Real-Time Detection of Sequence-Specific PCR Products", BioTechniques, vol. 31, No. 4, Oct. 2001; pp. 766-771.
Wu, Dan Y. et al., "Allele-Specific Enzymatic Amplification of a Beta-Globin Genomic DNA for Diagnosis of Sickle Cell Anemia", Proceedings of the National Academ~ of Sciences (PNAS), vol. 86(8), National Academy of Sciences ofthe USA, Apr. 1989, 2757-2760.
Yao, et al., "Evaluation of minor groove binding probe and Taqman probe PCR assays: Influence of mismatches and template complexity on quantification", Molecular and Cellular Probes, vol. 20, No. 5, 2006, pp. 311-316.
Yu et al., "Electronic Detection of Single-Base Mismatches in DNA with Ferrocene-Modified Probes", Journal of the American Chemical Society, vol. 123, Issue 45, Nov. 14, 2001, 11155-11161.
Zhang et al. "Hairpin Probes for Real-time Assay of Restriction Endonucleases", Shanghai, vol. 34(2), 2002, 329-332.
Zhang, Y. et al., "Imprinting of Human H19: Allele-specific CpG Methylation, Loss of the Active Allele in Wilms Tumor, and Potential for Somatic Allele Switching", Am. J. Hum. Genet., vol. 53, 1993, pp. 113-124.
Ziegler et al., "Circulating DNA: a new diagnostic gold mine?", Cancer Treatment Reviews, vol. 28, No. 5, Oct. 2002, 255-271.
Zimmer et al., "Nonintercalating DNA-binding ligands: Specificity ofthe interaction and their use as tools in biophysical, biochemical and biological investigations of the genetic material", Progress in Biophysics and Molecular Biology, vol. 47, No. 1, 1986, 31-112.

\* cited by examiner

Use of highly discriminating bases for allele detection (e.g., mutant allele)
Allele-1 (e.g., mutant allele)- specific PCR
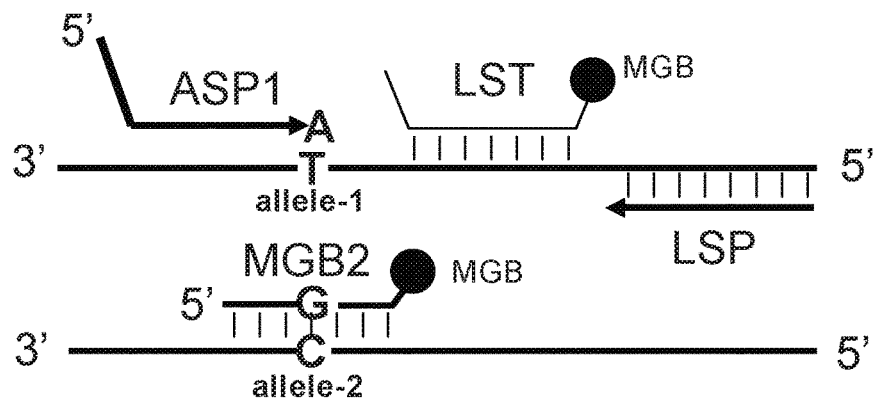
Allele-2 (e.g., wild type allele)- specific PCR
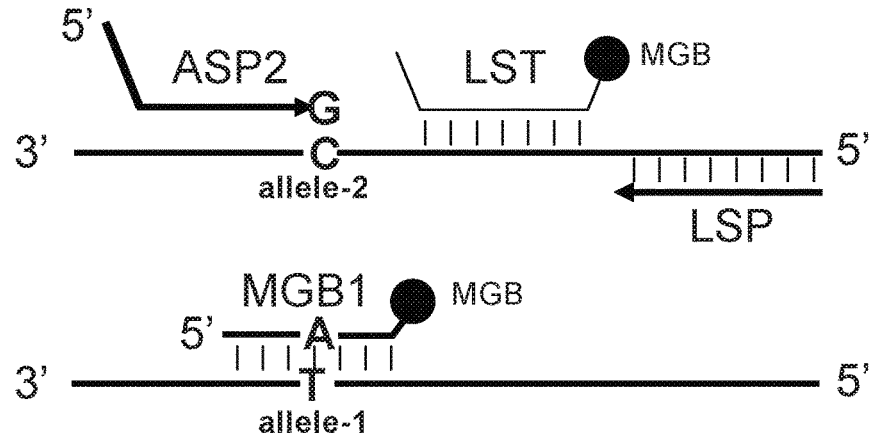
FIG. 2

KRAS mutations

```
  1 gtactggtgg agtatttgat agtgtattaa cctttatgtgt gacatgttct aatatagtca
 61 catttcatt attttattta taaggcctgc tgaaaatgac tgaatataaa cttgtggtag
121 ttggagctgg tggcgtaggc aagagtgcct tgacgataca gctaattcag aatcattttg
181 tggacgaata tgatccaaca atagaggtaa atcttgtttt aatatgcata ttactggtgc
241 aggaccattc tttgatacag ataaaggttt ctctgaccat tttcatgagt
```

/CDS REGION   cod 12-13

KRAS mutations

- 12 Asp (GGT>GAT)
- 12 Val (GGT>GTT)
- 12 Cys (GGT>TGT)
- 12 Ser (GGT>AGT)
- 12 Ala (GGT>GCT)
- 12 Arg (GGT>CGT)
- 13 Asp (GGC>GAC)

FIG. 6

| | Ct_A1 | Ct_A2 | ΔCt | Specificity improvement (fold difference) |
|---|---|---|---|---|
| KRAS-183AC (alelle-1) | 12.6 | 35.7 | 23.1 | 9x10⁶ |
| KRAS-183AC (allele-2) | 34.4 | 13.5 | 20.9 | 2x10⁶ |

FIG. 7C

Detection of Mutant DNA from Tumor Samples by cast-PCR

| SNP ID | Sample ID | Ct_WT | Ct_Mutant | Normalized ΔCt | Mutant cell DNA (%) |
|---|---|---|---|---|---|
| KRA-S38GA | Normal-1 | 23.2 | 40.0 | 16.8 | 0.00 |
| | Tumor-01 | 27.8 | 30.3 | 3.6 | 7.62 |
| EGFR-2573TG | Normal-1 | 22.9 | 40.0 | 17.1 | 0.00 |
| | Tumor-02 | 27.7 | 25.4 | -2 | 80.00 |
| CTNNB1-134CT | Normal-1 | 22.8 | 40 | 17.2 | 0.00 |
| | Tumor-03 | 27.6 | 31.3 | -2.7 | 86.66 |
| KRAS-35GA | Normal-1 | 23.8 | 40 | 16.2 | 0.00 |
| | Tumor-04 | 30.9 | 31.7 | 0 | 50.00 |
| BRAF-1799TA | Normal-1 | 24.5 | 40 | 15.5 | 0.00 |
| | Tumor-05 | 24.5 | 25 | 1.4 | 27.48 |
| NRAS-183AT | Normal-1 | 24.2 | 40 | 15.8 | 0.00 |
| | Tumor-06 | 29.8 | 40.0 | 5.9 | 1.65 |
| TP53-733GA | Normal-1 | 21.8 | 40 | 18.2 | 0.00 |
| | Tumor-07 | 26.2 | 26.1 | 1.2 | 30.33 |

FIG. 10

List of Primers and Probes used in cast-PCR Assays

| SNP ID | Tailed Allele-specific Primer 1 (ASP1) | Sequence of ASP1 | Tailed Allele-specific Primer 2 (ASP2) | Sequence of ASP2 |
|---|---|---|---|---|
| CV11201742 | ASP1 | cccGCTGCTCCTGTGC | ASP2 | cccGCTGCTCCTGTGT |
| CV11349123 | ASP1 | acccAACGCACAACTTAGCG | ASP2 | gccGAACGCACAACTTAGCA |
| CV1207700 | ASP1 | cccgCCTTGATGGATGGAGATTTAC | ASP2 | cccgCCTTGATGGATGGAGATTTAT |
| CV25594064 | ASP1 | gcacCCTTGGTGAAACAATTGTTG | ASP2 | tgcacCCTTGGTGAAACAATTGTTC |
| CV25639181 | ASP1 | cgccGAACTGGAAGTATTTTGACAG | ASP2 | cgccGAACTGGAAGTATTTTGACAT |

| SNP ID | Locus-specific Primer (LSP) | Sequence of LSP | Locus-specific TaqMan Probe (LST) | Sequence of LST |
|---|---|---|---|---|
| CV11201742 | LSP | TATCCCTCACAGAGAAGGGAG | LST | (6-FAM)ATGGCCCTGATAAGGGAGA(MGB) |
| CV11349123 | LSP | GCTTGCAATGGCTCCAACC | LST | (6-FAM)AGGGCGGTGCTGAG(MGB) |
| CV1207700 | LSP | GGAGCCATTGCAAGCCAAG | LST | (6-FAM)TGTCACTCTACCCAGTAAA(MGB) |
| CV25594064 | LSP | TGGCAAGAGCGATGAGTACTC | LST | (6-FAM)AGAATCTGCCAATTACCTAGA(MGB) |
| CV25639181 | LSP | CTCTCAAAAGGTAACTGCCCACTTA | LST | (6-FAM)ACAAGTAGCTGATAATAAATG(MGB) |

| SNP ID | MGB Blocker 1 (MGB1) | Sequence of MGB1 | MGB Blocker 2 (MGB2) | Sequence of MGB2 |
|---|---|---|---|---|
| CV11201742 | MGB1 | CTCCTGTGCTGTCACC(MGB) | MGB2 | GCTCCTGTGTTGTCACC(MGB) |
| CV11349123 | MGB1 | CTTAGCGGGCACGCAC(MGB) | MGB2 | CTTAGCAGCACGACC(MGB) |
| CV1207700 | MGB1 | GGAGATTTACGCAATGTG(MGB) | MGB2 | TGGAGATTTATGCAATGTG(MGB) |
| CV25594064 | MGB1 | ACAATTGTTGAGGGGGG(MGB) | MGB2 | ACAATTGTTCAGGGGGG(MGB) |
| CV25639181 | MGB1 | AAGTATTTTGACAGCTTTAC(MGB) | MGB2 | AAGTATTTTGACATCTTTAC(MGB) |

FIG. 11A

| SNP ID | Tailed Allele-specific Primer 1 (ASP1) | Sequence of ASP1 | Tailed Allele-specific Primer 2 (ASP2) | Sequence of ASP2 |
|---|---|---|---|---|
| BRAF-1799TA | ASP1 | GCCTGATTTTGGTCTAGCTACAGA | ASP2 | CCGGATTTTGGTCTAGCTACAGT |
| CTNNB1-121AG | ASP1 | CGGGAGAAGGAGCTGTGGT | ASP2 | GCCAGAAGGAGCTGTGGC |
| CTNNB1-134CT | ASP1 | CCGTGCCTTACCACTCAGAG | ASP2 | CCGTGCCTTACCACTCAGAA |
| EGFR-2369CT | ASP1 | GCGGTGCAGCTCATCAC | ASP2 | GCGGTGCAGCTCATCAT |
| EGFR-2573TG | ASP1 | CGGCAGCAGTTTGGCC | ASP2 | CGGCAGCAGTTTGGCCA |
| KRAS-176CG | ASP1 | GCCGGATATTCTCGACACAGC | ASP2 | CGCTGGATATTCTCGACACAGG |
| KRAS-183AC | ASP1 | GCGGACACAGCAGGTCAA | ASP2 | GCGGACACAGCAGGTCAC |
| KRAS-183AT | ASP1 | GCGGACACAGCAGGTCAA | ASP2 | GCGGACACAGCAGGTCAT |
| KRAS-34GA | ASP1 | CGCCTTGCCTACGCCACT | ASP2 | GCGTTGCCTACGCCACC |
| KRAS-34GC | ASP1 | CGCTGCCTACGCCACG | ASP2 | GCGTTGCCTACGCCACC |
| KRAS-34GT | ASP1 | GCGTTGCCTACGCCACA | ASP2 | GCGTTGCCTACGCCACA |
| KRAS-35GA | ASP1 | CGCCTCTTGCCTACGCCAT | ASP2 | GCGTCTTGCCTACGCCAC |
| KRAS-35GC | ASP1 | GCGTCTTGCCTACGCCAG | ASP2 | GCGTCTTGCCTACGCCAC |
| KRAS-35GT | ASP1 | GCGTCTTGCCTACGCCAC | ASP2 | GCGTCTTGCCTACGCCAA |
| KRAS-3GA | ASP1 | CGGTAGTTGGAGCTGGTGA | ASP2 | GCCTAGTTGGAGCTGGTGG |
| NRAS-181CA | ASP1 | CCGATACTGGATACAGCTGGAA | ASP2 | CCGATACTGGATACAGCTGGAC |
| NRAS-183AT | ASP1 | CCGTGGATACAGCTGGACAA | ASP2 | CGCCTGGATACAGCTGGACAT |
| NRAS-35GA | ASP1 | CCGGTGGTTGGAGCAGA | ASP2 | CCGGTGGTTGGAGCAGG |
| NRAS-38GA | ASP1 | CCGGTGGGAGCAGGTGA | ASP2 | CCGGTGGGAGCAGGTGG |
| TP53-524GA | ASP1 | CCGGAGGTTGTGAGGCA | ASP2 | GGGAGGTTGTGAGGCG |
| TP53-637CT | ASP1 | GCCTGGATGACAGAAACACTTTTC | ASP2 | GCCTGGATGACAGAAACACTTTT |
| TP53-721TG | ASP1 | GCGTACAACTACATGTAACAGTG | ASP2 | GGCCTACAACTACATGTAACAGTT |
| TP53-733GA | ASP1 | GCCTCCTGCATGGGCA | ASP2 | GCCTCCTGCATGGGCG |
| TP53-742CT | ASP1 | GCCGGGGCATGAACC | ASP2 | GCGGGGCATGAACT |
| TP53-743GA | ASP1 | GCCGGGCATGAACCA | ASP2 | GCCGGGCATGAACCG |
| TP53-817CT | ASP1 | GCCAACAGCTTTGAGGTGC | ASP2 | CGCGAACAGCTTTGAGGTGT |

FIG. 11B

| SNP ID | Locus-specific Primer (LSP) | Sequence of LSP | Locus-specific TaqMan Probe (LST) | Sequence of LST |
|---|---|---|---|---|
| BRAF-1799TA | LSP | AGCCTCAATTCTTACCATCCACAAAA | LST | (6-FAM)CAGACAACTGTTCAAACTG(MGB) |
| CTNNB1-121AG | LSP | CATGGAACCAGACAGAAAAGCG | LST | (6-FAM)CTGGCAGCAACAGTCT(MGB) |
| CTNNB1-134CT | LSP | GTCACTGGCAGCAACAGTCTTA | LST | (6-FAM)TAGTGGCACCAGAATGG(MGB) |
| EGFR-2369CT | LSP | TGGGAGCCAATATTGTCTTTGTGTT | LST | (6-FAM)CCCTTCGGCTGCCTCC(MGB) |
| EGFR-2573TG | LSP | AGGAACGTACTGGTGAAAACACC | LST | (6-FAM)CAGACATGTCAAGATCAC(MGB) |
| KRAS-176CG | LSP | CCCTCCCAGTCCTCATGTA | LST | (6-FAM)CTGGTCCTCATTGCAC(MGB) |
| KRAS-183AC | LSP | TCTTCAAATGATTTAGTATTATTTATGGCAAATACACAAAG | LST | (6-FAM)CCCTCCCCAGTCCTCA(MGB) |
| KRAS-183AT | LSP | TCTTCAAATGATTTAGTATTATTTATGGCAAATACACAAAG | LST | (6-FAM)CCCTCCCCAGTCCTCA(MGB) |
| KRAS-34GA | LSP | TGTGTGACATGTTCTAATATAGTCACAT | LST | (6-FAM)CCTGCTGAAAATGAC(MGB) |
| KRAS-34GC | LSP | TGTGTGACATGTTCTAATATAGTCACAT | LST | (6-FAM)CCTGCTGAAAATGAC(MGB) |
| KRAS-34GT | LSP | TGTGTGACATGTTCTAATATAGTCACAT | LST | (6-FAM)CCTGCTGAAAATGAC(MGB) |
| KRAS-35GA | LSP | TGTGTGACATGTTCTAATATAGTCACAT | LST | (6-FAM)CCTGCTGAAAATGAC(MGB) |
| KRAS-35GC | LSP | TGTGTGACATGTTCTAATATAGTCACAT | LST | (6-FAM)CCTGCTGAAAATGAC(MGB) |
| KRAS-35GT | LSP | TGTGTGACATGTTCTAATATAGTCACAT | LST | (6-FAM)CCTGCTGAAAATGAC(MGB) |
| KRAS-3GA | LSP | GGTCCTGCACCAGTAATATGCA | LST | (6-FAM)TCGTCCACAAAATGATTC(MGB) |
| NRAS-181CA | LSP | GCAAATGACTTGCTATTATTGATGGCAAA | LST | (6-FAM)CCTTGCCTGTCCTCATG(MGB) |
| NRAS-183AT | LSP | GCAAATGACTTGCTATTATTGATGGCAAA | LST | (6-FAM)CCTTGCCTGTCCTCATG(MGB) |
| NRAS-35GA | LSP | AGTGGTTCTGGATTAGCTGGATTG | LST | (6-FAM)CAGTGCGCTTTTCC(MGB) |
| NRAS-38GA | LSP | GTGGTTCTGGATTAGCTGGATTGT | LST | (6-FAM)CAGTGCGCTTTTCC(MGB) |
| TP53-524GA | LSP | GCAACCAGCCCTGTGTC | LST | (6-FAM)CTGCTCACCATCGCTATC(MGB) |
| TP53-637CT | LSP | AGACCCCAGTTGCAAACCAG | LST | (6-FAM)CCTCAGGCGGCTCATAG(MGB) |
| TP53-721TG | LSP | CTGGAGTCTTCCAGTGTGATGATG | LST | (6-FAM)ATGGCCTCCGGTTCAT(MGB) |
| TP53-733GA | LSP | CTGGAGTCTTCCAGTGTGATGAT | LST | (6-FAM)ACGGAGGCCATCT(MGB) |
| TP53-742CT | LSP | TGTGCAGGGTGGCAAGT | LST | (6-FAM)CACACTGGAAGACTCC(MGB) |
| TP53-743GA | LSP | TGTGCAGGGTGGCAAGT | LST | (6-FAM)CACACTGGAAGACTCC(MGB) |
| TP53-817CT | LSP | CTTTCTTGCGGGAGATTCTCTTCCT | LST | (6-FAM)CTGTGCCGGTCTC(MGB) |

FIG. 11C

| SNP ID | MGB Blocker 1 (MGB1) | Sequence of MGB1 | MGB Blocker 2 (MGB2) | Sequence of MGB2 |
|---|---|---|---|---|
| BRAF-1799TA | MGB1 | GCTACAGAGAAATCTC(MGB) | MGB2 | GCTACAGTGAAATCTC(MGB) |
| CTNNB1-121AG | MGB1 | GAGCTGTGGTAGTGGCA(MGB) | MGB2 | AGCTGTGGCAGTGGCA(MGB) |
| CTNNB1-134CT | MGB1 | CACTCAGAAGGAGC(MGB) | MGB2 | CACTCAGAAAAGGAGC(MGB) |
| EGFR-2369CT | MGB1 | CATCACGCAGTCTCATG(MGB) | MGB2 | TCATCATGCAGTCTCATG(MGB) |
| EGFR-2573TG | MGB1 | AGTTTGGCCCGCCCAA(MGB) | MGB2 | AGTTTGGCAGCCCAA(MGB) |
| KRAS-176CG | MGB1 | CTCGACACAGCAGGTCA(MGB) | MGB2 | CTCGACACAGGAGGTCA(MGB) |
| KRAS-183AC | MGB1 | GCAGGTCAAGAGGAGTAC(MGB) | MGB2 | CAGGTCACGAGGAGTAC(MGB) |
| KRAS-183AT | MGB1 | GCAGGTCAAGAGGAGTAC(MGB) | MGB2 | GCAGGTCATGAGGAGTAC(MGB) |
| KRAS-34GA | MGB1 | CGCCACTAGCTCCA(MGB) | MGB2 | CGCCACCAGCTCC(MGB) |
| KRAS-34GC | MGB1 | CCACGAGCTCCAACTA(MGB) | MGB2 | CCACCAGCTCCAACTA(MGB) |
| KRAS-34GT | MGB1 | ACGCCACCAGCTCC(MGB) | MGB2 | ACGCCACCAGCTCCAA(MGB) |
| KRAS-35GA | MGB1 | CGCCATCAGCTCC(MGB) | MGB2 | CGCCACCAGCTCC(MGB) |
| KRAS-35GC | MGB1 | CGCCAGCAGCTCC(MGB) | MGB2 | CGCCACCAGCTCC(MGB) |
| KRAS-35GT | MGB1 | CGCCACCAGCTCCA(MGB) | MGB2 | CGCCAACAGCTCCAA(MGB) |
| KRAS-3GA | MGB1 | GCTGGTGACGTAGGC(MGB) | MGB2 | GCTGGTGGCGTAGGC(MGB) |
| NRAS-181CA | MGB1 | GCTGGAAAAGAAGAGTAC(MGB) | MGB2 | GCTGGACAAGAAGAGTAC(MGB) |
| NRAS-183AT | MGB1 | CAGCTGGACAAGAAGAG(MGB) | MGB2 | CAGCTGGACATGAAGAG(MGB) |
| NRAS-35GA | MGB1 | TTGGAGCAGATGGTGTT(MGB) | MGB2 | TGGAGCAGGTGGTGTT(MGB) |
| NRAS-38GA | MGB1 | TGGAGCAGGTGATGTT(MGB) | MGB2 | TGGAGCAGGTGGTGTT(MGB) |
| TP53-524GA | MGB1 | TGAGGCACTGCCC(MGB) | MGB2 | TGAGGCGCTGCCCAA(MGB) |
| TP53-637CT | MGB1 | GAAAACACTTTTGACATAGTGGTG(MGB) | MGB2 | AGAAACACTTTTGACATAGTGTGGTG(MGB) |
| TP53-721TG | MGB1 | TGTGTAACAGTGCCTGCATG(MGB) | MGB2 | ATGTGTAACAGTTCCTGCATG(MGB) |
| TP53-733GA | MGB1 | GCATGGGCAGCATG(MGB) | MGB2 | GCATGGGCGGCATG(MGB) |
| TP53-742CT | MGB1 | GCATGAACCGGAGGC(MGB) | MGB2 | GCATGAACTGGAGGC(MGB) |
| TP53-743GA | MGB1 | CATGAACCAGAGGCC(MGB) | MGB2 | CATGAACCGGAGGCC(MGB) |
| TP53-817CT | MGB1 | TTGAGGTGCGTGTTTGTG(MGB) | MGB2 | TTTGAGGTGGTGTTTGTGC(MGB) |

FIG. 11D

SEQUENCE LISTING

```
<160> NUMBER OF SEQ ID NOS: 223

<210> SEQ ID NO 1
<211> LENGTH: 144
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
gctctgcttc attcctgtct gaagaagggc agatagtttg gctgctcctg tgytgtcacc      60
tgcaattctc ccttatcagg gccattggcc tctcccttct ctctgtgagg gatattttct    120
ctgacttgtc aatccacatc ttcc                                            144

<210> SEQ ID NO 2
<211> LENGTH: 82
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggcttgcaat ggctccaacc ggaagggcgg tgctcgagct gtggtgcgtg cygctaagtt      60
gtgcgttcca gggtgcactc gc                                               82

<210> SEQ ID NO 3
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gcaactatac ccttgatgga tggagattta ygcaatgtgt tttactgggt agagtgacag      60
acctt                                                                  65
```

<210> SEQ ID NO 4
<211> LENGTH: 124
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
cctgaactta tttggcaaga gcgatgagta ctcttaaaat tactatctgg aaattatatt      60
atttagaatc tgccaattac ctagatcccc cctsaacaat tgtttcacca aggaacttcc    120
tgaa                                                                 124

<210> SEQ ID NO 5
<211> LENGTH: 180
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gaattggttg tctccttatg ggaactggaa gtattttgac akctttacca catttcttca      60
tgggatagta agtgttaaac agctctgagc catttattat cagctacttg taaattagca    120
gtagaatttt atttttatac ttgtaagtgg gcagttacct tttgagagga atacctatag    180

<210> SEQ ID NO 6
<211> LENGTH: 87
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gcggagggaa gctcatcagt ggggccacga gctgagtgcg tcctgtcact ccactcccat      60
gtcccttggg aaggtctgag actaggg                                         87

<210> SEQ ID NO 7
<211> LENGTH: 192
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
tactacacct cagatatatt tcttcatgaa gacctcacag taaaaatagg tgattttggt      60
ctagctacag wgaaatctcg atggagtggg tcccatcagt ttgaacagtt gtctggatcc    120
attttgtgga tggtaagaat tgaggctatt tttccactga ttaaattttt ggccctgaga    180
tgctgctgag tt                                                        192

<210> SEQ ID NO 8
<211> LENGTH: 198
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
tgctaatact gtttcgtatt tatagctgat ttgatggagt tggacatggc catggaacca    60
gacagaaaag cggctgttag tcactggcag caacagtctt acctggactc tggaatccat   120
tctggtgcca ctrccacagc tccttctctg agtggtaaag caatcctga ggaagaggat   180 gtggatacct cccaagtc                                                  198
```

<210> SEQ ID NO 9
<211> LENGTH: 184
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

```
tttgatggag ttggacatgg ccatggaacc agacagaaaa gcggctgtta gtcactggca    60
gcaacagtct tacctggact ctggaatcca ttctggtgcc actaccacag ctccttytct   120
gagtggtaaa gcaatcctg aggaagagga tgtggatacc tcccaagtcc tgtatgagtg   180
ggaa                                                                 184
```

<210> SEQ ID NO 10
<211> LENGTH: 181
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

```
gtggacaacc cccacgtgtg ccgcctgctg ggcatctgcc tcacctccac cgtgcagctc    60
atcaygcagc tcatgcccct cggctgcctc ctggactatg tccgggaaca caaagacaat   120
attggctccc agtacctgct caactggtgt gtgcagatcg caaaggtaat cagggaaggg   180
a                                                                    181
```

<210> SEQ ID NO 11
<211> LENGTH: 166
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gcatgaacta cttggaggac cgtcgcttgg tgcaccgcga cctggcagcc aggaacgtac    60
tggtgaaaac accgcagcat gtcaagatca cagattttgg gckggccaaa ctgctgggtg   120
cggaagagaa agaataccat gcagaaggag gcaaagtaag gaggtg                  166
```

<210> SEQ ID NO 12
<211> LENGTH: 172
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
caggattcct acaggaagca agtagtaatt gatggagaaa cctgtctctt ggatattctc    60
gacacagsag gtcaagagga gtacagtgca atgagggacc agtacatgag gactggggag   120
ggctttcttt gtgtatttgc cataaataat actaaatcat ttgaagatat tc           172
```

<210> SEQ ID NO 13
<211> LENGTH: 207
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
acaggaagca agtagtaatt gatggagaaa cctgtctctt ggatattctc gacacagcag    60
gtcamgagga gtacagtgca atgagggacc agtacatgag gactggggag ggctttcttt   120
gtgtatttgc cataaataat actaaatcat ttgaagatat tcaccattat aggtgggttt   180
aaattgaata taataagctg acattaa                                      207

<210> SEQ ID NO 14
<211> LENGTH: 169
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
tattaacctt atgtgtgaca tgttctaata tagtcacatt ttcattattt ttattataag    60
gcctgctgaa aatgactgaa tataaacttg tggtagttgg agctrgtggc gtaggcaaga   120
gtgccttgac gatacagcta attcagaatc attttgtgga cgaatatga              169

<210> SEQ ID NO 15
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15
tattaacctt atgtgtgaca tgttctaata tagtcacatt ttcattattt ttattataag    60
gcctgctgaa aatgactgaa tataaacttg tggtagttgg agctgrtggc gtaggcaaga   120
gtgccttgac gatacagcta attcagaatc attttgtgga cgaatatgat c           171

<210> SEQ ID NO 16
<211> LENGTH: 230
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
cattattttt attataaggc ctgctgaaaa tgactgaata taaacttgtg gtagttggag    60
ctggtgrcgt aggcaagagt gccttgacga tacagctaat tcagaatcat tttgtggacg   120
aatatgatcc aacaatagag gtaaatcttg ttttaatatg catattactg gtgcaggacc   180
attctttgat acagataaag gtttctctga ccatttcat gagtacttat               230

<210> SEQ ID NO 17
<211> LENGTH: 210
<212> TYPE: DNA
<213> ORGANISM: Artificial Sequence
<220> FEATURE:

<223> OTHER INFORMATION: Description of Artificial Sequence: Synthetic
      polynucleotide

<400> SEQUENCE: 17
attcttacag aaaacaagtg gttatagatg gtgaaacctg tttgttggac atactggata     60
cagctggama agaagagtac agtgccatga gagaccaata catgaggaca ggcgaaggct    120
tcctctgtgt atttgccatc aataatagca agtcatttgc ggatattaac ctctacaggt    180
actaggagca ttattttctc tgaaaggatg                                     210

<210> SEQ ID NO 18
<211> LENGTH: 206
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18
ttacagaaaa caagtggtta tagatggtga aacctgtttg ttggacatac tggatacagc     60
tggacawgaa gagtacagtg ccatgagaga ccaatacatg aggacaggcg aaggcttcct    120
ctgtgtattt gccatcaata atagcaagtc atttgcggat attaacctct acaggtacta    180
ggagcattat tttctctgaa aggatg                                         206

<210> SEQ ID NO 19
<211> LENGTH: 162
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
tggtttccaa caggttcttg ctggtgtgaa atgactgagt acaaactggt ggtggttgga     60
gcagrtggtg ttgggaaaag cgcactgaca atccagctaa tccagaacca ctttgtagat    120
gaatatgatc ccaccataga ggtgaggccc agtggtagcc cg                       162

<210> SEQ ID NO 20
<211> LENGTH: 158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
tttccaacag gttcttgctg gtgtgaaatg actgagtaca aactggtggt ggttggagca     60
ggtgrtgttg ggaaaagcgc actgacaatc cagctaatcc agaaccactt tgtagatgaa    120
tatgatccca ccatagaggt gaggcccagt ggtagccc                            158

<210> SEQ ID NO 21
<211> LENGTH: 189
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
ggcacccgcg tccgcgccat ggccatctac aagcagtcac agcacatgac ggaggttgtg     60

```
aggcrctgcc cccaccatga gcgctgctca gatagcgatg gtgagcagct ggggctggag      120
agacgacagg gctggttgcc cagggtcccc aggcctctga ttcctcactg attgctctta      180
ggtctggcc                                                              189
```

<210> SEQ ID NO 22
<211> LENGTH: 165
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

```
cctcctcagc atcttatccg agtggaagga aatttgcgtg tggagtattt ggatgacaga      60
aacactttty gacatagtgt ggtggtgccc tatgagccgc ctgaggtctg gtttgcaact     120
ggggtctctg ggaggagggg ttaagggtgg ttgtcagtgg ccctc                     165
```

<210> SEQ ID NO 23
<211> LENGTH: 183
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23

```
cttgggcctg tgttatctcc taggttggct ctgactgtac caccatccac tacaactaca      60
tgtgtaacag tkcctgcatg ggcggcatga accggaggcc catcctcacc atcatcacac     120
tggaagactc caggtcagga gccacttgcc accctgcaca ctggcctgct gtgccccagc     180
ctc                                                                   183
```

<210> SEQ ID NO 24
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24

```
taggttggct ctgactgtac caccatccac tacaactaca tgtgtaacag ttcctgcatg      60
ggcrgcatga accggaggcc catcctcacc atcatcacac tggaagactc caggtcagga     120
gccacttgcc accctgcaca ctggcctgct gtgccccagc ctc                       163
```

<210> SEQ ID NO 25
<211> LENGTH: 163
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25

```
ctgactgtac caccatccac tacaactaca tgtgtaacag ttcctgcatg ggcggcatga      60
acyggaggcc catcctcacc atcatcacac tggaagactc caggtcagga gccacttgcc     120
accctgcaca ctggcctgct gtgccccagc tctgcttgc ctc                        163
```

<210> SEQ ID NO 26
<211> LENGTH: 162

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
tgactgtacc accatccact acaactacat gtgtaacagt tcctgcatgg gcggcatgaa      60
ccrgaggccc atcctcacca tcatcacact ggaagactcc aggtcaggag ccacttgcca    120
ccctgcacac tggcctgctg tgccccagcc tctgcttgcc tc                       162

<210> SEQ ID NO 27
<211> LENGTH: 176
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 27
cctcttgctt ctcttttcct atcctgagta gtggtaatct actgggacgg aacagctttg     60
aggtgygtgt ttgtgcctgt cctgggagag accggcgcac agaggaagag aatctccgca   120
agaaagggga gcctcaccac gagctgcccc cagggagcac taagcgaggt aagcaa        176

<210> SEQ ID NO 28
<211> LENGTH: 601
<212> TYPE: DNA
<213> ORGANISM: Homo sapiens

<400> SEQUENCE: 28
agaaaataac taagggaagg aggaaagtgg ggaggaagga agaacagtgt gaagacaatg     60
gcctgaaaac tgaaaaagtc tgttaaagtt aattatcagt ttttgagtcc aagaactggc   120
tttgctactt tctgtaagtt tctaatttac tgaataagca tgaaaaagat tgctttgagg   180
aatggttata aacacattct tagagcatag taagcagtag ggagtaacaa ataacactg    240 attagaatac tttactctac ttaattaatc aatcatattt agtttgactc accttcccag   300
haccttctag ttctttctta tctttcagtg cttgtccaga caacattttc atttcaacaa   360
ctcctgctat tgcaatgatg ggtacaattg ctaagagtaa cagtgttagt tgccaaccat   420
agatgaagga tataattatt cctgtcccaa gatttgctat attctgggta attacagcaa   480
gcctggaacc tatagcctgc aaaacaaaac aaattagaga aattttaaaa atattatctt   540
cacaactcat gcttctattt tctgaaaact caccttcatg agactatatt cattatttta   600
t                                                                   601

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
atatttagtt tgactcacct tcccagc                                         27

<210> SEQ ID NO 30
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 30
accactcacc tttcccagc                                                    19

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
atatttagtt tgactcacct tcccaga                                           27

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
accactcacc tttcccaga                                                    19

<210> SEQ ID NO 33
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
atatttagtt tgactcacct tcccagt                                           27

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
accactcacc tttcccagt                                                    19

<210> SEQ ID NO 35
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 35
tggacaagca ctgaaaga                                                     18

<210> SEQ ID NO 36
<211> LENGTH: 27
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 36
gcaggagttg ttgaaatgaa aatgttg                                          27

<210> SEQ ID NO 37
<211> LENGTH: 289
<212> TYPE: DNA
<213> ORGANISM: Homo sapiens

<400> SEQUENCE: 37
gtactggtgg agtatttgat agtgtattaa ccttatgtgt gacatgttct aatatagtca      60
cattttcatt atttttatta taaggcctgc tgaaaatgac tgaatataaa cttgtggtag     120
ttggagctgg tggcgtaggc aagagtgcct gacgatacag ctaattcaga atcattttgt     180
ggacgaatat gatccaacaa tagaggtaaa tcttgtttta atatgcatat tactggtgca     240
ggaccattct ttgatacaga taaaggtttc tctgaccatt ttcatgagt                 289

<210> SEQ ID NO 38
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cccgctgctc ctgtgc                                                      16

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
acccaacgca caacttagcg                                                  20

<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cccgccttga tggatggaga tttac                                            25

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gcacccttgg tgaaacaatt gttg                                             24

<210> SEQ ID NO 42

```
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
cgccgaactg gaagtatttt gacag                                                25

<210> SEQ ID NO 43
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tatccctcac agagagaagg gag                                                  23

<210> SEQ ID NO 44
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gcttgcaatg gctccaacc                                                       19

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ggagccattg caagccaag                                                       19

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tggcaagagc gatgagtact c                                                    21

<210> SEQ ID NO 47
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ctctcaaaag gtaactgccc actta                                                25

<210> SEQ ID NO 48
<211> LENGTH: 16
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ctcctgtgct gtcacc                                                      16

<210> SEQ ID NO 49
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cttagcggca cgcac                                                       15

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ggagatttac gcaatgtg                                                    18

<210> SEQ ID NO 51
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
acaattgttg agggggg                                                     17

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
aagtattttg acagctttac                                                  20

<210> SEQ ID NO 53
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
cccggctgct cctgtgt                                                     17

<210> SEQ ID NO 54
<211> LENGTH: 20
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 54
gccgaacgca caacttagca                                                   20

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cccgccttga tggatggaga tttat                                             25

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tgcacccttg gtgaaacaat tgttc                                             25

<210> SEQ ID NO 57
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cgccgaactg aagtattttt gacat                                             25

<210> SEQ ID NO 58
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 58
atggccctga taagggaga                                                    19

<210> SEQ ID NO 59
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
agggcggtgc tcgag                                                        15

<210> SEQ ID NO 60
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 60
tgtcactcta cccagtaaa                                                    19

<210> SEQ ID NO 61
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 61
agaatctgcc aattacctag a                                                 21

<210> SEQ ID NO 62
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 62
acaagtagct gataataaat g                                                 21

<210> SEQ ID NO 63
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
gctcctgtgt tgtcacc                                                      17

<210> SEQ ID NO 64
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
cttagcagca cgcacc                                                       16

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
tggagattta tgcaatgtg                                                    19

<210> SEQ ID NO 66
<211> LENGTH: 17
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 66
acaattgttc aggggggg                                                       17

<210> SEQ ID NO 67
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aagtattttg acatctttac                                                     20

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gcctgatttt ggtctagcta caga                                                24

<210> SEQ ID NO 69
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cgcgagaagg agctgtggt                                                      19

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ccgtgccttt accactcaga g                                                   21

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gcgcgtgcag ctcatcac                                                       18

<210> SEQ ID NO 72
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
cggcagcagt ttggccc                                                  17

<210> SEQ ID NO 73
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gccggatatt ctcgacacag c                                             21

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcggacacag caggtcaa                                                 18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
gcggacacag caggtcaa                                                 18

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cgccttgcct acgccact                                                 18

<210> SEQ ID NO 77
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
cgctgcctac gccacg                                                   16

<210> SEQ ID NO 78
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 78
gcgttgccta cgccacc                                                      17

<210> SEQ ID NO 79
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgcctcttgc ctacgccat                                                    19

<210> SEQ ID NO 80
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gcgtcttgcc tacgccag                                                     18

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
gcgtcttgcc tacgccac                                                     18

<210> SEQ ID NO 82
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
cgcgtagttg gagctggtga                                                   20

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ccgatactgg atacagctgg aa                                                22

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 84
ccgtggatac agctggacaa                                                    20

<210> SEQ ID NO 85
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ccgggtggtt ggagcaga                                                      18

<210> SEQ ID NO 86
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ccgggttgga gcaggtga                                                      18

<210> SEQ ID NO 87
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
ccgggaggtt gtgaggca                                                      18

<210> SEQ ID NO 88
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
gccggatgac agaaacactt ttc                                                23

<210> SEQ ID NO 89
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
gcgtacaact acatgtgtaa cagtg                                              25

<210> SEQ ID NO 90
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
```
gccttcctgc atgggca                                          17

<210> SEQ ID NO 91
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gccggcggca tgaacc                                           16

<210> SEQ ID NO 92
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
gccgcggcat gaacca                                           16

<210> SEQ ID NO 93
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
gccaacagct ttgaggtgc                                        19

<210> SEQ ID NO 94
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
ccggattttg gtctagctac agt                                   23

<210> SEQ ID NO 95
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
gccagaagga gctgtggc                                         18

<210> SEQ ID NO 96
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ccgtgccttt accactcaga a                                       21

<210> SEQ ID NO 97
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
gcgcgtgcag ctcatcat                                           18

<210> SEQ ID NO 98
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cggcagcagt ttggcca                                            17

<210> SEQ ID NO 99
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cgctggatat tctcgacaca gg                                      22

<210> SEQ ID NO 100
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
gcggacacag caggtcac                                           18

<210> SEQ ID NO 101
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
gcggacacag caggtcat                                           18

<210> SEQ ID NO 102
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
gcgttgccta cgccacc                                            17

<210> SEQ ID NO 103
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
gcgttgccta cgccacc                                                      17

<210> SEQ ID NO 104
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
gcgttgccta cgccaca                                                      17

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
gcgtcttgcc tacgccac                                                     18

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
gcgtcttgcc tacgccac                                                     18

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gcgtcttgcc tacgccaa                                                     18

<210> SEQ ID NO 108
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gcctagttgg agctggtgg                                                    19

```
<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
ccgatactgg atacagctgg ac                                              22

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
cgcctggata cagctggaca t                                               21

<210> SEQ ID NO 111
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
cgcgtggttg gagcagg                                                    17

<210> SEQ ID NO 112
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
cgcgttggag caggtgg                                                    17

<210> SEQ ID NO 113
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
ggcgaggttg tgaggcg                                                    17

<210> SEQ ID NO 114
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
gcctggatga cagaaacact tttt                                            24
```

```
<210> SEQ ID NO 115
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 115
ggcctacaac tacatgtgta acagtt                                          26

<210> SEQ ID NO 116
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 116
gcctcctgca tgggcg                                                     16

<210> SEQ ID NO 117
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 117
gccggcggca tgaact                                                     16

<210> SEQ ID NO 118
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 118
gccgcggcat gaaccg                                                     16

<210> SEQ ID NO 119
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 119
cgcgaacagc tttgaggtgt                                                 20

<210> SEQ ID NO 120
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 120
agcctcaatt cttaccatcc acaaaa                                          26

<210> SEQ ID NO 121
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 121
catggaacca gacagaaaag cg                                              22

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 122
gtcactggca gcaacagtct ta                                              22

<210> SEQ ID NO 123
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 123
tgggagccaa tattgtcttt gtgtt                                           25

<210> SEQ ID NO 124
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 124
aggaacgtac tggtgaaaac acc                                             23

<210> SEQ ID NO 125
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 125
ccctccccag tcctcatgta                                                 20

<210> SEQ ID NO 126
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 126
tcttcaaatg atttagtatt atttatggca aatacacaaa g                         41

<210> SEQ ID NO 127
<211> LENGTH: 41
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 127
tcttcaaatg atttagtatt atttatggca aatacacaaa g    41

<210> SEQ ID NO 128
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 128
tgtgtgacat gttctaatat agtcacat    28

<210> SEQ ID NO 129
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 129
tgtgtgacat gttctaatat agtcacat    28

<210> SEQ ID NO 130
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 130
tgtgtgacat gttctaatat agtcacat    28

<210> SEQ ID NO 131
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 131
tgtgtgacat gttctaatat agtcacat    28

<210> SEQ ID NO 132
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 132
tgtgtgacat gttctaatat agtcacat    28

<210> SEQ ID NO 133
<211> LENGTH: 28
<212> TYPE: DNA

<210> SEQ ID NO 133
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 133
tgtgtgacat gttctaatat agtcacat        28

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 134
ggtcctgcac cagtaatatg ca        22

<210> SEQ ID NO 135
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 135
gcaaatgact tgctattatt gatggcaaa        29

<210> SEQ ID NO 136
<211> LENGTH: 29
<212> TYPE: DNA
<213> ORGANISM: Artificial Sequence
<220> FEATURE:
<223> OTHER INFORMATION: Description of Artificial Sequence: Synthetic primer

<400> SEQUENCE: 136
gcaaatgact tgctattatt gatggcaaa        29

<210> SEQ ID NO 137
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 137
agtggttctg gattagctgg attg        24

<210> SEQ ID NO 138
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 138
gtggttctgg attagctgga ttgt        24

<210> SEQ ID NO 139
<211> LENGTH: 18
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 139
gcaaccagcc ctgtcgtc                                                  18

<210> SEQ ID NO 140
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 140 agacccagt tgcaaaccag                                                 20

<210> SEQ ID NO 141
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 141
ctggagtctt ccagtgtgat gatg                                           24

<210> SEQ ID NO 142
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 142
ctggagtctt ccagtgtgat gat                                            23

<210> SEQ ID NO 143
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 143
tgtgcagggt ggcaagt                                                   17

<210> SEQ ID NO 144
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 144
tgtgcagggt ggcaagt                                                   17

<210> SEQ ID NO 145
<211> LENGTH: 24
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 145
ctttcttgcg gagattctct tcct                                              24

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 146
cagacaactg ttcaaactg                                                    19

<210> SEQ ID NO 147
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 147
ctggcagcaa cagtct                                                       16

<210> SEQ ID NO 148
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 148
tagtggcacc agaatgg                                                      17

<210> SEQ ID NO 149
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 149
cccttcggct gcctcc                                                       16

<210> SEQ ID NO 150
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 150
cagcatgtca agatcac                                                      17

<210> SEQ ID NO 151
<211> LENGTH: 17
<212> TYPE: DNA
<213> ORGANISM: Artificial Sequence
<220> FEATURE:
<223> OTHER INFORMATION: Description of Artificial Sequence: Synthetic probe

<400> SEQUENCE: 151
ctggtccctc attgcac                                                    17

<210> SEQ ID NO 152
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 152
ccctccccag tcctca                                                     16

<210> SEQ ID NO 153
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 153
ccctccccag tcctca                                                     16

<210> SEQ ID NO 154
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 154
cctgctgaaa atgac                                                      15

<210> SEQ ID NO 155
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 155
cctgctgaaa atgac                                                      15

<210> SEQ ID NO 156
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 156
cctgctgaaa atgac                                                      15

<210> SEQ ID NO 157
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 157
cctgctgaaa atgac                                              15

<210> SEQ ID NO 158
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 158
cctgctgaaa atgac                                              15

<210> SEQ ID NO 159
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 159
cctgctgaaa atgac                                              15

<210> SEQ ID NO 160
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 160
tcgtccacaa aatgattc                                           18

<210> SEQ ID NO 161
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 161
ccttcgcctg tcctcatg                                           18

<210> SEQ ID NO 162
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 162
ccttcgcctg tcctcatg                                           18

<210> SEQ ID NO 163
<211> LENGTH: 14
<212> TYPE: DNA
<213> ORGANISM: Artificial Sequence
<220> FEATURE:
<223> OTHER INFORMATION: Description of Artificial Sequence: Synthetic
      probe
```

```
<400> SEQUENCE: 163
cagtgcgctt ttcc                                                        14

<210> SEQ ID NO 164
<211> LENGTH: 14
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 164
cagtgcgctt ttcc                                                        14

<210> SEQ ID NO 165
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 165
ctgctcacca tcgctatc                                                    18

<210> SEQ ID NO 166
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 166
cctcaggcgg ctcatag                                                     17

<210> SEQ ID NO 167
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 167
atgggcctcc ggttcat                                                     17

<210> SEQ ID NO 168
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 168
accggaggcc catcct                                                      16

<210> SEQ ID NO 169
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 169
```
cacactggaa gactcc                                              16

<210> SEQ ID NO 170
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 170
cacactggaa gactcc                                              16

<210> SEQ ID NO 171
<211> LENGTH: 15
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 171
ctgtgcgccg gtctc                                               15

<210> SEQ ID NO 172
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 172
gctacagaga aatctc                                              16

<210> SEQ ID NO 173
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 173
gagctgtggt agtggca                                             17

<210> SEQ ID NO 174
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 174
cactcagaga aggagc                                              16

<210> SEQ ID NO 175
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 175
catcacgcag ctcatg                                                      16

<210> SEQ ID NO 176
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 176
agtttggccc gcccaa                                                      16

<210> SEQ ID NO 177
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 177
ctcgacacag caggtca                                                     17

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 178
gcaggtcaag aggagtac                                                    18

<210> SEQ ID NO 179
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 179
gcaggtcaag aggagtac                                                    18

<210> SEQ ID NO 180
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 180
cgccactagc tcca                                                        14

<210> SEQ ID NO 181
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ccacgagctc caacta                                                      16

<210> SEQ ID NO 182
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 182
acgccaccag ctcc                                                       14

<210> SEQ ID NO 183
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 183
cgccatcagc tcc                                                        13

<210> SEQ ID NO 184
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 184
cgccagcagc tcc                                                        13

<210> SEQ ID NO 185
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 185
cgccaccagc tcca                                                       14

<210> SEQ ID NO 186
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 186
gctggtgacg taggc                                                      15

<210> SEQ ID NO 187
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187
gctggaaaag aagagtac                                                   18

<210> SEQ ID NO 188
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188
cagctggaca agaagag                                                    17

<210> SEQ ID NO 189
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
ttggagcaga tggtgtt                                                    17

<210> SEQ ID NO 190
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190
tggagcaggt gatgtt                                                     16

<210> SEQ ID NO 191
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191
tgaggcactg ccc                                                        13

<210> SEQ ID NO 192
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192
gaaacacttt tcgacatagt gtggtg                                          26

<210> SEQ ID NO 193
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
tgtgtaacag tgcctgcatg                                                 20

<210> SEQ ID NO 194
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 194
gcatgggcag catg                                                          14

<210> SEQ ID NO 195
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 195
gcatgaaccg gaggc                                                         15

<210> SEQ ID NO 196
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 196
catgaaccag aggcc                                                         15

<210> SEQ ID NO 197
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 197
ttgaggtgcg tgtttgtg                                                      18

<210> SEQ ID NO 198
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 198
gctacagtga aatctc                                                        16

<210> SEQ ID NO 199
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 199
agctgtggca gtggca                                                        16

<210> SEQ ID NO 200

<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 200
cactcagaaa aggagc                                                      16

<210> SEQ ID NO 201
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 201
tcatcatgca gctcatg                                                     17

<210> SEQ ID NO 202
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 202
agtttggcca gcccaa                                                      16

<210> SEQ ID NO 203
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 203
ctcgacacag gaggtca                                                     17

<210> SEQ ID NO 204
<211> LENGTH: 17
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 204
caggtcacga ggagtac                                                     17

<210> SEQ ID NO 205
<211> LENGTH: 18
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 205
gcaggtcatg aggagtac                                                    18

<210> SEQ ID NO 206
<211> LENGTH: 13

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
cgccaccagc tcc                                                          13

<210> SEQ ID NO 207
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
ccaccagctc caacta                                                       16

<210> SEQ ID NO 208
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
acgccacaag ctccaa                                                       16

<210> SEQ ID NO 209
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
cgccaccagc tcc                                                          13

<210> SEQ ID NO 210
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
cgccaccagc tcc                                                          13

<210> SEQ ID NO 211
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211
cgccaacagc tccaa                                                        15

<210> SEQ ID NO 212
<211> LENGTH: 15
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 212
gctggtggcg taggc                                                    15

<210> SEQ ID NO 213
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213
gctggacaag aagagtac                                                 18

<210> SEQ ID NO 214
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214
cagctggaca tgaagag                                                  17

<210> SEQ ID NO 215
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215
tggagcaggt ggtgtt                                                   16

<210> SEQ ID NO 216
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 216
tggagcaggt ggtgtt                                                   16

<210> SEQ ID NO 217
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 217
tgaggcgctg ccc                                                      13

<210> SEQ ID NO 218
<211> LENGTH: 27
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 218
agaaacactt tttgacatag tgtggtg                                            27

<210> SEQ ID NO 219
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 219
atgtgtaaca gttcctgcat g                                                  21

<210> SEQ ID NO 220
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 220
gcatgggcgg catg                                                          14

<210> SEQ ID NO 221
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 221
gcatgaactg gaggcc                                                        16

<210> SEQ ID NO 222
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222
catgaaccgg aggcc                                                         15

<210> SEQ ID NO 223
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223
tttgaggtgt gtgtttgtgc                                                    20
```

METHODS, COMPOSITIONS, AND KITS FOR DETECTING ALLELIC VARIANTS

CROSS REFERENCE TO RELATED APPLICATIONS

The present application is a continuation of U.S. patent application Ser. No. 15/923,954 filed Mar. 16, 2018, which is a divisional of U.S. patent application Ser. No. 14/879,156 filed Oct. 9, 2015, now abandoned, which is a divisional of U.S. patent application Ser. No. 12/641,321 filed Dec. 17, 2009, now U.S. Pat. No. 9,534,255, which claims the benefit of priority under 35 U.S.C. 119 to U.S. Provisional Application Ser. No. 61/258,582 filed Nov. 5, 2009; U.S. Provisional Application Ser. No. 61/253,501 filed Oct. 20, 2009; U.S. Provisional Application Ser. No. 61/251,623 filed Oct. 14, 2009; U.S. Provisional Application Ser. No. 61/186,775 filed Jun. 12, 2009; U.S. Provisional Application Ser. No. 61/164,230 filed Mar. 27, 2009; and U.S. Provisional Application Ser. No. 61/138,521 filed Dec. 17, 2008, all of which are incorporated herein by reference in their entireties.

BACKGROUND

Single nucleotide polymorphisms (SN Ps) are the most common type of genetic diversity in the human genome, occurring at a frequency of about one SNP in 1,000 nucleotides or less in human genomic DNA (Kwok, P-Y, Ann Rev Genom Hum Genet 2001, 2: 235-258). SNPs have been implicated in genetic disorders, susceptibility to different diseases, predisposition to adverse reactions to drugs, and for use in forensic investigations. Thus, SNP (or rare mutation) detection provides great potentials in diagnosing early phase diseases, such as detecting circulating tumor cells in blood, for prenatal diagnostics, as well as for detection of disease-associated mutations in a mixed cell population.

Numerous approaches for SNP genotyping have been developed based on methods involving hybridization, ligation, or DNA polymerases (Chen, X., and Sullivan, P F, The Pharmacogeonomics Journal 2003, 3, 77-96.). For example, allele-specific polymerase chain reaction (AS-PCR) is a widely used strategy for detecting DNA sequence variation (VVu D Y, Ugozzoli L, Pal B K, Wallace R B., Proc Natl Acad Sci USA 1989; 86:2757-2760). AS-PCR, as its name implies, is a PCR-based method whereby one or both primers are designed to anneal at sites of sequence variations which allows for the ability to differentiate among different alleles of the same gene. AS-PCR exploits the fidelity of DNA polymerases, which extend primers with a mismatched 3' base at much lower efficiency, from 100 to 100,000 fold less efficient, than that with a matched 3' base (Chen, X., and Sullivan, P F, The Pharmacogeonomics Journal 2003; 3:77-96). The difficulty in extending mismatched primers results in diminished PCR amplification that can be readily detected.

The specificity and selectivity of AS-PCR, however, is largely dependent on the nature of exponential amplification of PCR which makes the decay of allele discriminating power rapid. Even though primers are designed to match a specific variant to selectively amplify only that variant, in actuality significant mismatched amplification often occurs. Moreover, the ability of AS-PCR to differentiate between allelic variants can be influenced by the type of mutation or the sequence surrounding the mutation or SNP (Ayyadevara S, Thaden J J, Shmookler Reis R J., Anal Biochem 2000; 284:11-18), the amount of allelic variants present in the sample, as well as the ratio between alternative alleles. Collectively, these factors are often responsible for the frequent appearance of false-positive results, leading many researchers to attempt to increase the reliability of AS-PCR (Orou A, Fechner B, Utermann G, Menzel H J., Hum Mutat 1995; 6:163-169)(lmyanitov E N, Buslov K G, Suspitsin E N, Kuligina E S, Belogubova E V, Grigoriev M Y, et al., Biotechniques 2002; 33:484-490)(McKinzie P B, Parsons B L. Detection of rare K-ras codon 12 mutations using allele-specific competitive blocker PCR. Mutat Res 2002; 517: 209-220)(Latorra D, Campbell K, Wolter A, Hurley J M., Hum Mutat 2003; 22:79-85).

In some cases, the selectivity of AS-PCR has been increased anywhere from detection of 1 in 10 alleles to 1 in 100,000 alleles by using SNP-based PCR primers containing locked nucleic acids (LNAs) (Latorra, D., et al., Hum Mut 2003, 2:79-85; Nakiandwe, J. et al., Plant Method 2007, 3:2) or modified bases (Koizumi, M. et al. Anal Biochem. 2005, 340:287-294). However, these base "mimics" or modifications increase the overall cost of analysis and often require extensive optimization.

Another technology involving probe hybridization methods used for discriminating allelic variations is TaqMan® genotyping. However, like AS-PCR, selectivity using this method is limited and not suitable for detecting rare (1 in ≥1,000) alleles or mutations in a mixed sample.

SUMMARY

In some embodiments, the present inventions relates generally to compositions, methods and kits for use in discriminating sequence variation between different alleles. More specifically, in some embodiments, the present invention provides for compositions, methods and kits for quantitating rare (e.g., mutant) allelic variants, such as SNPs, or nucleotide (NT) insertions or deletions, in samples comprising abundant (e.g., wild type) allelic variants with high specificity. In particular, in some embodiments, the invention relates to a highly selective method for mutation detection referred to as competitive allele-specific TaqMan PCR ("cast-PCR").

In one aspect, the present invention provides compositions for use in identifying and/or quantitating allelic variants in nucleic acid samples. Some of these compositions can comprise: (a) an allele-specific primer; (b) an allele-specific blocker probe; (c) a detector probe; and/or (d) a locus-specific primer.

In some embodiments of the compositions, the allele-specific primer comprises a target-specific portion and an allele-specific nucleotide portion. In some embodiments, the allele-specific primer may further comprise a tail. In some exemplary embodiments, the tail is located at the 5' end of the allele-specific primer. In other embodiments, the tail of the allele-specific primer has repeated guanine and cytosine residues ("GC-rich"). In some embodiments, the melting temperature ("Tm") of the entire allele-specific primer ranges from about 50° C. to 66° C. In some embodiments, the allele-specific primer concentration is between about 20-900 nM.

In some embodiments of the compositions, the allele-specific nucleotide portion of the allele-specific primer is located at the 3' terminus. In some embodiments, the selection of the allele-specific nucleotide portion of the allele-specific primer involves the use of a highly discriminating base (e.g., for detection of A/A, A/G, G/A, G/G, A/C, or C/A alleles). In some embodiments, for example when the allele to be detected involves A/G or C/T SNPs, A or G is used as the 3' allele-specific nucleotide portion of the allele-specific primer (e.g., if A or T is the target allele), or C or T is used as the 3' allele-specific nucleotide portion of the allele-specific primer (e.g., if C or G is the target allele). In other embodiments, A is used as the discriminating base at the 3' end of the allele-specific primer when detecting and/or quantifying A/T SNPs. In other embodiments, G is used as the discriminating base at the 3' end of the allele-specific primer when detecting and/or quantifying C/G SNPs.

In some embodiments of the compositions, the allele-specific blocker probe comprises a non-extendable blocker moiety at the 3' terminus. In some exemplary embodiments, the non-extendable blocker moiety is a minor groove binder (MGB). In some embodiments, the target allele position is located about 6-10, such as about 6, about 7, about 8, about 9, or about 10 nucleotides away from the non-extendable blocker moiety of the allele-specific blocker probe. In some embodiments, the allele-specific blocker probe comprises an MGB moiety at the 5' terminus. In some exemplary embodiments, the allele-specific blocker probe is not cleaved during PCR amplification. In some embodiments, the Tm of the allele-specific blocker probe ranges from about 60° C. to 66° C.

In some embodiments of the compositions, the allele-specific blocker probe and/or allele-specific primer comprise at least one modified base. In some embodiments, the modified base(s) may increase the difference in the Tm between matched and mismatched target sequences and/or decrease mismatch priming efficiency, thereby improving not only assay specificity bust also selectivity. Such modified base(s) may include, for example, 8-Aza-7-deaza-dA (ppA), 8-Aza-7-deaza-dG (ppG), locked nucleic acid (LNA) or 2'-O,4'-C-ethylene nucleic acid (ENA) bases (FIG. 4B).

In some embodiments of the compositions, the detector probe is a sequence-based or locus-specific detector probe. In other embodiments the detector probe is a 5' nuclease probe. In some exemplary embodiments, the detector probe can comprises an MGB moiety, a reporter moiety (e.g., FAM™, TET™, JOE™, VIC™, or SYBR® Green), a quencher moiety (e.g., Black Hole Quencher™ or TAMRA™;), and/or a passive reference (e.g., ROX™). In some exemplary embodiments, the detector probe is designed according to the methods and principles described in U.S. Pat. No. 6,727,356 (the disclosure of which is incorporated herein by reference in its entirety). In some exemplary embodiments, the detector probe is a TaqMan® probe (Applied Biosystems, Foster City).

In some embodiments of the compositions, the composition can further comprise a polymerase; deoxyribonucleotide triphosphates (dNTPs); other reagents and/or buffers suitable for amplification; and/or a template sequence or nucleic acid sample. In some embodiments, the polymerase can be a DNA polymerase. In some other embodiments, the polymerase can be thermostable, such as Taq DNA polymerase. In other embodiments, the template sequence or nucleic acid sample can be DNA, such as genomic DNA (gDNA) or complementary DNA (cDNA). In other embodiments the template sequence or nucleic acid sample can be RNA, such as messenger RNA (mRNA).

In another aspect, the present disclosure provides methods for amplifying an allele-specific sequence. Some of these methods can include one or more of the following: (a) hybridizing an allele-specific primer to a first nucleic acid molecule comprising a first allele (allele-1); (b) hybridizing an allele-specific blocker probe to a second nucleic acid molecule comprising a second allele (allele-2), wherein allele-2 corresponds to the same loci as allele-1; (c) hybridizing a detector probe to the first nucleic acid molecule; (d) hybridizing a locus-specific primer to the extension product of the allele-specific primer; and (e) PCR amplifying the first nucleic acid molecule comprising allele-1.

In another aspect, the present invention provides methods for detecting and/or quantitating an allelic variant in a pooled or mixed sample comprising other alleles. Some of these methods can include one or more of the following: (a) in a first reaction mixture hybridizing a first allele-specific primer to a first nucleic acid molecule comprising a first allele (allele-1) and in a second reaction mixture hybridizing a second allele-specific primer to a first nucleic acid molecule comprising a second allele (allele-2), wherein allele-2 corresponds to the same loci as allele-1; (b) in the first reaction mixture hybridizing a first allele-specific blocker probe to a second nucleic acid molecule comprising allele-2 and in the second reaction mixture hybridizing a second allele-specific blocker probe to a second nucleic acid molecule comprising allele-1; (c) in the first reaction mixture, hybridizing a first detector probe to the first nucleic acid molecule and in the second reaction mixture and hybridizing a second detector probe to the first nucleic acid molecule; (d) in the first reaction mixture hybridizing a first locus-specific primer to the extension product of the first allele-specific primer and in the second reaction mixture hybridizing a second locus-specific primer to the extension product of the second allele-specific primer; and (e) PCR amplifying the first nucleic acid molecule to form a first set or sample of amplicons and PCR amplifying the second nucleic acid molecule to form a second set or sample of amplicons; and (f) comparing the first set of amplicons to the second set of amplicons to quantitate allele-1 in the sample comprising allele-2 and/or allele-2 in the sample comprising allele-1.

In some embodiments of the methods, the first and/or second allele-specific primer comprises a target-specific portion and an allele-specific nucleotide portion. In some embodiments, the first and/or second allele-specific primer may further comprise a tail. In some embodiments, the Tm of the entire first and/or second allele-specific primer ranges from about 50° C. to 66° C. In some embodiments the first and/or second allele-specific primer concentration is between about 20-900 nM.

In some embodiments of the methods, the target-specific portion of the first allele-specific primer and the target-specific portion of the second allele-specific primer comprise the same sequence. In other embodiments, the target-specific portion of the first allele-specific primer and the target-specific portion of the second allele-specific primer are the same sequence.

In some embodiments of the methods, the tail is located at the 5'-end of the first and/or second allele-specific primer. In some embodiments, the 5' tail of the first allele-specific primer and the 5' tail of the second allele-specific primer comprise the same sequence. In other embodiments, the 5' tail of the first allele-specific primer and the 5' tail of the second allele-specific primer are the same sequence. In other embodiments, the tail of the first and/or second allele-specific primer is GC-rich.

In some embodiments of the methods, the allele-specific nucleotide portion of the first allele-specific primer is specific to a first allele (allele-1) of a SNP and the allele-specific nucleotide portion of the second allele-specific primer is specific to a second allele (allele-2) of the same SNP. In some embodiments of the methods, the allele-specific nucleotide portion of the first and/or second allele-specific primer is located at the 3'-terminus. In some embodiments, the selection of the allele-specific nucleotide portion of the first and/or second allele-specific primer involves the use of a highly discriminating base (e.g., for detection of A/A, A/G, G/A, G/G, A/C, or C/A alleles). In some embodiments, for example when the allele to be detected involves A/G or C/T SNPs, A or G is used as the 3' allele-specific nucleotide portion of the first and/or second allele-specific primer (e.g., if A/T is the target allele), or C or T is used as the 3' allele-specific nucleotide portion of the first and/or second allele-specific primer (e.g., if C/G is the target allele). In other embodiments, A is used as the discriminating base at the 3' end of the first and/or second allele-specific primer when detecting and/or quantifying A/T SNPs. In other embodiments, G is used as the discriminating base at the 3' end of the first and/or second allele-specific primer when detecting and/or quantifying C/G SNPs.

In some embodiments of the methods, the first and/or second allele-specific blocker probe comprises a non-extendable blocker moiety at the 3' terminus. In some exemplary embodiments, the non-extendable blocker moiety is an MGB. In some embodiments, the target allele position is located about 6-10, such as about 6, about 7, about 8, about 9, or about 10 nucleotides away from the non-extendable blocker moiety of the first and/or second allele-specific blocker probe. In some embodiments, the first and/or second allele-specific blocker probe comprises an MGB moiety at the 5'-terminus. In other embodiments, the first and/or second allele-specific blocker probe is not cleaved during PCR amplification. In some embodiments, the Tm of the first and/or second allele-specific blocker probe ranges from about 60° C. to 66° C.

In some embodiments of the methods, the first and/or second allele-specific blocker probe and/or the first and/or second allele-specific primer comprises at least one modified base. In some embodiments, the modified base(s) may increase the difference in the Tm between matched and mismatched target sequences and/or decrease mismatch priming efficiency, thereby improving not only assay specificity bust also selectivity. Such modified base(s) may include, for example, 8-Aza-7-deaza-dA (ppA), 8-Aza-7-deaza-dG (ppG), locked nucleic acid (LNA) or 2'-O,4'-C-ethylene nucleic acid (ENA) bases (FIG. 4B).

In some embodiments of the methods, the first and/or second detector probes are the same. In some embodiments, the first and/or second detector probes are different. In some embodiments, the first and/or second detector probe is a sequence-based or locus-specific detector probe. In other embodiments the first and/or second detector probe is a 5' nuclease probe. In some exemplary embodiments, the first and/or second detector probes comprises an MGB moiety, a reporter moiety (e.g., FAM™, TET™, JOE™, VIC™, or SYBR® Green), a quencher moiety (e.g., Black Hole Quencher™ or TAMRA™;), and/or a passive reference (e.g., ROX™). In some exemplary embodiments, the first and/or second detector probe is designed according to the methods and principles described in U.S. Pat. No. 6,727,356 (the disclosure of which is incorporated herein by reference in its entirety). In some exemplary embodiments, the detector probe is a TaqMan® probe.

In some embodiments of the methods, the first locus-specific primer and the second locus-specific primer comprise the same sequence. In some embodiments the first locus-specific primer and the second locus-specific primer are the same sequence.

In some embodiments of the methods, the first and/or second reaction mixtures can further comprises a polymerase; dNTPs; other reagents and/or buffers suitable for PCR amplification; and/or a template sequence or nucleic acid sample. In some embodiments, the polymerase can be a DNA polymerase. In some embodiments, the polymerase can be thermostable, such as Taq DNA polymerase. In some embodiments, the template sequence or nucleic acid sample can be DNA, such as gDNA or cDNA. In other embodiments the template sequence or nucleic acid sample can be RNA, such as mRNA.

In some embodiments of the methods, the first allele-specific blocker probe binds to the same strand or sequence as the second allele-specific primer, while the second allele-specific blocker probe binds to the same strand or sequence as the first allele-specific primer. In some embodiments, the first and/or second allele-specific blocker probes are used to reduce the amount of background signal generated from either the second allele and/or the first allele, respectively. In some embodiments, first and/or second allele-specific blocker probes are non-extendable and preferentially anneal to either the second allele or the first allele, respectively, thereby blocking the annealing of, for example, the extendable first allele-specific primer to the second allele and/or the extendable second allele-specific primer to first allele.

In some exemplary embodiments, the first allele is a rare (e.g., minor) or mutant allele. In other exemplary embodiments the second allele is an abundant (e.g., major) or wild type allele.

In another aspect, the present invention provides kits for quantitating a first allelic variant in a sample comprising a second allelic variant involving: (a) a first allele-specific primer; (b) a second allele-specific primer; (c), a first locus-specific primer; (d) a second locus-specific primer; (e) a first allele-specific blocker probe; (f) a second allele-specific blocker probe; and (g) a first locus-specific detector probe and (h) a second locus-specific detector probe.

In some embodiments of the kits, the first and/or second allele-specific primer comprises a target-specific portion and an allele-specific nucleotide portion. In some embodiments, the first and/or second allele-specific primer may further comprise a tail. In some embodiments, the Tm of the entire first and/or second allele-specific primer ranges from about 50° C. to 66° C. In some embodiments the first and/or second allele-specific primer concentrations are between about 20-900 nM.

In some embodiments of the kits, the target-specific portion of the first allele-specific primer and the target-specific portion of the second allele-specific primer comprise the same sequence. In other embodiments, the target-specific portion of the first allele-specific primer and the target-specific portion of the second allele-specific primer are the same sequence.

In some embodiments of the kits, the tail is located at the 5' end of the first and/or second allele-specific primer. In some embodiments, the 5' tail of the first allele-specific primer and the 5' tail of the second allele-specific primer comprise the same sequence. In other embodiments, the 5' tail of the first allele-specific primer and the 5' tail of the second allele-specific primer are the same sequence. In other embodiments, the tail of the first and/or second allele-specific primer is GC rich.

In some embodiments of the kits, the allele-specific nucleotide portion of the first allele-specific primer is specific to a first allele (allele-1) of a SNP and the allele-specific nucleotide portion of the second allele-specific primer is specific to a second allele (allele-2) of the same SNP. In some embodiments of the disclosed methods, the allele-specific nucleotide portion of the first and/or second allele-specific primer is located at the 3' terminus. In some embodiments, the selection of the allele-specific nucleotide portion of the first and/or second allele-specific primer involves the use of a highly discriminating base (e.g., for detection of A/A, A/G, G/A, G/G, A/C, or C/A alleles) (FIG. 2). In some embodiments, for example when the allele to be detected involves A/G or C/T SNPs, A or G is used as the 3' allele-specific nucleotide portion of the first and/or second allele-specific primer (e.g., if A/T is the target allele), or C or T is used as the 3' allele-specific nucleotide portion of the first and/or second allele-specific primer (e.g., if C/G is the target allele). In other embodiments, A is used as the discriminating base at the 3' end of the first and/or second allele-specific primer when detecting and/or quantifying A/T SNPs. In other embodiments, G is used as the discriminating base at the 3' end of the first and/or second allele-specific primer when detecting and/or quantifying C/G SNPs.

In some embodiments of the kits, the first and/or second allele-specific blocker probe comprises a non-extendable blocker moiety at the 3' terminus. In some exemplary embodiments, the non-extendable blocker moiety is an MGB. In some embodiments, the target allele position is located about 6-10, such as about 6, about 7, about 8, about 9, or about 10 nucleotides away from the non-extendable blocker moiety of the first and/or second allele-specific blocker probe. In some embodiments, the first and/or second allele-specific blocker probe comprises an MGB moiety at the 5' terminus. In other embodiments, the first and/or second allele-specific blocker probe is not cleaved during PCR amplification. In some embodiments, the Tm of the first and/or second allele-specific blocker probe ranges from about 60° C. to 66° C.

In some embodiments of the kits, the allele-specific blocker probe and/or the first and/or second allele-specific primer comprises at least one modified base. In some embodiments, the modified base(s) may increase the difference in the Tm between matched and mismatched target sequences and/or decrease mismatch priming efficiency, thereby improving not only assay specificity bust also selectivity. Such modified base(s) may include, for example, 8-Aza-7-deaza-dA (ppA), 8-Aza-7-deaza-dG (ppG), locked nucleic acid (LNA) or 2'-O,4'-C-ethylene nucleic acid (ENA) bases (FIG. 4B).

In some embodiments of the kits, the first and/or second detector probes are the same. In some embodiments of the disclosed kits the first and/or second detector probes are different. In some embodiments of the disclosed kits, the first and/or second detector probes are sequence-based or locus-specific detector probes. In other embodiments the first and/or second detector probe are 5' nuclease probes. In some exemplary embodiments, the first and/or second detector probes comprise an MGB moiety, a reporter moiety (e.g., FAM™, TET™, JOE™, VIC™, or SYBR® Green), a quencher moiety (e.g., Black Hole Quencher™ or TAMRA™;), and/or a passive reference (e.g., ROX™). In some exemplary embodiments, the first and/or second detector probe are designed according to the methods and principles described in U.S. Pat. No. 6,727,356 (the disclosure of which is incorporated herein by reference in its entirety). In some exemplary embodiments, the detector probe is a TaqMan® probe.

In some embodiments of the kits, the first locus-specific primer and the second locus-specific primer comprise the same sequence. In some embodiments the first locus-specific primer and the second locus-specific primer are the same sequence.

In some embodiments of the kits, the first and/or second reaction mixture can further comprise a polymerase; dNTPs; other reagents and/or buffers suitable for PCR amplification; and/or a template sequence or nucleic acid sample. In some embodiments, the polymerase can be a DNA polymerase. In some other embodiments, the polymerase can be thermostable, such as Taq DNA polymerase.

In some embodiments, the compositions, methods and kits of the present invention provide high allelic discrimination specificity and selectivity. In some embodiments, the quantitative determination of specificity and/or selectivity comprises a comparison of Ct values between a first set of amplicons and a second set of amplicons. In some embodiments, selectivity is at a level whereby a single copy of a given allele in about 1 million copies of another allele or alleles can be detected.

The foregoing has described various embodiments of the invention that provide improved detection and discrimination of allelic variants using one or more of the following: (a) tailed allele-specific primers; (b) low allele-specific primer concentration; (c) allele-specific primers designed to have lower Tms; (d) allele-specific primers designed to target discriminating bases; (e) allele-specific blocker probes containing MGB, designed to prevent amplification from alternative, and potentially more abundant, allelic variants in a sample; and (f) allele-specific blocker probes and/or allele-specific primers designed to comprise modified bases in order to increase the delta Tm between matched and mismatched target sequences.

While particular embodiments employing several of the above improvements have been discussed herein, it will be apparent to the skilled artisan that depending on the nature of the sample to be examined, various combinations of the above improvements can be combined to arrive at a favorable result. Thus, for example, non-MGB blocker probes can be used with an embodiment that include methods employing allele-specific primers containing modified bases to increase delta Tm; such primers can also be designed to target discriminating bases; and the primers can be used at low primer concentrations. Accordingly, alternative embodiments based upon the present disclosure can be used to achieve a suitable level of allelic detection.

The present disclosure provides the advantage that any of the combinations of listed improvements could be utilized by a skilled artisan in a particular situation. For example, the current invention can include a method or reaction mixture that employs improvements a, c, d and f; improvements b, c, and e; or improvements It is to be understood that both the foregoing general description and the following detailed description are exemplary and explanatory only and are not restrictive of the invention, as claimed.

The accompanying drawings, which are incorporated in and constitute a part of this specification, illustrate several exemplary embodiments of the disclosure and together with the description, serve to explain certain teachings.

BRIEF DESCRIPTION OF THE DRAWINGS

The skilled artisan will understand that the drawings described below are for illustration purposes only. The drawings are not intended to limit the scope of the present teachings in any way.

FIG. 2 depicts a schematic of an illustrative embodiment of cast-PCR using allele-specific blocker probes comprising highly discriminating bases for detecting rare allelic variants. Highly discriminating bases may include, for example, A/A, A/G, G/A, G/G, A/C, C/A. The least discriminating bases may include, for example, C/C, T/C, G/T, T/G, C/T. In some embodiments, for example, for detection of A-G or C-T SNPs, A & G are used as the discriminating base if A//T is allelic variant (e.g., mutant allele); or C & T are used as the discriminating base if C//G allelic variant (e.g., mutant allele).

FIG. 6 depicts the sequence of KRAS mutations at codons 12 and 13 that are detectable using cast-PCR methods. KRAS mutations at codons 12 and 13 are associated with resistance to cetuxima or panitumumab in metastatic colorectal cancer (Di Nicolantonio F., et al., J Clin Oncol. 2008; 26:5705-12.)

FIGS. 7A-7C depict the specificity of KRAS mutation detection using cast-PCR assays in one exemplary embodiment.

FIG. 10 depicts a number of different tumor markers (SNPs) detected in tumor samples using one exemplary embodiment of cast-PCR.

FIGS. 11A-11D show a list of exemplary allele-specific primers and probes used in cast-PCR assays.

DETAILED DESCRIPTION

I. Introduction

Figure 1:
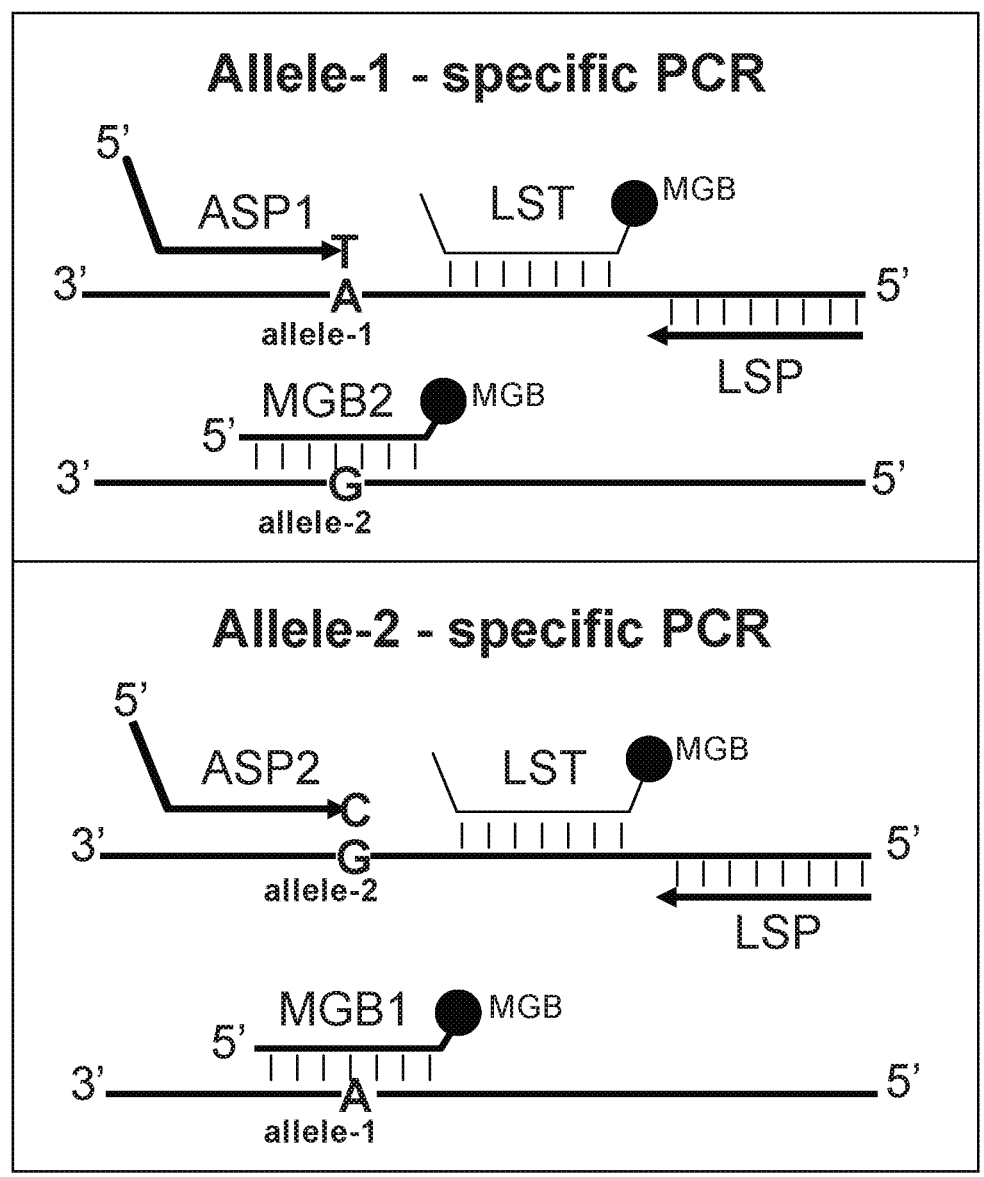
FIG. 1 depicts a schematic of an illustrative embodiment of cast-PCR. In some embodiments, components of cast-PCR include the following: one locus-specific TaqMan probe (LST); two MGB blockers: one allele-1-specific MGB blocker (MGB1) and one allele-2-specific MGB blocker (MGB2); 3 PCR primers: one locus-specific PCR primer (LSP); one allele-1-specific primer (ASP1) and one allele-2-specific primer (ASP2).

The selective amplification of an allele of interest is often complicated by factors including the mispriming and extension of a mismatched allele-specific primer on an alternative allele. Such mispriming and extension can be especially problematic in the detection of rare alleles present in a sample populated by an excess of another allelic variant. When in sufficient excess, the mispriming and extension of the other allelic variant may obscure the detection of the allele of interest. When using PCR-based methods, the discrimination of a particular allele in a sample containing alternative allelic variants relies on the selective amplification of an allele of interest, while minimizing or preventing amplification of other alleles present in the sample.

A number of factors have been identified, which alone or in combination, contribute to the enhanced discriminating power of allele-specific PCR. As disclosed herein, a factor which provides a greater delta Ct value between a mismatched and matched allele-specific primer is indicative of greater discriminating power between allelic variants. Such factors found to improve discrimination of allelic variants using the present methods include, for example, the use of one or more of the following: (a) tailed allele-specific primers; (b) low allele-specific primer concentration; (c) allele-specific primers designed to have lower Tms; (d) allele-specific primers designed to target discriminating bases; (e) allele-specific blocker probes designed to prevent amplification from alternative, and potentially more abundant, allelic variants in a sample; and (f) allele-specific blocker probes and/or allele-specific primers designed to comprise modified bases in order to increase the delta Tm between matched and mismatched target sequences.

The above-mentioned factors, especially when used in combination, can influence the ability of allele-specific PCR to discriminate between different alleles present in a sample. Thus, the present disclosure relates generally to novel amplification methods referred to as cast-PCR, which utilizes a combination of factors referred to above to improve discrimination of allelic variants during PCR by increasing delta Ct values. In some embodiments, the present methods can involve high levels of selectivity, wherein one mutant molecule in a background of at least 1,000 to 1,000,000, such as about 1000-10,000, about 10,000 to 100,000, or about 100,000 to 1,000,000 wild type molecules, or any fractional ranges in between can be detected. In some embodiments, the comparison of a first set of amplicons and a second set of amplicons involving the disclosed methods provides improvements in specificity from 1,000× to 1,000,000× fold difference, such as about 1000-10,000×, about 10,000 to 100,000×, or about 100,000 to 1,000,000× fold difference, or any fractional ranges in between.

II. Definitions

For the purposes of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended.

As used herein, the term "allele" refers generally to alternative DNA sequences at the same physical locus on a segment of DNA, such as, for example, on homologous chromosomes. An allele can refer to DNA sequences which differ between the same physical locus found on homologous chromosomes within a single cell or organism or which differ at the same physical locus in multiple cells or organisms ("allelelic variant"). In some instances, an allele can correspond to a single nucleotide difference at a particular physical locus. In other embodiments and allele can correspond to nucleotide (single or multiple) insertion or deletion.

As used herein, the term "allele-specific primer" refers to an oligonucleotide sequence that hybridizes to a sequence comprising an allele of interest, and which when used in PCR can be extended to effectuate first strand cDNA synthesis. Allele-specific primers are specific for a particular allele of a given target DNA or loci and can be designed to detect a difference of as little as one nucleotide in the target sequence. Allele-specific primers may comprise an allele-specific nucleotide portion, a target-specific portion, and/or a tail.

As used herein, the terms "allele-specific nucleotide portion" or "allele-specific target nucleotide" refers to a nucleotide or nucleotides in an allele-specific primer that can selectively hybridize and be extended from one allele (for example, a minor or mutant allele) at a given locus to the exclusion of the other (for example, the corresponding major or wild type allele) at the same locus.

As used herein, the term "target-specific portion" refers to the region of an allele-specific primer that hybridizes to a target polynucleotide sequence. In some embodiments, the target-specific portion of the allele-specific primer is the priming segment that is complementary to the target sequence at a priming region 5' of the allelic variant to be detected. The target-specific portion of the allele-specific primer may comprise the allele-specific nucleotide portion. In other instances, the target-specific portion of the allele-specific primer is adjacent to the 3' allele-specific nucleotide portion.

As used herein, the terms "tail" or "5'-tail" refers to the non-3' end of a primer. This region typically will, although does not have to contain a sequence that is not complementary to the target polynucleotide sequence to be analyzed. The 5' tail can be any of about 2-30, 2-5, 4-6, 5-8, 6-12, 7-15, 10-20, 15-25 or 20-30 nucleotides, or any range in between, in length.

As used herein, the term "allele-specific blocker probe" (also referred to herein as "blocker probe," "blocker,") refers to an oligonucleotide sequence that binds to a strand of DNA comprising a particular allelic variant which is located on the same, opposite or complementary strand as that bound by an allelic-specific primer, and reduces or prevents amplification of that particular allelic variant. As discussed in greater detail herein, allele-specific blocker probes generally comprise modifications, e.g., at the 3'-OH of the ribose ring, which prevent primer extension by a polymerase. The allele-specific blocker probe can be designed to anneal to the same or opposing strand of what the allele-specific primer anneals to and can be modified with a blocking group (e.g., a "non-extendable blocker moiety") at its 3' terminal end. Thus, a blocker probe can be designed, for example, so as to tightly bind to a wild type allele (e.g., abundant allelic variant) in order to suppress amplification of the wild type allele while amplification is allowed to occur on the same or opposing strand comprising a mutant allele (e.g., rare allelic variant) by extension of an allele-specific primer. In illustrative examples, the allele-specific blocker probes do not include a label, such as a fluorescent, radioactive, or chemiluminescent label As used herein, the term "non-extendable blocker moiety" refers generally to a modification on an oligonucleotide sequence such as a probe and/or primer which renders it incapable of extension by a polymerase, for example, when hybridized to its complementary sequence in a PCR reaction. Common examples of blocker moieties include modifications of the ribose ring 3'-OH of the oligonucleotide, which prevents addition of further bases to the 3'-end of the oligonucleotide sequence a polymerase. Such 3'-OH modifications are well known in the art. (See, e.g., Josefsen, M., et al., *Molecular and Cellular Probes*, 23 (2009):201-223; McKinzie, P. et al., *Mutagenesis*. 2006, 21(6):391-7; Parsons, B. et al., *Methods Mol Biol.* 2005, 291:235-45; Parsons, B. et al., *Nucleic Acids Res.* 1992, 25:20(10):2493-6; and Morlan, J. et al., *PLoS One* 2009, 4 (2): e4584, the disclosures of which are incorporated herein by reference in their entireties.)

As used herein, the terms "MGB," "MGB group," "MGB compound," or "MBG moiety" refers to a minor groove binder. When conjugated to the 3' end of an oligonucleotide, an MGB group can function as a non-extendable blocker moiety.

An MGB is a molecule that binds within the minor groove of double stranded DNA. Although a general chemical formula for all known MGB compounds cannot be provided because such compounds have widely varying chemical structures, compounds which are capable of binding in the minor groove of DNA, generally speaking, have a crescent shape three dimensional structure. Most MGB moieties have a strong preference for A-T (adenine and thymine) rich regions of the B form of double stranded DNA. Nevertheless, MGB compounds which would show preference to C-G (cytosine and guanine) rich regions are also theoretically possible. Therefore, oligonucleotides comprising a radical or moiety derived from minor groove binder molecules having preference for C-G regions are also within the scope of the present invention.

Some MGBs are capable of binding within the minor groove of double stranded DNA with an association constant of $10^3 M^{-1}$ or greater. This type of binding can be detected by well established spectrophotometric methods such as ultraviolet (UV) and nuclear magnetic resonance (NMR) spectroscopy and also by gel electrophoresis. Shifts in UV spectra upon binding of a minor groove binder molecule and NMR spectroscopy utilizing the "Nuclear Overhauser" (NOSEY) effect are particularly well known and useful techniques for this purpose. Gel electrophoresis detects binding of an MGB to double stranded DNA or fragment thereof, because upon such binding the mobility of the double stranded DNA changes.

A variety of suitable minor groove binders have been described in the literature. See, for example, Kutyavin, et al. U.S. Pat. No. 5,801,155; Wemmer, D. E., and Dervan P. B., Current Opinion in Structural Biology, 7:355-361 (1997); Walker, W. L., Kopka, J. L. and Goodsell, D. S., Biopolymers, 44:323-334 (1997); Zimmer, C. & Wahnert, U. Prog. Biophys. Molec. Bio. 47:31-112 (1986) and Reddy, B. S. P., Dondhi, S. M., and Lown, J. W., Pharmacol. Therap., 84:1-111 (1999) (the disclosures of which are herein incorporated by reference in their entireties). A preferred MGB in accordance with the present disclosure is $DPI_3$. Synthesis methods and/or sources for such MGBs are also well known in the art. (See, e.g., U.S. Pat. Nos. 5,801,155; 6,492,346; 6,084,102; and 6,727,356, the disclosures of which are incorporated herein by reference in their entireties.)

As used herein, the term "MGB blocker probe," "MBG blocker," or "MGB probe" is an oligonucleotide sequence and/or probe further attached to a minor groove binder moiety at its 3' and/or 5' end. Oligonucleotides conjugated to MGB moieties form extremely stable duplexes with single-stranded and double-stranded DNA targets, thus allowing shorter probes to be used for hybridization based assays. In comparison to unmodified DNA, MGB probes have higher melting temperatures (Tm) and increased specificity, especially when a mismatch is near the MGB region of the hybridized duplex. (See, e.g., Kutyavin, I. V., et al., Nucleic Acids Research, 2000, Vol. 28, No. 2: 655-661).

As used herein, the term "modified base" refers generally to any modification of a base or the chemical linkage of a base in a nucleic acid that differs in structure from that found in a naturally occurring nucleic acid. Such modifications can include changes in the chemical structures of bases or in the chemical linkage of a base in a nucleic acid, or in the backbone structure of the nucleic acid. (See, e.g., Latorra, D. et al., *Hum Mut* 2003, 2:79-85. Nakiandwe, J. et al., *plant Method* 2007, 3:2.)

As used herein, the term "detector probe" refers to any of a variety of signaling molecules indicative of amplification. For example, SYBR® Green and other DNA-binding dyes are detector probes. Some detector probes can be sequence-based (also referred to herein as "locus-specific detector probe"), for example 5' nuclease probes. Various detector probes are known in the art, for example (TaqMan® probes described herein (See also U.S. Pat. No. 5,538,848) various stem-loop molecular beacons (See, e.g., U.S. Pat. Nos. 6,103,476 and 5,925,517 and Tyagi and Kramer, 1996, Nature Biotechnology 14:303-308), stemless or linear beacons (See, e.g., WO 99/21881), PNA Molecular Beacons™ (See, e.g., U.S. Pat. Nos. 6,355,421 and 6,593,091), linear PNA beacons (See, e.g., Kubista et al., 2001, SPIE 4264: 53-58), non-FRET probes (See, e.g., U.S. Pat. No. 6,150, 097), Sunrise®/Amplifluor® probes (U.S. Pat. No. 6,548, 250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Detector probes can comprise reporter dyes such as, for example, 6-carboxyfluorescein (6-FAM) or tetrachlorofluorescin (TET). Detector probes can also comprise quencher moieties such as tetramethylrhodamine (TAMRA), Black Hole Quenchers (Biosearch), Iowa Black (IDT), QSY quencher (Molecular Probes), and Dabsyl and Dabcel sulfonate/carboxylate Quenchers (Epoch). Detector probes can also comprise two probes, wherein for example a fluor is on one probe, and a quencher on the other, wherein hybridization of the two probes together on a target quenches the signal, or wherein hybridization on a target alters the signal signature via a change in fluorescence. Detector probes can also comprise sulfonate derivatives of fluorescein dyes with $SO_3$ instead of the carboxylate group, phosphoramidite forms of fluorescein, phosphoramidite forms of CY5 (available, for example, from Amersham Biosciences-GE Healthcare).

As used herein, the term "locus-specific primer" refers to an oligonucleotide sequence that hybridizes to products derived from the extension of a first primer (such as an allele-specific primer) in a PCR reaction, and which can effectuate second strand cDNA synthesis of said product. Accordingly, in some embodiments, the allele-specific primer serves as a forward PCR primer and the locus-specific primer serves as a reverse PCR primer, or vice versa. In some preferred embodiments, locus-specific primers are present at a higher concentration as compared to the allele-specific primers.

As used herein, the term "rare allelic variant" refers to a target polynucleotide present at a lower level in a sample as compared to an alternative allelic variant. The rare allelic variant may also be referred to as a "minor allelic variant" and/or a "mutant allelic variant." For instance, the rare allelic variant may be found at a frequency less than 1/10, 1/100, 1/1,000, 1/10,000, 1/100,000, 1/1,000,000, 1/10,000, 000, 1/100,000,000 or 1/1,000,000,000 compared to another allelic variant for a given SNP or gene. Alternatively, the rare allelic variant can be, for example, less than 2, 3, 4, 5, 6, 7, 8, 9, 10, 15, 20, 25, 50, 75, 100, 250, 500, 750, 1,000, 2,500, 5,000, 7,500, 10,000, 25,000, 50,000, 75,000, 100,000, 250,000, 500,000, 750,000, or 1,000,000 copies per 1, 10, 100, 1,000 micro liters of a sample or a reaction volume.

As used herein, the terms "abundant allelic variant" may refer to a target polynucleotide present at a higher level in a sample as compared to an alternative allelic variant. The abundant allelic variant may also be referred to as a "major allelic variant" and/or a "wild type allelic variant." For instance, the abundant allelic variant may be found at a frequency greater than 10×, 100×, 1,000×, 10,000×, 100, 000×, 1,000,000×, 10,000,000×, 100,000,000× or 1,000, 000,000× compared to another allelic variant for a given SNP or gene. Alternatively, the abundant allelic variant can be, for example, greater than 2, 3, 4, 5, 6, 7, 8, 9, 10, 15, 20, 25, 50, 75, 100, 250, 500, 750, 1,000, 2,500, 5,000, 7,500, 10,000, 25,000, 50,000, 75,000, 100,000, 250,000, 500,000, 750,000, 1,000,000 copies per 1, 10, 100, 1,000 micro liters of a sample or a reaction volume.

As used herein, the terms "first" and "second" are used to distinguish the components of a first reaction (e.g., a "first" reaction; a "first" allele-specific primer) and a second reaction (e.g., a "second" reaction; a "second" allele-specific primer). By convention, as used herein the first reaction amplifies a first (for example, a rare) allelic variant and the second reaction amplifies a second (for example, an abundant) allelic variant or vice versa.

As used herein, both "first allelic variant" and "second allelic variant" can pertain to alleles of a given locus from the same organism. For example, as might be the case in human samples (e.g., cells) comprising wild type alleles, some of which have been mutated to form a minor or rare allele. The first and second allelic variants of the present teachings can also refer to alleles from different organisms. For example, the first allele can be an allele of a genetically modified organism, and the second allele can be the corresponding allele of a wild type organism. The first allelic variants and second allelic variants of the present teachings can be contained on gDNA, as well as mRNA and cDNA, and generally any target nucleic acids that exhibit sequence variability due to, for example, SNP or nucleotide(s) insertion and/or deletion mutations.

As used herein, the term "thermostable" or "thermostable polymerase" refers to an enzyme that is heat stable or heat resistant and catalyzes polymerization of deoxyribonucleotides to form primer extension products that are complementary to a nucleic acid strand. Thermostable DNA polymerases useful herein are not irreversibly inactivated when subjected to elevated temperatures for the time necessary to effect destabilization of single-stranded nucleic acids or denaturation of double-stranded nucleic acids during PCR amplification. Irreversible denaturation of the enzyme refers to substantial loss of enzyme activity. Preferably a thermostable DNA polymerase will not irreversibly denature at about 90°-100° C. under conditions such as is typically required for PCR amplification.

As used herein, the term "PCR amplifying" or "PCR amplification" refers generally to cycling polymerase-mediated exponential amplification of nucleic acids employing primers that hybridize to complementary strands, as described for example in Innis et al., PCR Protocols: A Guide to Methods and Applications, Academic Press (1990). Devices have been developed that can perform thermal cycling reactions with compositions containing fluorescent indicators which are able to emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; 6,174,670; and 6,814,934 and include, but are not limited to, the ABI Prism® 7700 Sequence Detection System (Applied Biosystems, Foster City, Calif.), the ABI GeneAmp® 5700 Sequence Detection System (Applied Biosystems, Foster City, Calif.), the ABI GeneAmp® 7300 Sequence Detection System (Applied Biosystems, Foster City, Calif.), the ABI GeneAmp® 7500 Sequence Detection System (Applied Biosystems, Foster City, Calif.), the StepOne™ Real-Time PCR System (Applied Biosystems, Foster City, Calif.) and the ABI GeneAmp® 7900 Sequence Detection System (Applied Biosystems, Foster City, Calif.).

As used herein, the term "Tm" or "melting temperature" of an oligonucleotide refers to the temperature (in degrees Celsius) at which 50% of the molecules in a population of a single-stranded oligonucleotide are hybridized to their complementary sequence and 50% of the molecules in the population are not-hybridized to said complementary sequence. The Tm of a primer or probe can be determined empirically by means of a melting curve. In some cases it can also be calculated using formulas well know in the art (See, e.g., Maniatis, T., et al., Molecular cloning: a laboratory manual/Cold Spring Harbor Laboratory, Cold Spring Harbor, N.Y.: 1982).

As used herein, the term "sensitivity" refers to the minimum amount (number of copies or mass) of a template that can be detected by a given assay. As used herein, the term "specificity" refers to the ability of an assay to distinguish between amplification from a matched template versus a mismatched template. Frequently, specificity is expressed as $\Delta C_t = Ct_{mismatch} - Ct_{match}$. An improvement in specificity or "specificity improvement" or "fold difference" is expressed herein as $2^{(Ct\_condition1 - Ct\_condition2)}$. The term "selectivity" refers to the extent to which an AS-PCR assay can be used to determine minor (often mutant) alleles in mixtures without interferences from major (often wild type) alleles. Selectivity is often expressed as a ratio or percentage. For example, an assay that can detect 1 mutant template in the presence of 100 wild type templates is said to have a selectivity of 1:100 or 1%. As used herein, assay selectivity can also be calculated as $\frac{1}{2}^{Ct}$ or as a percentage using ($\frac{1}{2}^{Ct}$ ⊐ 100).

As used herein, the term "Ct" or "Ct value" refers to threshold cycle and signifies the cycle of a PCR amplification assay in which signal from a reporter that is indicative of amplicon generation (e.g., fluorescence) first becomes detectable above a background level. In some embodiments, the threshold cycle or "Ct" is the cycle number at which PCR amplification becomes exponential.

As used herein, the term "delta Ct" or "ΔCt" refers to the difference in the numerical cycle number at which the signal passes the fixed threshold between two different samples or reactions. In some embodiments delta Ct is the difference in numerical cycle number at which exponential amplification is reached between two different samples or reactions. The delta Ct can be used to identify the specificity between a matched primer to the corresponding target nucleic acid sequence and a mismatched primer to the same corresponding target nucleic acid sequence.

In some embodiments, the calculation of the delta Ct value between a mismatched primer and a matched primer is used as one measure of the discriminating power of allele-specific PCR. In general, any factor which increases the difference between the Ct value for an amplification reaction using a primer that is matched to a target sequence (e.g., a sequence comprising an allelic variant of interest) and that of a mismatched primer will result in greater allele discrimination power.

According to various embodiments, a Ct value may be determined using a derivative of a PCR curve. For example, a first, second, or nth order derivative method may be performed on a PCR curve in order to determine a Ct value. In various embodiments, a characteristic of a derivative may be used in the determination of a Ct value. Such characteristics may include, but are not limited by, a positive inflection of a second derivative, a negative inflection of a second derivative, a zero crossing of the second derivative, or a positive inflection of a first derivative. In various embodiments, a Ct value may be determined using a thresholding and baselining method. For example, an upper bound to an exponential phase of a PCR curve may be established using a derivative method, while a baseline for a PCR curve may be determined to establish a lower bound to an exponential phase of a PCR curve. From the upper and lower bound of a PCR curve, a threshold value may be established from which a Ct value is determined. Other methods for the determination of a Ct value known in the art, for example, but not limited by, various embodiments of a fit point method, and various embodiments of a sigmoidal method (See, e.g., U.S. Pat. Nos. 6,303,305; 6,503,720; 6,783,934, 7,228,237 and U.S. Application No. 2004/0096819; the disclosures of which are herein incorporated by reference in their entireties).

III. Compositions, Methods and Kits

In one aspect, the present invention provides compositions for use in identifying and/or quantitating an allelic variant in a nucleic acid sample. Some of these compositions can comprise: (a) an allele-specific primer; (b) an allele-specific blocker probe; (c) a detector probe; and/or (d) a locus-specific primer. In some embodiments of the compositions, the compositions may further comprise a polymerase, dNTPs, reagents and/or buffers suitable for PCR amplification, and/or a template sequence or nucleic acid sample. In some embodiments, the polymerase can be thermostable.

In another aspect, the invention provides compositions comprising: (i) a first allele-specific primer, wherein an allele-specific nucleotide portion of the first allele-specific primer is complementary to the first allelic variant of a target sequence; and (ii) a first allele-specific blocker probe that is complementary to a region of the target sequence comprising the second allelic variant, wherein said region encompasses a position corresponding to the binding position of the allele-specific nucleotide portion of the first allele-specific primer, and wherein the first allele-specific blocker probe comprises a minor groove binder.

In some illustrative embodiments, the compositions can further include a locus-specific primer that is complementary to a region of the target sequence that is 3' from the first allelic variant and on the opposite strand.

In further embodiments, the compositions can further include a detector probe.

In another aspect, the present invention provides methods for amplifying an allele-specific sequence. Some of these methods can include: (a) hybridizing an allele-specific primer to a first nucleic acid molecule comprising a target allele; (b) hybridizing an allele-specific blocker probe to a second nucleic acid molecule comprising an alternative allele wherein the alternative allele corresponds to the same loci as the target allele; (c) hybridizing a locus-specific detector probe to the first nucleic acid molecule; (d) hybridizing a locus-specific primer to the extension product of the allele-specific primer and (e) PCR amplifying the target allele.

In another aspect, the present invention provides methods for detecting and/or quantitating an allelic variant in a mixed sample. Some of these methods can involve: (a) in a first reaction mixture hybridizing a first allele-specific primer to a first nucleic acid molecule comprising a first allele (allele-1) and in a second reaction mixture hybridizing a second allele-specific primer to a first nucleic acid molecule comprising a second allele (allele-2), wherein the allele-2 corresponds to the same loci as allele-1; (b) in the first reaction mixture hybridizing a first allele-specific blocker probe to a second nucleic acid molecule comprising allele-2 and in the second reaction mixture hybridizing a second allele-specific blocker probe to a second nucleic acid molecule comprising allele-1; (c) in the first reaction mixture, hybridizing a first detector probe to the first nucleic acid molecule and in the second reaction mixture, hybridizing a second detector probe to the first nucleic acid molecule; (d) in the first reaction mixture hybridizing a first locus-specific primer to the extension product of the first allele-specific primer and in the second reaction mixture hybridizing a second locus-specific primer to the extension product of the second allele-specific primer; and (e) PCR amplifying the first nucleic acid molecule to form a first set or sample of amplicons and PCR amplifying the second nucleic acid molecule to form a second set or sample of amplicons; and (f) comparing the first set of amplicons to the second set of amplicons to quantitate allele-1 in the sample comprising allele-2 and/or allele-2 in the sample comprising allele-1.

In yet another aspect, the present invention provides methods for detecting and/or quantitating allelic variants. Some of these methods can comprise: (a) PCR amplifying a first allelic variant in a first reaction comprising (i) a low-concentration first allele-specific primer, (ii) a first locus-specific primer, and (iii) a first blocker probe to form first amplicons; (b) PCR amplifying a second allelic variant in a second reaction comprising (i) a low-concentration second allele-specific primer, (ii) a second locus-specific primer, and (iii) a second blocker probe to form second amplicons; and (d) comparing the first amplicons to the second amplicons to quantitate the first allelic variant in the sample comprising second allelic variants.

In yet another aspect, the present invention provides methods for detecting a first allelic variant of a target sequence in a nucleic acid sample suspected of comprising at least a second allelic variant of the target sequence. Methods of this aspect include forming a first reaction mixture by combining the following: (i) a nucleic acid sample; (ii) a first allele-specific primer, wherein an allele-specific nucleotide portion of the first allele-specific primer is complementary to the first allelic variant of the target sequence; (iii) a first allele-specific blocker probe that is complementary to a region of the target sequence comprising the second allelic variant, wherein said region encompasses a position corresponding to the binding position of the allele-specific nucleotide portion of the first allele-specific primer, and wherein the first allele-specific blocker probe comprises a minor groove binder; (iv) a first locus-specific primer that is complementary to a region of the target sequence that is 3' from the first allelic variant and on the opposite strand; and (v) a first detector probe.

Next an amplification reaction, typically a PCR amplification reaction, is carried out on the first reaction mixture using the first locus-specific primer and the first allele-specific primer to form a first amplicon. Then, the first amplicon is detected by a change in a detectable property of the first detector probe upon binding to the amplicon, thereby detecting the first allelic variant of the target gene in the nucleic acid sample. The detector probe in some illustrative embodiments is a 5' nuclease probe. The detectable property in certain illustrative embodiments is fluorescence.

In some embodiments, the 3' nucleotide position of the 5' target region of the first allele-specific primer is an allele-specific nucleotide position. In certain other illustrative embodiments, including those embodiments where the 3' nucleotide position of the 5' target region of the first allele-specific primer is an allele-specific nucleotide position, the blocking region of the allele-specific primer encompasses the allele-specific nucleotide position. Furthermore, in illustrative embodiments, the first allele-specific blocker probe includes a minor groove binder. Furthermore, the allele-specific blocker probe in certain illustrative embodiments does not have a label, for example a fluorescent label, or a quencher.

In certain illustrative embodiments, the quantity of the first allelic variant is determined by evaluating the change in a detectable property of the first detector probe.

In certain illustrative embodiments, the method further includes forming a second reaction mixture by combining (i) the nucleic acid sample; (ii) a second allele-specific primer, wherein an allele-specific nucleotide portion of the second allele-specific primer is complementary to the second allelic variant of the target sequence; (iii) a second allele-specific blocker probe that is complementary to a region of the target sequence comprising the first allelic variant, wherein said region encompasses a position corresponding to the binding position of the allele-specific nucleotide portion of the second allele-specific primer, and wherein the second allele-specific blocker probe comprises a minor groove binder; (iv) a second locus-specific primer that is complementary to a region of the target sequence that is 3' from the second allelic variant and on the opposite strand; and (v) a second detector probe. Next, an amplification reaction is carried out on the second reaction mixture using the second allele-specific primer and the locus-specific primer, to form a second amplicon. Then the second amplicon is detected by a change in a detectable property of the detector probe.

In certain embodiments, the method further includes comparing the change in a detectable property of the first detector probe in the first reaction mixture to the change in a detectable property of the second detector probe in the second reaction mixture.

In yet another aspect, the present invention provides a reaction mixture that includes the following (i) nucleic acid molecule; (ii) an allele-specific primer, wherein an allele-specific nucleotide portion of the allele-specific primer is complementary to a first allelic variant of a target sequence; (iii) an allele-specific blocker probe that is complementary to a region of the target sequence comprising a second allelic variant, wherein said region encompasses a position corresponding to the binding position of the allele-specific nucleotide portion of the allele-specific primer, and wherein the allele-specific blocker probe comprises a minor groove binder; (iv) a locus-specific primer that is complementary to a region of the target sequence that is 3' from the first allelic variant and on the opposite strand; and (v) a detector probe.

In certain embodiments, the methods of the invention are used to detect a first allelic variant that is present at a frequency less than $1/10$, $1/100$, $1/1,000$, $1/10,000$, $1/100,000$, $1/1,000,000$, $1/10,000,000$, $1/100,000,000$ or $1/1,000,000,000$, and any fractional ranges in between, of a second allelic variant for a given SNP or gene. In other embodiments, the methods are used to detect a first allelic variant that is present in less than 2, 3, 4, 5, 6, 7, 8, 9, 10, 15, 20, 25, 50, 75, 100, 250, 500, 750, 1,000, 2,500, 5,000, 7,500, 10,000, 25,000, 50,000, 75,000, 100,000, 250,000, 500,000, 750,000, 1,000,000 copies per 1, 10, 100, 1,000 micro liters, and any fractional ranges in between, of a sample or a reaction volume.

In some embodiments the first allelic variant is a mutant. In some embodiments the second allelic variant is wild type. In some embodiments, the present methods can involve detecting one mutant molecule in a background of at least 1,000 to 1,000,000, such as about 1000 to 10,000, about 10,000 to 100,000, or about 100,000 to 1,000,000 wild type molecules, or any fractional ranges in between. In some embodiments, the methods can provide high sensitivity and the efficiency at least comparable to that of TaqMan®-based assays.

In some embodiments, the comparison of the first amplicons and the second amplicons involving the disclosed methods provides improvements in specificity from 1,000× to 1,000,000× fold difference, such as about 1000 to 10,000×, about 10,000 to 100,000×, or about 100,000 to 1,000,000× fold difference, or any fractional ranges in between. In some embodiments, the size of the amplicons range from about 60-120 nucleotides long.

In another aspect, the present invention provides kits for quantitating a first allelic variant in a sample comprising an alternative second allelic variants that include: (a) a first allele-specific primer; (b) a second allele-specific primer; (c), a first locus-specific primer; (d) a second locus-specific primer; (e) a first allele-specific blocker probe; (f) a second allele-specific blocker probe; and (g) a polymerase. In some embodiments of the disclosed kits, the kit further comprises a first locus-specific detector probe and a second locus-specific detector probe.

In another aspect, the present invention provides kits that include two or more containers comprising the following components independently distributed in one of the two or more containers: (i) a first allele-specific primer, wherein an allele-specific nucleotide portion of the first allele-specific primer is complementary to the first allelic variant of a target sequence; and (ii) a first allele-specific blocker probe that is complementary to a region of the target sequence comprising the second allelic variant, wherein said region encompasses a position corresponding to the binding position of the allele-specific nucleotide portion of the first allele-specific primer, and wherein the first allele-specific blocker probe comprises a minor groove binder.

In some illustrative embodiments, the kits can further include a locus-specific primer that is complementary to a region of the target sequence that is 3' from the first allelic variant and on the opposite strand.

In other embodiments, the kits can further include a detector probe.

In some embodiments, the compositions, methods, and/or kits can be used in detecting circulating cells in diagnosis. In one embodiment, the compositions, methods, and/or kits can be used to detect tumor cells in blood for early cancer diagnosis. In some embodiments, the compositions, methods, and/or kits can be used for cancer or disease-associated genetic variation or somatic mutation detection and validation. In some embodiments, the compositions, methods, and/or kits can be used for genotyping tera-, tri- and di-allelic SNPs. In some embodiments, the compositions, methods, and/or kits can be used for DNA typing from mixed DNA samples for QC and human identification assays, cell line QC for cell contaminations, allelic gene expression analysis, virus typing/rare pathogen detection, mutation detection from pooled samples, detection of circulating tumor cells in blood, and/or prenatal diagnostics.

In some embodiments, the compositions, methods, and/or kits are compatible with various instruments such as, for example, SDS instruments from Applied Biosystems (Foster City, Calif.).

Allele-Specific Primers

Allele-specific primers (ASPs) designed with low Tms exhibit increased discrimination of allelic variants. In some embodiments, the allele-specific primers are short oligomers ranging from about 15-30, such as about 16-28, about 17-26, about 18-24, or about 20-22, or any range in between, nucleotides in length. In some embodiments, the Tm of the allele-specific primers range from about 50° C. to 70° C., such as about 52° C. to 68° C. (e.g., 53° C.), about 54° C. to 66° C., about 56° C. to 64° C., about 58° C. to 62° C., or any range in between. In other embodiments, the Tm of the allele-specific primers is about 3° C. to 6° C. higher than the anneal/extend temperature of the PCR cycling conditions employed during amplification.

Low allele-specific primer concentration can also improve selectivity. Reduction in concentration of allele-specific primers below 900 nM can increase the delta Ct between matched and mismatched sequences. In some embodiments of the disclosed compositions, the concentration of allele-specific primers ranges from about 20 nM to 900 nM, such as about 50 nM to 700 nM, about 100 nM to 500 nM, about 200 nM to 300 nM, about 400 nM to 500 nM, or any range in between. In some exemplary embodiments, the concentration of the allele-specific primers is between about 200 nM to 400 nM.

In some embodiments, allele-specific primers can comprise an allele-specific nucleotide portion that is specific to the target allele of interest. The allele-specific nucleotide portion of an allele-specific primer is complementary to one allele of a gene, but not another allele of the gene. In other words, the allele-specific nucleotide portion binds to one or more variable nucleotide positions of a gene that is nucleotide positions that are known to include different nucleotides for different allelic variants of a gene. The allele-specific nucleotide portion is at least one nucleotide in length. In exemplary embodiments, the allele-specific nucleotide portion is one nucleotide in length. In some embodiments, the allele-specific nucleotide portion of an allele-specific primer is located at the 3' terminus of the allele-specific primer. In other embodiments, the allele-specific nucleotide portion is located about 1-2, 3-4, 5-6, 7-8, 9-11, 12-15, or 16-20 nucleotides in from the 3'most-end of the allele-specific primer.

Allele-specific primers designed to target discriminating bases can also improve discrimination of allelic variants. In some embodiments, the nucleotide of the allele-specific nucleotide portion targets a highly discriminating base (e.g., for detection of A/A, A/G, G/A, G/G, A/C, or C/A alleles). Less discriminating bases, for example, may involve detection of C/C, T/C, G/T, T/G, C/T alleles. In some embodiments, for example when the allele to be detected involves A/G or C/T SNPs, A or G may be used as the 3' allele-specific nucleotide portion of the allele-specific primer (e.g., if A/T is the target allele), or C or T may be used as the 3' allele-specific nucleotide portion of the allele-specific primer (e.g., if C/G is the target allele). In other embodiments, A may be used as the nucleotide-specific portion at the 3' end of the allele specific primer (e.g., the allele-specific nucleotide portion) when detecting and/or quantifying A/T SNPs. In other embodiments, G may be used as the nucleotide-specific portion at the 3' end of the allele specific primer when detecting and/or quantifying C/G SNPs.

In some embodiments, the allele-specific primer can comprise a target-specific portion that is specific to the polynucleotide sequence (or locus) of interest. In some embodiments the target-specific portion is about 75-85%, 85-95%, 95-99% or 100% complementary to the target polynucleotide sequence of interest. In some embodiments, the target-specific portion of the allele-specific primer can comprise the allele-specific nucleotide portion. In other embodiments, the target-specific portion is located 5' to the allele-specific nucleotide portion. The target-specific portion can be about 4-30, about 5-25, about 6-20, about 7-15, or about 8-10 nucleotides in length. In some embodiments, the Tm of the target specific portion is about 5° C. below the anneal/extend temperature used for PCR cycling. In some embodiments, the Tm of the target specific portion of the allele-specific primer ranges from about 51° C. to 60° C., about 52° C. to 59° C., about 53° C. to 58° C., about 54° C. to 57° C., about 55° C. to 56° C., or about 50° C. to about 60° C.

In some embodiments of the disclosed methods and kits, the target-specific portion of the first allele-specific primer and the target-specific portion of the second allele-specific primer comprise the same sequence. In other embodiments, the target-specific portion of the first allele-specific primer and the target-specific portion of the second allele-specific primer are the same sequence.

In some embodiments, the allele-specific primer comprises a tail. Allele-specific primers comprising tails, enable the overall length of the primer to be reduced, thereby lowering the Tm without significant impact on assay sensitivity.

In some exemplary embodiments, the tail is on the 5' terminus of the allele-specific primer. In some embodiments, the tail is located 5' of the target-specific portion and/or allele-specific nucleotide portion of the allele-specific primer. In some embodiments, the tail is about 65-75%, about 75-85%, about 85-95%, about 95-99% or about 100% non-complementary to the target polynucleotide sequence of interest. In some embodiments the tail can be about 2-40, such as about 4-30, about 5-25, about 6-20, about 7-15, or about 8-10 nucleotides in length. In some embodiments the tail is GC-rich. For example, in some embodiments the tail sequence is comprised of about 50-100%, about 60-100%, about 70-100%, about 80-100%, about 90-100% or about 95-100% G and/or C nucleotides.

The tail of the allele-specific primer may be configured in a number of different ways, including, but not limited to a configuration whereby the tail region is available after primer extension to hybridize to a complementary sequence (if present) in a primer extension product. Thus, for example, the tail of the allele-specific primer can hybridize to the complementary sequence in an extension product resulting from extension of a locus-specific primer.

In some embodiments of the disclosed methods and kits, the tail of the first allele-specific primer and the tail of the second allele-specific primer comprise the same sequence. In other embodiments, the 5' tail of the first allele-specific primer and the 5' tail of the second allele-specific primer are the same sequence.

Allele-Specific Blocker Probes

Allele-specific blocker probes (or ASBs) (herein sometimes referred to as "blocker probes") may be designed as short oligomers that are single-stranded and have a length of 100 nucleotides or less, more preferably 50 nucleotides or less, still more preferably 30 nucleotides or less and most preferably 20 nucleotides or less with a lower limit being approximately 5 nucleotides.

In some embodiments, the Tm of the blocker probes range from 60° C. to 70° C., 61° C. to 69° C., 62° C. to 68° C., 63° C. to 67° C., 64° C. to 66° C., or about 60° C. to about 63° C., or any range in between. In yet other embodiments, the Tm of the allele-specific blocker probes is about 3° C. to 6° C. higher than the anneal/extend temperature in the PCR cycling conditions employed during amplification.

In some embodiments, the blocker probes are not cleaved during PCR amplification. In some embodiments, the blocker probes comprise a non-extendable blocker moiety at their 3'-ends. In some embodiments, the blocker probes can further comprise other moieties (including, but not limited to additional non-extendable blocker moieties, quencher moieties, fluorescent moieties, etc) at their 3'-end, 5'-end, and/or any internal position in between. In some embodiments, the allele position is located about 5-15, such as about 5-11, about 6-10, about 7-9, about 7-12, or about 9-11, such as about 6, about 7, about 8, about 9, about 10, or about 11 nucleotides away from the non-extendable blocker moiety of the allele-specific blocker probes when hybridized to their target sequences. In some embodiments, the non-extendable blocker moiety can be, but is not limited to, an amine ($NH_2$), biotin, PEG, $DPI_3$, or $PO_4$. In some preferred embodiments, the blocker moiety is a minor groove binder (MGB) moiety. (The oligonucleotide-MGB conjugates of the present invention are hereinafter sometimes referred to as "MGB blocker probes" or "MGB blockers.")

As disclosed herein, the use of MGB moieties in allele-specific blocker probes can increase the specificity of allele-specific PCR. One possibility for this effect is that, due to their strong affinity to hybridize and strongly bind to complementary sequences of single or double stranded nucleic acids, MGBs can lower the Tm of linked oligonucleotides (See, for example, Kutyavin, I., et al., Nucleic Acids Res., 2000, Vol. 28, No. 2: 655-661). Oligonucleotides comprising MGB moieties have strict geometric requirements since the linker between the oligonucleotide and the MGB moiety must be flexible enough to allow positioning of the MGB in the minor groove after DNA duplex formation. Thus, MGB blocker probes can provide larger Tm differences between matched versus mismatched alleles as compared to conventional DNA blocker probes.

In general, MGB moieties are molecules that binds within the minor groove of double stranded DNA. Although a generic chemical formula for all known MGB compounds cannot be provided because such compounds have widely varying chemical structures, compounds which are capable of binding in the minor groove of DNA, generally speaking, have a crescent shape three dimensional structure. Most MGB moieties have a strong preference for A-T (adenine and thymine) rich regions of the B form of double stranded DNA. Nevertheless, MGB compounds which would show preference to C-G (cytosine and guanine) rich regions are also theoretically possible. Therefore, oligonucleotides comprising a radical or moiety derived from minor groove binder molecules having preference for C-G regions are also within the scope of the present invention.

Some MGBs are capable of binding within the minor groove of double stranded DNA with an association constant of $10^3 M^{-1}$ or greater. This type of binding can be detected by well established spectrophotometric methods such as ultraviolet (UV) and nuclear magnetic resonance (NMR) spectroscopy and also by gel electrophoresis. Shifts in UV spectra upon binding of a minor groove binder molecule and NMR spectroscopy utilizing the "Nuclear Overhauser" (NOSEY) effect are particularly well known and useful techniques for this purpose. Gel electrophoresis detects binding of an MGB to double stranded DNA or fragment thereof, because upon such binding the mobility of the double stranded DNA changes.

A variety of suitable minor groove binders have been described in the literature. See, for example, Kutyavin, et al. U.S. Pat. No. 5,801,155; Wemmer, D. E., and Dervan P. B., Current Opinion in Structural Biology, 7:355-361 (1997); Walker, W. L., Kopka, J. L. and Goodsell, D. S., Biopolymers, 44:323-334 (1997); Zimmer, C. & Wahnert, U. Prog. Biophys. Molec. Bio. 47:31-112 (1986) and Reddy, B. S. P., Dondhi, S. M., and Lown, J. W., Pharmacol. Therap., 84:1-111 (1999). In one group of embodiments, the MGB is selected from the group consisting of CC1065 analogs, lexitropsins, distamycin, netropsin, berenil, duocarmycin, pentamidine, 4,6-diamino-2-phenylindole and pyrrolo[2,1-c][1,4]benzodiazepines. A preferred MGB in accordance with the present disclosure is DPI$_3$ (see U.S. Pat. No. 6,727,356, the disclosure of which is incorporated herein by reference in its entirety).

Suitable methods for attaching MGBs through linkers to oligonucleotides or probes and have been described in, for example, U.S. Pat. Nos. 5,512,677; 5,419,966; 5,696,251; 5,585,481; 5,942,610; 5,736,626; 5,801,155 and 6,727,356. (The disclosures of each of which are incorporated herein by reference in their entireties.) For example, MGB-oligonucleotide conjugates can be synthesized using automated oligonucleotide synthesis methods from solid supports having cleavable linkers. In other examples, MGB probes can be prepared from an MGB modified solid support substantially in accordance with the procedure of Lukhtanov et al. Bioconjugate Chem., 7: 564-567 (1996). (The disclosure of which is also incorporated herein by reference in its entirety.) According to these methods, one or more MGB moieties can be attached at the 5'-end, the 3'-end and/or at any internal portion of the oligonucleotide.

The location of an MGB moiety within an MGB-oligonucleotide conjugate can affect the discriminatory properties of such a conjugate. An unpaired region within a duplex will likely result in changes in the shape of the minor groove in the vicinity of the mismatched base(s). Since MGBs fit best within the minor groove of a perfectly-matched DNA duplex, mismatches resulting in shape changes in the minor groove would reduce binding strength of an MGB to a region containing a mismatch. Hence, the ability of an MGB to stabilize such a hybrid would be decreased, thereby increasing the ability of an MGB-oligonucleotide conjugate to discriminate a mismatch from a perfectly-matched duplex. On the other hand, if a mismatch lies outside of the region complementary to an MGB-oligonucleotide conjugate, discriminatory ability for unconjugated and MGB-conjugated oligonucleotides of equal length is expected to be approximately the same. Since the ability of an oligonucleotide probe to discriminate single base pair mismatches depends on its length, shorter oligonucleotides are more effective in discriminating mismatches. The first advantage of the use of MGB-oligonucleotides conjugates in this context lies in the fact that much shorter oligonucleotides compared to those used in the art (i.e., 20-mers or shorter), having greater discriminatory powers, can be used, due to the pronounced stabilizing effect of MGB conjugation. Consequently, larger delta Tms of allele-specific blocker probes can improve AS-PCR assay specificity and selectivity.

Figure 3:
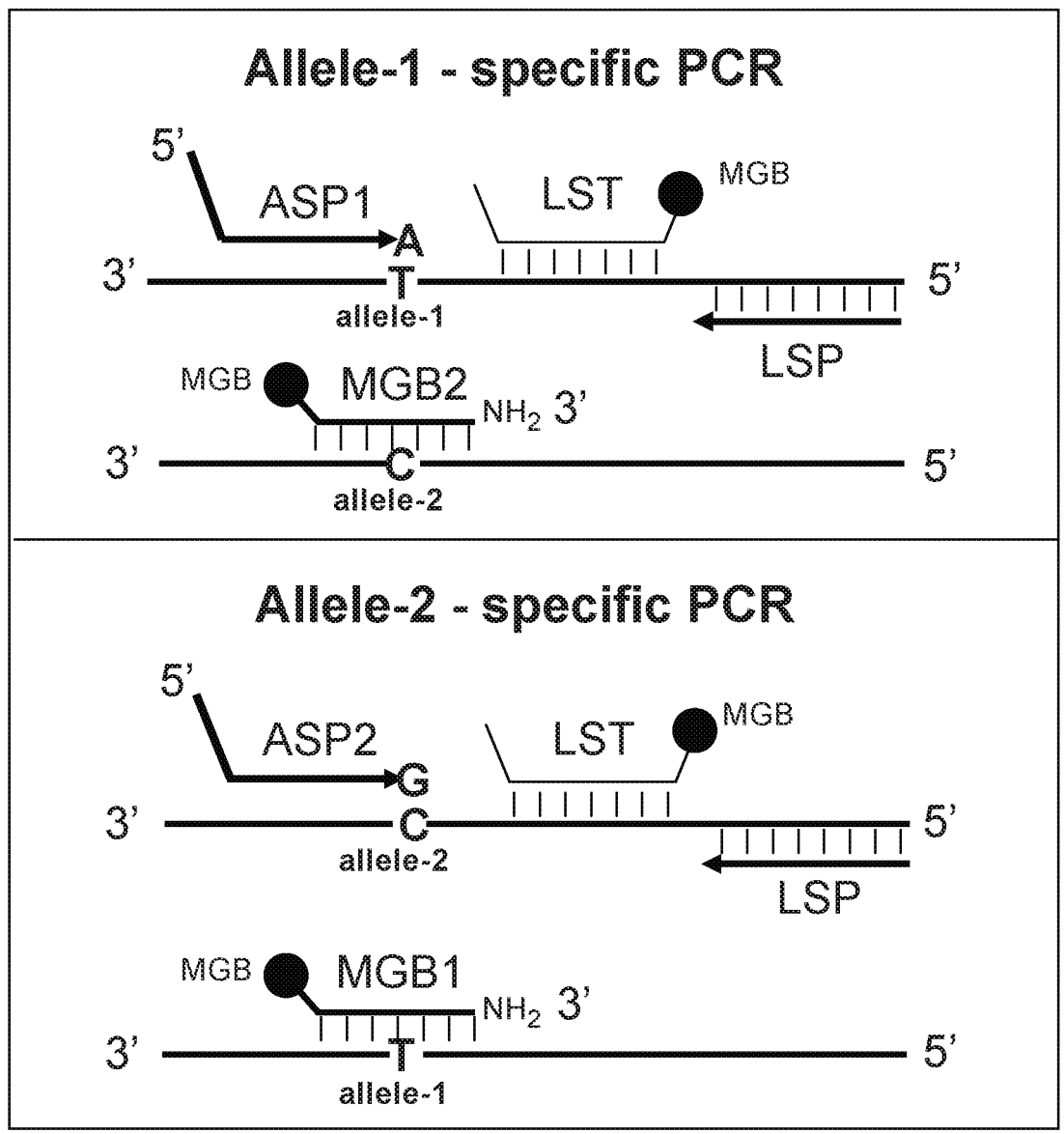
FIG. 3 depicts a schematic of an illustrative embodiment of cast-PCR using an allele-specific blocker probe with an MGB moiety at the 5' end. In some embodiments the blocker moiety at the 3'-end of the probe may include, for example, $NH_2$, biotin, MGB, $PO_4$, and PEG.

Blocker probes having MGB at the 5' termini may have additional advantages over other blocker probes having a blocker moiety (e.g., MGB, PO$_4$, NH$_2$, PEG, or biotin) only at the 3' terminus. This is at least because blocker probes having MGB at the 5' terminus (in addition to a blocking moiety at the 3'-end that prevents extension) will not be cleaved during PCR amplification. Thus, the probe concentration can be maintained at a constant level throughout PCR, which may help maintain the effectiveness of blocking non-specific priming, thereby increasing cast-PCR assay specificity and selectivity (FIG. 3).

Figure 4A:
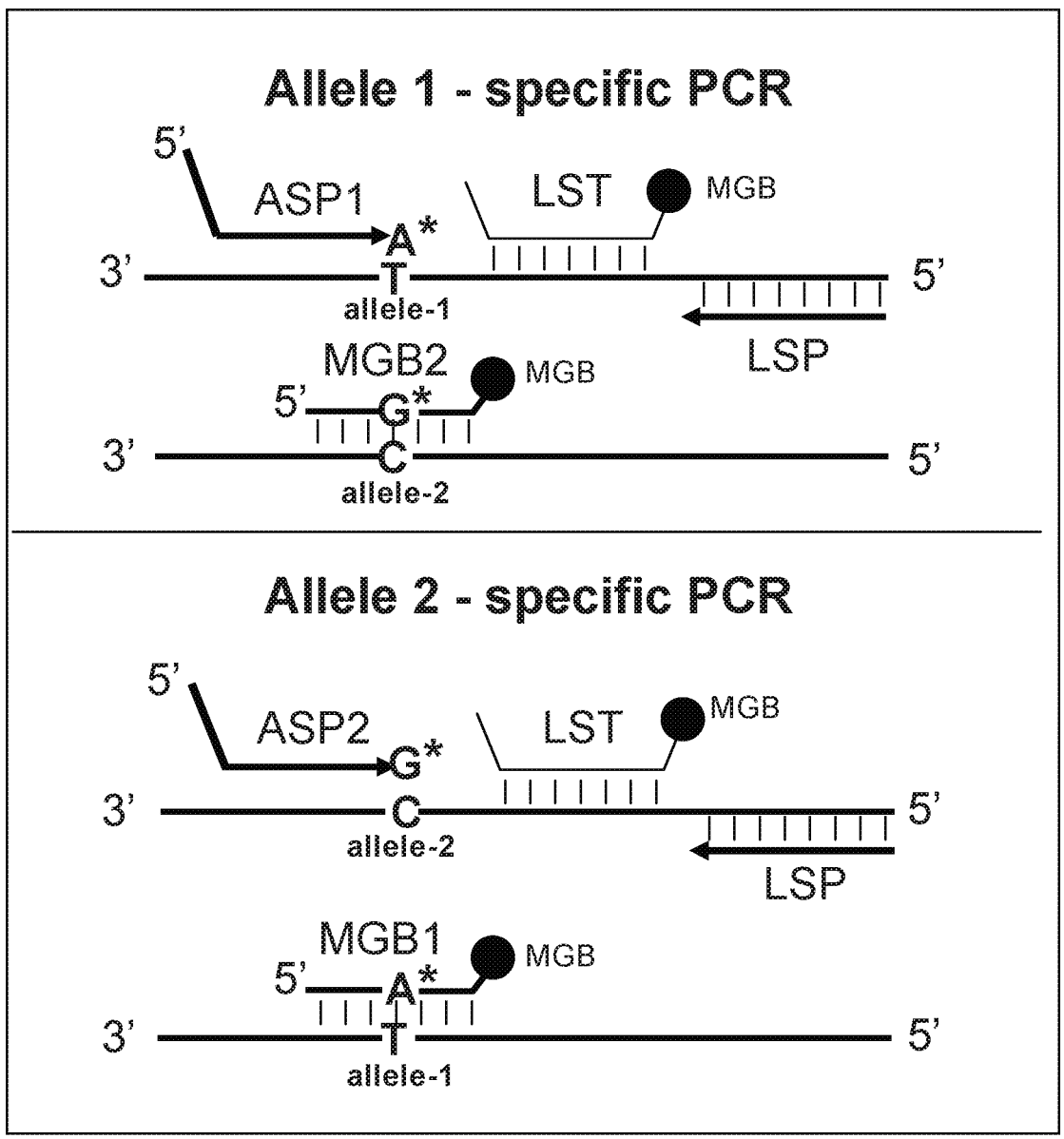
FIG. 4A depicts a schematic of an illustrative embodiment of cast-PCR using modified bases in an MGB blocker probe or allele-specific primer. (G* represents ppG.)

In some embodiments, the allele-specific blocker probe can comprise one or more modified bases in addition to the naturally occurring bases adenine, cytosine, guanine, thymine and uracil. In some embodiments, the modified base(s) may increase the difference in the Tm between matched and mismatched target sequences and/or decrease mismatch priming efficiency, thereby improving not only assay specificity, bust also selectivity (FIG. 4A).

Figure 4B:
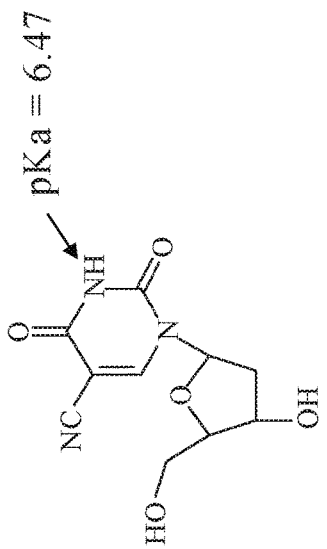
FIG. 4B depicts some examples of modified bases of an MGB blocker probe or allele-specific primer.

Modified bases are considered to be those that differ from the naturally-occurring bases by addition or deletion of one or more functional groups, differences in the heterocyclic ring structure (i.e., substitution of carbon for a heteroatom, or vice versa), and/or attachment of one or more linker arm structures to the base. Such modified base(s) may include, for example, 8-Aza-7-deaza-dA (ppA), 8-Aza-7-deaza-dG (ppG), locked nucleic acid (LNA) or 2'-O,4'-C-ethylene nucleic acid (ENA) bases (FIG. 4B). Other examples of modified bases include, but are not limited to, the general class of base analogues 7-deazapurines and their derivatives and pyrazolopyrimidines and their derivatives (described in PCT WO 90/14353; and U.S. application Ser. No. 09/054,630, the disclosures of each of which are incorporated herein by reference in their entireties). These base analogues, when present in an oligonucleotide, strengthen hybridization and improve mismatch discrimination. All tautomeric forms of naturally occurring bases, modified bases and base analogues may be included in the oligonucleotide primer and probes of the invention.

Similarly, modified sugars or sugar analogues can be present in one or more of the nucleotide subunits of an oligonucleotide conjugate in accordance with the invention. Sugar modifications include, but are not limited to, attachment of substituents to the 2', 3' and/or 4' carbon atom of the sugar, different epimeric forms of the sugar, differences in the α- or β-configuration of the glycosidic bond, and other anomeric changes. Sugar moieties include, but are not limited to, pentose, deoxypentose, hexose, deoxyhexose, ribose, deoxyribose, glucose, arabinose, pentofuranose, xylose, lyxose, and cyclopentyl.

Modified internucleotide linkages can also be present in oligonucleotide conjugates of the invention. Such modified linkages include, but are not limited to, peptide, phosphate, phosphodiester, phosphotriester, alkylphosphate, alkanephosphonate, thiophosphate, phosphorothioate, phosphorodithioate, methylphosphonate, phosphoramidate, substituted phosphoramidate and the like. Several further modifications of bases, sugars and/or internucleotide linkages, that are compatible with their use in oligonucleotides serving as probes and/or primers, will be apparent to those of skill in the art.

In addition, in some embodiments, the nucleotide units which are incorporated into the oligonucleotides of the MGB blocker probes of the present invention may have a cross-linking function (an alkylating agent) covalently bound to one or more of the bases, through a linking arm.

The "sugar" or glycoside portion of some embodiments of the MGB blocker probes of the present invention may comprise deoxyribose, ribose, 2-fiuororibose, 2-0 alkyl or alkenylribose where the alkyl group may have 1 to 6 carbons and the alkenyl group 2 to 6 carbons. In the naturally occurring nucleotides and in the herein described modifications and analogs the deoxyribose or ribose moiety forms a furanose ring. the glycosydic linkage is of the ~configuration and the purine bases are attached to the sugar moiety via the 9-position. the pyrimidines via the I-position and the pyrazolopyrimidines via the I-position. The nucleotide units of the oligonucleotide are interconnected by a "phosphate" backbone, as is well known in the art. The oligonucleotide of the oligonucleotide-MGB conjugates (MGB blocker probes) of the present invention may include, in addition to the "natural" phosphodiester linkages, phosphorothiotes and methylphosphonates.

In some embodiments of the methods and kits, the first allele-specific blocker probe binds to the same strand or sequence as the first allele-specific primer, while the second allele-specific blocker probe binds to the opposite strand and/or complementary sequence as the first allele-specific primer.

Detector Probes

In some embodiments, detector probe is designed as short oligomers ranging from about 15-30 nucleotides, such as about 16, about 18, about 22, about 24, about 30, or any number in between. In some embodiments, the Tm of the detector probe ranges from about 60° C. to 70° C., about 61° C. to 69° C., about 62° C. to 68° C., about 63° C. to 67° C., or about 64° C. to 66° C., or any range in between.

In some embodiments, the detector probe is a locus-specific detector probes (LST). In other embodiments the detector probe is a 5' nuclease probe. In some exemplary embodiments, the detector probe can comprises an MGB moiety, a reporter moiety (e.g., FAM™, TET™, JOE™, VIC™, or SYBR® Green), a quencher moiety (e.g., Black Hole Quencher™ or TAMRA™;), and/or a passive reference (e.g., ROX™). In some exemplary embodiments, the detector probe is designed according to the methods and principles described in U.S. Pat. No. 6,727,356 (the disclosure of which is incorporated herein by reference in its entirety). In some exemplary embodiments, the detector probe is a TaqMan® probe (Applied Biosystems, Foster City). In exemplary embodiments, the locus-specific detector probe can be designed according to the principles and methods described in U.S. Pat. No. 6,727,356 (the disclosure of which is incorporated herein by reference in its entirety). For example, fluorogenic probes can be prepared with a quencher at the 3' terminus of a single DNA strand and a fluorophore at the 5' terminus. In such an example, the 5'-nuclease activity of a Taq DNA polymerase can cleave the DNA strand, thereby separating the fluorophore from the quencher and releasing the fluorescent signal. In some embodiments, the detector probes are hybridized to the template strands during primer extension step of PCR amplification (e.g., at 60-65° C.). In yet other embodiments, an MGB is covalently attached to the quencher moiety of the locus-specific detector probes (e.g., through a linker).

In some embodiments of the disclosed methods and kits, the first and second detector probes are the same and/or comprise the same sequence or are the same sequence.

Locus-Specific Primers

In some embodiments, locus-specific primer (LSP) is designed as a short oligomer ranging from about 15-30 nucleotides, such as about 16, about 18, about 22, about 24, about 30, or any number in between. In some embodiments, the Tm of the locus-specific primer ranges from about 60° C. to 70° C., about 61° C. to 69° C., about 62° C. to 68° C., about 63° C. to 67° C., or about 64° C. to 66° C., or any range in between.

In some other embodiments of the disclosed methods and kits, the first locus-specific detector probe and/or second locus-specific detector probes comprise the same sequence or are the same sequence.

Additional Components

Polymerase enzymes suitable for the practice of the present invention are well known in the art and can be derived from a number of sources. Thermostable polymerases may be obtained, for example, from a variety of thermophilic bacteria that are commercially available (for example, from American Type Culture Collection, Rockville, Md.) using methods that are well-known to one of ordinary skill in the art (See, e.g., U.S. Pat. No. 6,245,533). Bacterial cells may be grown according to standard microbiological techniques, using culture media and incubation conditions suitable for growing active cultures of the particular species that are well-known to one of ordinary skill in the art (See, e.g., Brock, T. D., and Freeze, H., J. Bacteriol. 98(1):289-297 (1969); Oshima, T., and Imahori, K, Int. J. Syst. Bacteriol. 24(1):102-112 (1974)). Suitable for use as sources of thermostable polymerases are the thermophilic bacteria *Thermus aquaticus, Thermus thermophilus, Thermococcus litoralis, Pyrococcus furiosus, Pyrococcus woosii* and other species of the *Pyrococcus* genus, *Bacillus stearothermophilus, Sulfolobus acidocaldarius, Thermoplasma acidophilum, Thermus flavus, Thermus ruber, Thermus brockianus, Thermotoga neapolitana, Thermotoga maritima* and other species of the *Thermotoga* genus, and *Methanobacterium thermoautotrophicum*, and mutants of each of these species. Preferable thermostable polymerases can include, but are not limited to, Taq DNA polymerase, Tne DNA polymerase, Tma DNA polymerase, or mutants, derivatives or fragments thereof.

Various Sources and/or Preparation Methods of Nucleic Acids

Sources of nucleic acid samples in the disclosed compositions, methods and/or kits include, but are not limited to, human cells such as circulating blood, buccal epithelial cells, cultured cells and tumor cells. Also other mammalian tissue, blood and cultured cells are suitable sources of template nucleic acids. In addition, viruses, bacteriophage, bacteria, fungi and other micro-organisms can be the source of nucleic acid for analysis. The DNA may be genomic or it may be cloned in plasmids, bacteriophage, bacterial artificial chromosomes (BACs), yeast artificial chromosomes (YACs) or other vectors. RNA may be isolated directly from the relevant cells or it may be produced by in vitro priming from a suitable RNA promoter or by in vitro transcription. The present invention may be used for the detection of variation in genomic DNA whether human, animal or other. It finds particular use in the analysis of inherited or acquired diseases or disorders. A particular use is in the detection of inherited diseases.

In some embodiments, template sequence or nucleic acid sample can be gDNA. In other embodiments, the template sequence or nucleic acid sample can be cDNA. In yet other embodiments, as in the case of simultaneous analysis of gene expression by RT-PCR, the template sequence or nucleic acid sample can be RNA. The DNA or RNA template sequence or nucleic acid sample can be extracted from any type of tissue including, for example, formalin-fixed paraffin-embedded tumor specimens.

The following examples are intended to illustrate but not limit the invention.

EXAMPLES

I. General Assay Design:

The general schema for the cast-PCR assays used in the following examples is illustrated in FIG. 1. For each SNP that was analyzed, allele-specific primers were designed to target a first allele (i.e. allele-1) and a second allele (i.e. allele-2). The cast-PCR assay reaction mixture for allele-1 analysis included a tailed allele-1-specific primer (ASP1), one MGB allele-2 blocker probe (MGB2), one common locus-specific TaqMan probe (LST) and one common locus-specific primer (LSP). The cast-PCR assay reaction mixture for analysis of allele-2 included a tailed allele-2-specific primer (ASP2), one MGB allele-1 blocker probe (MGB1), one common locus-specific TaqMan probe (LST) and one common locus-specific primer (LSP).

II. Reaction conditions:

Each assay reaction mixture (10 µl total) contained 1× TaqMan Genotyping Master Mixture (Applied Biosystems, Foster City, Calif.; P/N 437135), 0.5 ng/µL genomic DNA or 1 million copies of plasmid DNA (as indicated), 300 nM (unless specified otherwise) tailed-, or in some cases untailed-, allele-specific primer (ASP1 for detection of allele-1 or ASP2 for detection of allele-2), 200 nM TaqMan probe (LST), 900 nM locus-specific primer (LSP), 150 nM allele-specific MGB blocker probe (MGB1 for detection of allele-2 or MGB2 for detection of allele-1). The reactions were incubated in a 384-well plate at 95° C. for 10 minutes, then for 5 cycles at 95° C. for 15 seconds each, then 58° C. for 1 minute, then by 45 cycles at 95° C. for 15 seconds each and then 60° C. for 1 minute. All reactions were run in duplicate or higher replication in an ABI PRISM 7900HT® Sequence Detection System, according to the manufacturer's instructions.

III. Nucleic Acid Samples:

Plasmids containing specific SNP sequences were designed and ordered from BlueHeron (Bothell, Wash.). (See Table 1 for a list of plasmids comprising SNPs used in the following examples.) The plasmids were quantified using TaqMan RNase P Assay (Applied Biosystems, Foster City, Calif.; P/N 4316838) according to the manufacturer's instructions and were used as templates (See Table 1, RNase P Control) to validate sensitivity, linear dynamic range, specificity, and selectivity of the given assays.

Genomic DNAs were purchased from Coriell Institute for Medical Research (Camden, N.J.; NA17203, NA17129, NA17201). The genotypes of target SNPs were validated with TaqMan SNP Genotyping Assays (Applied Biosystems, Foster City, Calif.; P/N 4332856) according to the manufacturer's instructions.

TABLE 1

| SNP ID | SEQUENCE |
| --- | --- |
| CV11201742 | GCTCTGCTTCATTCCTGTCTGAAGAAGGGCAGATAGTTT GGCTGCTCCTGTG[C/T]TGTCACCTGCAATTCTCCCTT ATCAGGGCCATTGGCCTCTCCCTTCTCTCTGTGAGGGAT ATTTTCTCTGACTTGTCAATCCACATCTTCC |
| CV11349123 | GGCTTGCAATGGCTCCAACCGGAAGGGCGGTGCTCGAGC TGTGGTGCGTGC[C/T]GCTAAGTTGTGCGTTCCAGGGT GCACTCGC |
| CV1207700 | GCAACTATACCCTTGATGGATGGAGATTTA[C/T]GCAA TGTGTTTTACTGGGTAGAGTGACAGACCTT |
| CV25594064 | CCTGAACTTATTTGGCAAGAGCGATGAGTACTCTTAAAA TTACTATCTGGAAATTATATTATTTAGAATCTGCCAATT ACCTAGATCCCCCCT[C/G]AACAATTGTTTCACCAAGG AACTTCCTGAA |
| CV25639181 | GAATTGGTTGTCTCCTTATGGGAACTGGAAGTATTTTGA CA[G/T]CTTTACCACATTTCTTCATGGGATAGTAAGTG TTAAACAGCTCTGAGCCATTTATTATCAGCTACTTGTAA ATTAGCAGTAGAATTTTATTTTTATACTTGTAAGTGGGC AGTTACCTTTTGAGAGGAATACCTATAG |
| RNaseP Control | GCGGAGGGAAGCTCATCAGTGGGGCCACGAGCTGAGTGC GTCCTGTCACTCCACTCCCATGTCCCTTGGGAAGGTCTG AGACTAGGG |
| BRAF-1799TA | TACTACACCTCAGATATATTTCTTCATGAAGACCTCACA GTAAAAATAGGTGATTTTGGTCTAGCTACAG[T/A]GAA ATCTCGATGGAGTGGGTCCCATCAGTTTGAACAGTTGTC TGGATCCATTTTGTGGATGGTAAGAATTGAGGCTATTTT TCCACTGATTAAATTTTTGGCCCTGAGATGCTGCTGAGT T |
| CTNNB1-121AG | TGCTAATACTGTTTCGTATTTATAGCTGATTTGATGGAG TTGGACATGGCCATGGAACCAGACAGAAAAGCGGCTGTT AGTCACTGGCAGCAACAGTCTTACCTGGACTCTGGAATC CATTCTGGTGCCACT[A/G]CCACAGCTCCTTCTCTGAG TGGTAAAGGCAATCCTGAGGAAGAGGATGTGGATACCTC CCAAGTC |
| CTNNB1-134CT | TTTGATGGAGTTGGACATGGCCATGGAACCAGACAGAAA AGCGGCTGTTAGTCACTGGCAGCAACAGTCTTACCTGGA CTCTGGAATCCATTCTGGTGCCACTACCACAGCTCCTT [C/T]TCTGAGTGGTAAAGGCAATCCTGAGGAAGAGGAT GTGGATACCTCCCAAGTCCTGTATGAGTGGGAA |
| EGFR-2369CT | GTGGACAACCCCCACGTGTGCCGCCTGCTGGGCATCTGC CTCACCTCCACCGTGCAGCTCATCA[C/T]GCAGCTCAT GCCCTTCGGCTGCCTCCTGGACTATGTCCGGGAACACAA AGACAATATTGGCTCCCAGTACCTGCTCAACTGGTGTGT GCAGATCGCAAAGGTAATCAGGGAAGGGA |
| EGFR-2573TG | GCATGAACTACTTGGAGGACCGTCGCTTGGTGCACCGCG ACCTGGCAGCCAGGAACGTACTGGTGAAAACACCGCAGC ATGTCAAGATCACAGATTTTGGGC[T/G]GGCCAAACTG CTGGGTGCGGAAGAGAAAGAATACCATGCAGAAGGAGGC AAAGTAAGGAGGTG |
| KRAS-176CG | CAGGATTCCTACAGGAAGCAAGTAGTAATTGATGGAGAA ACCTGTCTCTTGGATATTCTCGACACAG[C/G]AGGTCA AGAGGAGTACAGTGCAATGAGGGACCAGTACATGAGGAC TGGGGAGGGCTTTCTTTGTGTATTTGCCATAAATAATAC TAAATCATTTGAAGATATTC |
| KRAS-183AC | ACAGGAAGCAAGTAGTAATTGATGGAGAAACCTGTCTCT TGGATATTCTCGACACAGCAGGTCA[A/C]GAGGAGTAC AGTGCAATGAGGGACCAGTACATGAGGACTGGGGAGGGC TTTCTTTGTGTATTTGCCATAAATAATACTAAATCATTT GAAGATATTCACCATTATAGGTGGGTTTAAATTGAATAT AATAAGCTGACATTAA |
| KRAS-34GA | TATTAACCTTATGTGTGACATGTTCTAATATAGTCACAT TTTCATTATTTTTATTATAAGGCCTGCTGAAAATGACTG AATATAAACTTGTGGTAGTTGGAGCT[G/A]GTGGCGTA GGCAAGAGTGCCTTGACGATACAGCTAATTCAGAATCAT TTTGTGGACGAATATGA |
| KRAS-35GA | TATTAACCTTATGTGTGACATGTTCTAATATAGTCACAT TTTCATTATTTTTATTATAAGGCCTGCTGAAAATGACTG AATATAAACTTGTGGTAGTTGGAGCTG[G/A]TGGCGTA GGCAAGAGTGCCTTGACGATACAGCTAATTCAGAATCAT TTTGTGGACGAATATGATC |
| KRAS-38GA | CATTATTTTTATTATAAGGCCTGCTGAAAATGACTGAAT ATAAACTTGTGGTAGTTGGAGCTGGTG[G/A]CGTAGGC AAGAGTGCCTTGACGATACAGCTAATTCAGAATCATTTT GTGGACGAATATGATCCAACAATAGAGGTAAATCTTGTT TTAATATGCATATTACTGGTGCAGGACCATTCTTTGATA CAGATAAAGGTTTCTCTGACCATTTTCATGAGTACTTAT |

TABLE 1-continued

| SNP ID | SEQUENCE |
|---|---|
| NRAS-181CA | ATTCTTACAGAAAACAAGTGGTTATAGATGGTGAAACCT GTTTGTTGGACATACTGGATACAGCTGGA[C/A]AAGAA GAGTACAGTGCCATGAGAGACCAATACATGAGGACAGGC GAAGGCTTCCTCTGTGTATTTGCCATCAATAATAGCAAG TCATTTGCGGATATTAACCTCTACAGGTACTAGGAGCAT TATTTTCTCTGAAAGGATG |
| NRAS-183AT | TTACAGAAAACAAGTGGTTATAGATGGTGAAACCTGTTT GTTGGACATACTGGATACAGCTGGACA[A/T]GAAGAGT ACAGTGCCATGAGAGACCAATACATGAGGACAGGCGAAG GCTTCCTCTGTGTATTTGCCATCAATAATAGCAAGTCAT TTGCGGATATTAACCTCTACAGGTACTAGGAGCATTATT TTCTCTGAAAGGATG |
| NRAS-35GA | TGGTTTCCAACAGGTTCTTGCTGGTGTGAAATGACTGAG TACAAACTGGTGGTGGTTGGAGCAG[G/A]TGGTGTTGG GAAAAGCGCACTGACAATCCAGCTAATCCAGAACCACTT TGTAGATGAATATGATCCCACCATAGAGGTGAGGCCCAG TGGTAGCCCG |
| NRAS-38GA | TTTCCAACAGGTTCTTGCTGGTGTGAAATGACTGAGTAC AAACTGGTGGTGGTTGGAGCAGGTG[G/A]TGTTGGGAA AAGCGCACTGACAATCCAGCTAATCCAGAACCACTTTGT AGATGAATATGATCCCACCATAGAGGTGAGGCCCAGTGG TAGCCC |
| TP53-524GA | GGCACCCGCGTCCGCGCCATGGCCATCTACAAGCAGTCA CAGCACATGACGGAGGTTGTGAGGC[G/A]CTGCCCCCA CCATGAGCGCTGCTCAGATAGCGATGGTGAGCAGCTGGG GCTGGAGAGACGACAGGGCTGGTTGCCCAGGGTCCCCAG GCCTCTGATTCCTCACTGATTGCTCTTAGGTCTGGCC |
| TP53-637CT | CCTCCTCAGCATCTTATCCGAGTGGAAGGAAATTTGCGT GTGGAGTATTTGGATGACAGAAACACTTTT[C/T]GACA TAGTGTGGTGGTGCCCTATGAGCCGCCTGAGGTCTGGTT TGCAACTGGGGTCTCTGGGAGGAGGGGTTAAGGGTGGTT GTCAGTGGCCCTC |
| TP53-721TG | CTTGGGCCTGTGTTATCTCCTAGGTTGGCTCTGACTGTA CCACCATCCACTACAACTACATGTGTAACAGT[T/G]CC TGCATGGGCGGCATGAACCGGAGGCCCATCCTCACCATC ATCACACTGGAAGACTCCAGGTCAGGAGCCACTTGCCAC CCTGCACACTGGCCTGCTGTGCCCCAGCCTC |
| TP53-733GA | TAGGTTGGCTCTGACTGTACCACCATCCACTACAACTAC ATGTGTAACAGTTCCTGCATGGGC[G/A]GCATGAACCG GAGGCCCATCCTCACCATCATCACACTGGAAGACTCCAG GTCAGGAGCCACTTGCCACCCTGCACACTGGCCTGCTGT GCCCCAGCCTC |
| TP53-742CT | CTGACTGTACCACCATCCACTACAACTACATGTGTAACA GTTCCTGCATGGGCGGCATGAAC[C/T]GGAGGCCCATC CTCACCATCATCACACTGGAAGACTCCAGGTCAGGAGCC ACTTGCCACCCTGCACACTGGCCTGCTGTGCCCCAGCCT CTGCTTGCCTC |
| TP53-743GA | TGACTGTACCACCATCCACTACAACTACATGTGTAACAG TTCCTGCATGGGCGGCATGAACC[G/A]GAGGCCCATCC TCACCATCATCACACTGGAAGACTCCAGGTCAGGAGCCA CTTGCCACCCTGCACACTGGCCTGCTGTGCCCCAGCCTC TGCTTGCCTC |
| TP53-817CT | CCTCTTGCTTCTCTTTTCCTATCCTGAGTAGTGGTAATC TACTGGGACGGAACAGCTTTGAGGTG[C/T]GTGTTTGT GCCTGTCCTGGGAGAGACCGGCGCACAGAGGAAGAGAAT CTCCGCAAGAAAGGGGAGCCTCACCACGAGCTGCCCCCA GGGAGCACTAAGCGAGGTAAGCAA |

Data Analysis:

An automatic baseline and manual threshold of 0.2 were used to calculate the threshold cycle ($C_t$) which is defined as the fractional cycle number at which the fluorescence passes the fixed threshold. The ΔCt between amplification reactions for matched vs. mismatched sequences is defined as the specificity of cast-PCR ($\Delta Ct = Ct_{mismatch} - Ct_{match}$). The larger the ΔCt between mismatched and matched targets, the better assay specificity. The $2^{\Delta Ct}$ value was used to estimate the power of discrimination (or selectivity) which is equal to $\frac{1}{2}^{\Delta Ct}$ or, in some cases, calculated as % ($\frac{1}{2}^{\Delta Ct} \times 100$).

Example 1

Tailed Primers Improve Discrimination of Allelic Variants

The following example demonstrates that the application of allele-specific primers comprising tails significantly improves the discrimination of allelic variants.

In conventional AS-PCR, the discrimination of 3' nucleotide mismatches is largely dependent on the sequence surrounding the SNP and the nature of the allele. The ΔCT between the amplification reactions for matched and mismatched primers varies. To improve the discrimination between the amplification of matched and mismatched sequences, allele-specific primers were designed to comprise tails at their 5' termini and then tested for their suitability in AS-PCR assays.

Assays were performed using the general experimental design and reaction conditions indicated above (with the exception that no blocker probes were included), using 0.5 ng/uL genomic DNA containing the hsv11711720 SNP comprising one of three alleles (A, C, or T) as the nucleic acid template (see Table 2). The three genotypes are indicated in Table 2a. Primers and probes were designed according to the sequences shown in Table 3.

TABLE 2

Genomic DNA Sequence for hsv11711720 SNP (target alleles are indicated in brackets).

AGAAAATAACTAAGGGAAGGAGGAAAGTGGGGAGGAAGGAAGAACAGTGT

GAAGACAATGGCCTGAAAACTGAAAAAGTCTGTTAAAGTTAATTATCAGT

TTTTGAGTCCAAGAACTGGCTTTGCTACTTTCTGTAAGTTTCTAATTTAC

TGAATAAGCATGAAAAAGATTGCTTTGAGGAATGGTTATAAACACATTCT

TAGAGCATAGTAAGCAGTAGGGAGTAACAAAATAACACTGATTAGAATAC

TTTACTCTACTTAATTAATCAATCATATTTAGTTTGACTCACCTTCCCAG

[A/C/T]ACCTTCTAGTTCTTTCTTATCTTTCAGTGCTTGTCCAGACAAC

ATTTTCATTTCAACAACTCCTGCTATTGCAATGATGGGTACAATTGCTAA

GAGTAACAGTGTTAGTTGCCAACCATAGATGAAGGATATAATTATTCCTG

TCCCAAGATTTGCTATATTCTGGGTAATTACAGCAAGCCTGGAACCTATA

GCCTGCAAAACAAAACAAATTAGAGAAATTTTAAAAATATTATCTTCACA

ACTCATGCTTCTATTTTCTGAAAACTCACCTTCATGAGACTATATTCATT

ATTTTAT

TABLE 2a

Genotypes of Genomic DNA Sequence for hsv11711720 SNP

| Genomic DNA ID | Genotype |
|---|---|
| NA17203 | AA |
| NA17129 | CC |
| NA17201 | TT |

Table 3: List and Sequences of Primers and Probes: conventional allele-specific primers ("ASP-tail"); tailed allele-specific primers ("ASP"); locus-specific TaqMan probe (LST); locus-specific primer (LSP). The nucleotides shown in lower case are the tailed portion of the primers. The nucleotide-specific portion of each allele-specific primer is at the 3'-most terminus of each primer (indicated in bold).

TABLE 3

| Primer/<br>Probe ID | Sequence (5' to 3') | Tm<br>(° C.) |
|---|---|---|
| 17129-ASP | ATATTTAGTTTGACTCACCTTCCCAGC | 63.2 |
| 17129-tailASP | accACTCACCTTTCCCAGC | 63.0 |
| 17203-ASP | ATATTTAGTTTGACTCACCTTCCCAGA | 62.0 |
| 17203-tailASP | accACTCACCTTTCCCAGA | 63.7 |
| 17201-ASP | ATATTTAGTTTGACTCACCTTCCCAGT | 62.2 |
| 17201-tailASP | accACTCACCTTTCCCAGT | 64.0 |
| LST | (6-FAM)-TGGACAAGCACTGAAAGA-(MGB) | 67.4 |
| LSP | GCAGGAGTTGTTGAAATGAAAATGTTG | 62.5 |

As shown in Table 4, when using non-tailed ASPs ("ASP-tail"), the discrimination of 3' nucleotide mismatch is largely dependent on the nature of the allele, as a considerable range of ΔCt values is observed depending on the identity of the 3' terminal base. The range of ΔCt values between matched and mismatched nucleotides ("NT") were from −0.1 to 10. However, with tailed ASPs, the discrimination of 3' nucleotide mismatch was significantly improved. In fact, as Table 4 shows, the ΔCt value between matched and mismatched nucleotides was consistently equal to or greater than 10 when tailed ASPs were used. The Ct values for amplification of matched sequences using tailed ASPs were comparable to those using conventional or non-tailed ASPs. These results indicate that tailed ASP, can improve the specificity of AS-PCR, but may not improve the sensitivity of detection.

Table 4: Tailed allele-specific primers ("ASP") significantly improve discrimination of allelic variants. The specificity ("fold difference") was calculated based on the difference between Ct values using tailed vs. untailed primers ($2^{(\Delta Ct(ASP) - \Delta Ct(ASP-tail))}$). The mismatched nucleotides of the 3' allele-specific nucleotide portion of the ASPs (+/− tail) and the target allele are also indicated ("NT mismatch").

TABLE 4

| NT mismatch | ΔCt (ASP-tail) | ΔCt (ASP) | Specificity Improvement (fold difference) |
|---|---|---|---|
| CA | 0.9 | 11.5 | 1552.1 |
| CT | 1.2 | 11.5 | 1278.3 |
| AC | 10.0 | 11.9 | 3.7 |
| AG | 9.8 | 11.9 | 4.3 |
| TG | 2.3 | 11.5 | 588.1 |
| TC | −0.1 | 11.5 | 3104.2 |
| Average | 4.0 | 11.6 | 1088.5 |

Example 2

Low Primer Concentrations Improve Discrimination of Allelic Variants

Assays were performed using the general experimental design and reaction conditions indicated above, in the presence of 1 million copies of plasmid DNA containing various SNP target sequences (see Table 1) and 200 nM or 800 nM tailed ASP (as indicated). Assay primers and probes were designed according to the sequences shown in FIGS. 11A-D.

The effect of tailed ASP concentration on discrimination of allelic variants is summarized in Table 5. The ΔCt between the amplification reactions for matched and mismatched primers demonstrate that lower tailed ASP concentrations improve discrimination of allelic variants.

TABLE 5

Assay Results Using Different Concentrations of Tailed Allele-specific Primers

| Plasmid SNP ID | ΔCt (ASP @ 800 nM) | ΔCt (ASP @ 200 nM) | Specificity Improvement (fold difference) |
|---|---|---|---|
| CV11201742 | 14.1 | 15.2 | 2.14 |
| CV11349123 | 8.2 | 10 | 3.48 |
| CV1207700 | 5.2 | 6.6 | 2.64 |
| CV25594064 | 20.1 | 19.1 | 0.5 |
| CV25639181 | 11.9 | 12.9 | 2 |
| Average | 12.6 | 13.44 | 2.14 |

Example 3

Primers Designed with Reduced Tms Improves Discrimination of Allelic Variants

Assays were performed using the general experimental design and reaction conditions indicated above, in the presence of 1 million copies of plasmid DNA containing various SNP target sequences (see Table 1) using tailed ASP with a higher Tm (~57° C.) or tailed ASP with a lower Tm (~53° C.). Assay primers and probes were designed according to the sequences shown in FIGS. 11A-D.

The effect of allele-specific primer Tm on discrimination of allelic variants is summarized in Table 6. The ΔCt of allele-specific primers with a lower Tm are significantly higher than those of allele-specific primers with a higher Tm. Allele-specific primers designed with reduced Tms improved discrimination of allelic variants by as much as 118-fold in some cases or an average of about 13-fold difference.

TABLE 6

ΔCt Values Using Tailed ASPs with Lower Tm (~53° C.) or with Higher Tm (~57° C.)

| Plasmid SNP ID | ΔCt (ASP w/ Tm ~57° C.) | ΔCt (ASP w/ Tm ~53° C.) | Specificity Improvement (fold difference) |
|---|---|---|---|
| BRAF-1799TA | 12.2 | 19.1 | 118.9 |
| CTNNB1-121AG | 11.6 | 14.9 | 10.0 |
| KRAS-176CG | 18.8 | 22.5 | 13.1 |
| NRAS-35GA | 13.0 | 14.0 | 1 |
| TP53-721TG | 14.7 | 19.1 | 20.6 |
| CTNNB1-134CT | 8.6 | 14.1 | 44.8 |
| EGFR-2369CT | 9.7 | 10.7 | 2 |

TABLE 6-continued

ΔCt Values Using Tailed ASPs with Lower Tm (~53° C.) or with Higher Tm (~57° C.)

| Plasmid SNP ID | ΔCt (ASP w/ Tm ~57° C.) | ΔCt (ASP w/ Tm ~53° C.) | Specificity Improvement (fold difference) |
|---|---|---|---|
| KRAS-183AC | 22.2 | 23.1 | 1.8 |
| NRAS-38GA | 14.0 | 14.3 | 1.2 |
| TP53-733GA | 13.6 | 13.5 | 1.0 |
| EGFR-2573TG | 16.7 | 20.2 | 10.9 |
| KRAS-34GA | 14 | 14.8 | 1.8 |
| KRAS-38GA | 11.2 | 14.4 | 8.9 |
| NRAS-181CA | 24.0 | 27.1 | 8.6 |
| TP53-742CT | 9.1 | 8.0 | 0.5 |
| KRAS-35GA | 11.5 | 15.1 | 12.3 |
| NRAS-183AT | 23.6 | 22.7 | 0.5 |
| TP53-524GA | 11.4 | 13.5 | 4.6 |
| TP53-637CT | 11.4 | 14.4 | 7.8 |
| TP53-743GA | 10.1 | 13.2 | 8.4 |
| TP53-817CT | 13.6 | 13.9 | 1.2 |
| Average | 14.1 | 16.3 | 13.3 |

Example 4

Use of Blocker Probes Improves Discrimination of Allelic Variants

The following example illustrates that the use of MGB blocker probes improves the discrimination between 3' nucleotide mismatched and matched primers to target sequences in PCR reactions.

Assays were performed using the general cast-PCR schema and reaction conditions indicated above, using 1 million copies of plasmid DNA containing various SNP target sequences (see Table 1) in the presence of MGB blocker probes or in the absence of MGB blocker probes. Assay primers and probes were designed according to the sequences shown in FIGS. 11A-D.

To improve the selectivity of AS-PCR, blocker probes were synthesized to comprise an MGB group at their 3' terminus. (See, for example, Kutyavin, I. V., et al., Nucleic Acids Research, 2000, Vol. 28, No. 2: 655-661, U.S. Pat. Nos. 5,512,677; 5,419,966; 5,696,251; 5,585,481; 5,942,610 and 5,736,626.)

The results of cast-PCR using MGB blocker probes are summarized in Table 7. The ΔCt between cast-PCR with MGB blocker probes is larger than that without MGB blocker probes. As shown, MGB blocker probes improve the discrimination of allelic variants.

TABLE 7

MGB Blocker Probes Improve Discrimination of Allelic Variants

| SNP ID | ΔCt (no MGB blocker) | ΔCt (+MGB blocker) | Specificity Improvement (fold difference) |
|---|---|---|---|
| BRAF-1799TA | 11.4 | 14.9 | 11.5 |
| CTNNB1-121AG | 11.6 | 14.1 | 5.4 |
| KRAS-176CG | 17.8 | 20.9 | 9 |
| NRAS-35GA | 13.9 | 14.3 | 1.4 |
| TP53-721TG | 12.5 | 14.7 | 4.4 |
| CTNNB1-134CT | 6.7 | 10.2 | 11.6 |
| EGFR-2369CT | 7.7 | 10.1 | 5.3 |
| KRAS-183AC | 22.4 | 23 | 1.5 |
| NRAS-38GA | 14.5 | 14.6 | 1.1 |
| TP53-733GA | 13.2 | 14.4 | 2.3 |
| EGFR-2573TG | 18.2 | 21.8 | 11.6 |
| KRAS-34GA | 14.4 | 15.1 | 1.7 |
| KRAS-38GA | 11.9 | 15.1 | 1.7 |
| NRAS-181CA | 19.3 | 24.2 | 30.2 |
| TP53-742CT | 12.7 | 13.6 | 1.9 |
| KRAS-35GA | 11.0 | 13.7 | 6.5 |
| NRAS-183AT | 20.2 | 21.7 | 2.9 |
| TP53-524GA | 13.5 | 13.5 | 1 |
| TP53-637CT | 9.3 | 12.1 | 7.0 |
| TP53-743GA | 9.9 | 11.5 | 3.1 |
| TP53-817CT | 12.6 | 13.2 | 1.5 |
| Average | 13.6 | 15.5 | 6.0 |

Example 5

Primers Designed to Target Discriminating Bases Improves Discrimination of Allelic Variants Assays were performed using the general cast-PCR schema and reaction conditions indicated above, in the presence of 1 million copies of plasmid DNA containing SNP target sequences (see Table 1). Assay primers and probes were designed according to the sequences shown in FIGS. 11A-D.

According to the data summarized in Table 8, the discrimination of cast-PCR was dependent on the nature of the allele being analyzed. As Table 8 indicates, the ΔCt between mismatched and matched sequences for allele-1 were different from ΔCt between mismatched and matched sequences for allele-2. However, both A and G bases, as compared to a T base, were highly discriminating for allele-1 and allele-2 in all four SNPs examined.

TABLE 8

Primers Designed to Target Discriminating Bases Improve Discrimination of Allelic Variants

| | ASP design | | SNP allele-1 | | | SNP allele-2 | | |
|---|---|---|---|---|---|---|---|---|
| SNP ID | 3' NT of ASP 1 | 3' NT of ASP 2 | Allele NT | ΔCt (Ct_mismatch-Ct_match) | Specificity (fold difference) | Allele NT | ΔCt (Ct_mismatch-Ct_match) | Specificity (fold difference) |
| KRAS-38GA | G | A | C | 13.4 | 10809 | T | 8.2 | 294 |
| NRAS-181CA | C | A | G | 27.5 | 189812531 | T | 9.8 | 891 |

TABLE 8-continued

Primers Designed to Target Discriminating Bases Improve Discrimination of Allelic Variants

| | ASP design | | | SNP allele-1 | | | SNP allele-2 | |
|---|---|---|---|---|---|---|---|---|
| SNP ID | 3' NT of ASP 1 | 3' NT of ASP 2 | Allele NT | ΔCt (Ct_mismatch-Ct_match) | Specificity (fold difference) | Allele NT | ΔCt (Ct_mismatch-Et_match) | Specificity (fold difference) |
| NRAS-183AT | A | T | T | 17.9 | 244589 | A | 23.4 | 11068835 |
| TP53-742CT | C | T | G | 12.3 | 5043 | A | 8.3 | 315 |

Example 6

Determination of the Sensitivity and Dynamic Range for Cast-PCR

In this example, the sensitivity and dynamic range of cast-PCR was determined by performing cast-PCR using various copy numbers of a target plasmid.

Assays were performed using the general cast-PCR schema and reaction conditions indicated above, using $1 \times 10^0$ (1 copy) to $1 \times 10^7$ copies of plasmid DNA containing the NRAS-181CA SNP target sequence (see Table 1). Assay primers and probes were designed according to the sequences shown in FIGS. 11A-D.

Figure 5A:
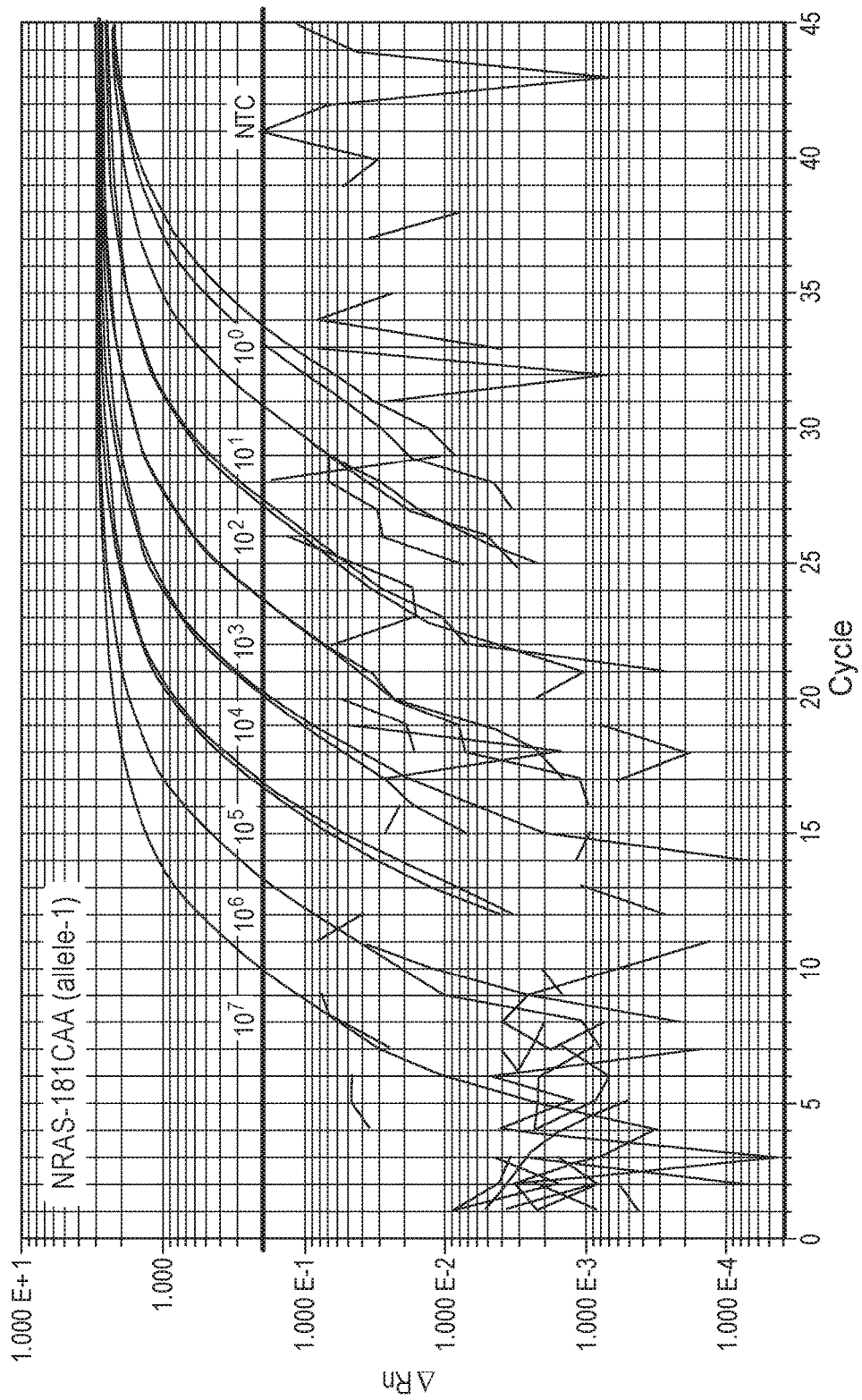
FIGS. 5A-5B depict the TaqMan-like sensitivity and dynamic range of one exemplary embodiment of cast-PCR.
Figure 5B:
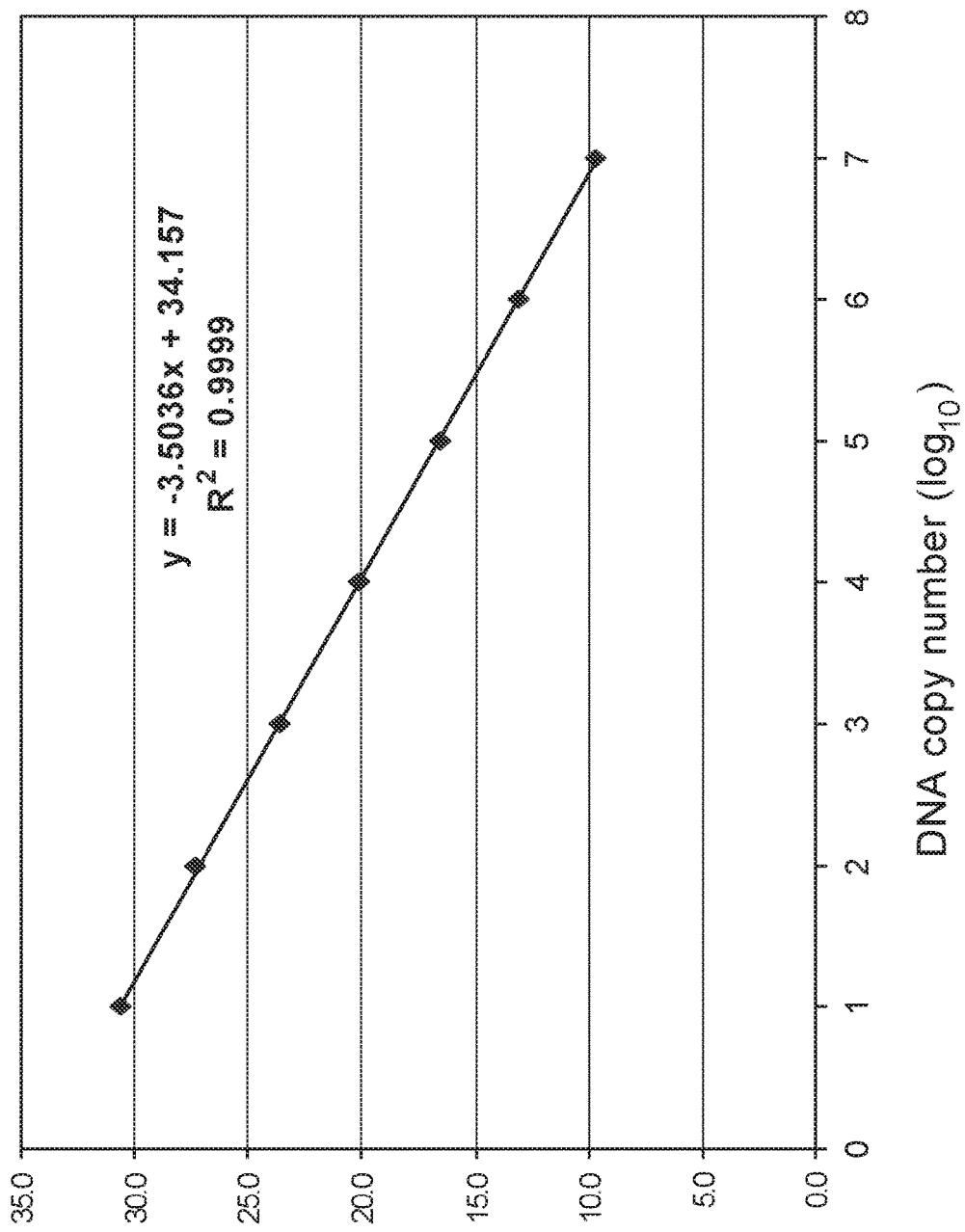

As shown in FIGS. 5A-5B, the use of tailed primers and MGB-blocker probes does not adversely affect the sensitivity of cast-PCR, as the sensitivity of cast-PCR is comparable to TaqMan assays which do not utilize tailed primers or blocker probes. Furthermore, FIGS. 5A-5B shows that the cast-PCR assay shows a linear dynamic range over at least 7 logs.

Example 7

Determination of the Specificity of Cast-PCR

In this example, the specificity of cast-PCR was determined by comparing the amplification of particular alleles of KRAS using either matched or mismatched ASPs to a given allele in the presence of their corresponding blocker probes.

Assays were performed using the general cast-PCR schema and reaction conditions indicated above, using $1 \times 10^6$ copies of plasmid DNA containing either one of two alleles of the NRAS-181CA SNP target sequence (see Table 1). Assay primers and probes were designed according to the sequences shown in FIGS. 11A-D.

Figure 7A:
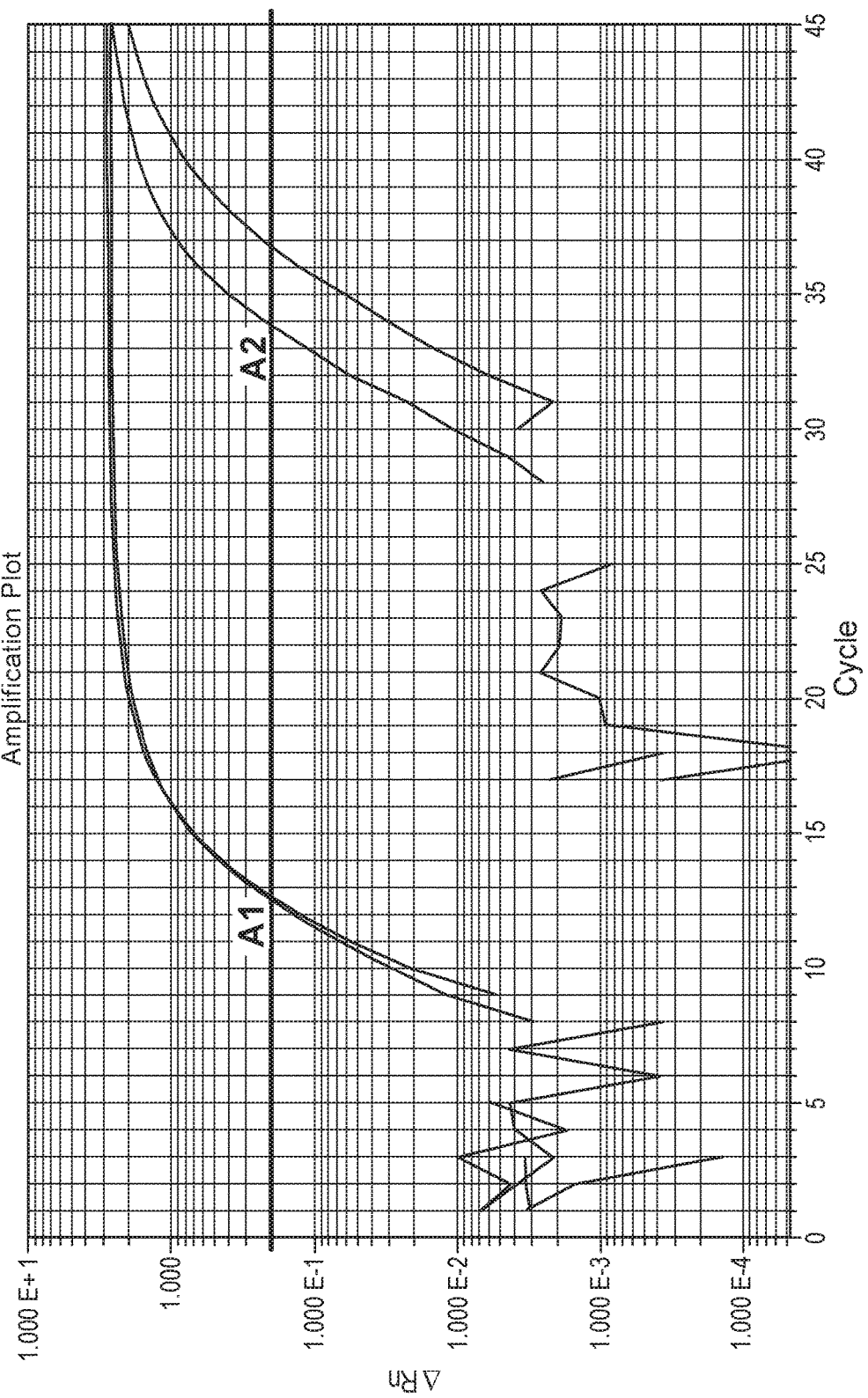
Figure 7B:
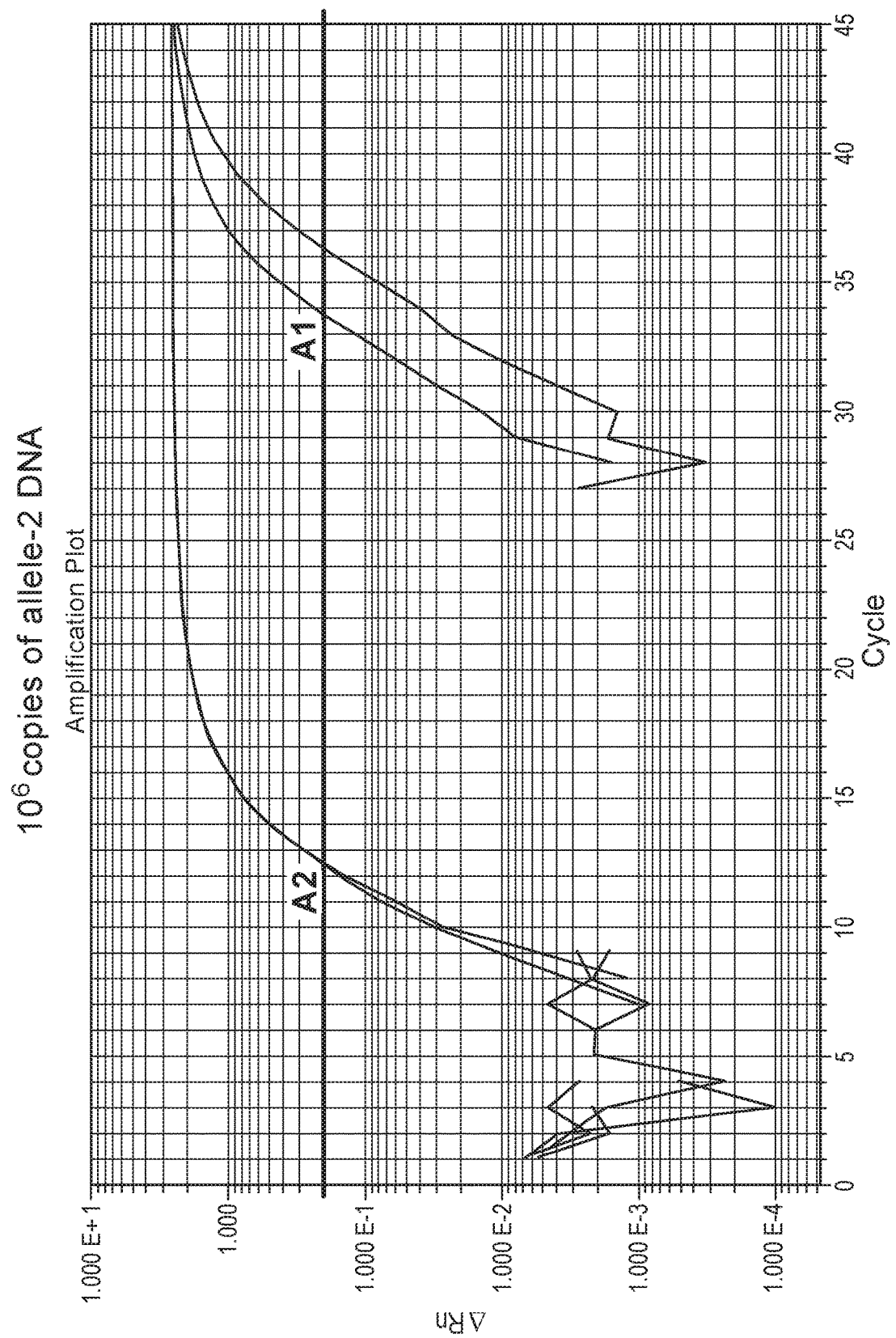

FIG. 7A shows the an amplification plot of cast-PCR on allele-1 DNA using matched (A1) primers in the presence of A2 blocker probes or mismatched (A2) primers in the presence of A1 blocker probes. FIG. 7B shows a similar experiment in which cast-PCR was performed on allele-2 DNA. As indicated in the data summary in FIG. 7C, a robust ΔCt values of over 20 were observed for cast-PCR on both alleles of KRAS-183AC tested. This corresponds to a specificity as determined by a calculation of $2^{\Delta Ct}$ of $9 \times 10^6$, and $2 \times 10^6$, respectively, for alleles A1 and A2. Furthermore, a calculation of selectivity ($\frac{1}{2}^{\Delta Ct}$) indicates that values of $1/1.1 \times 10^7$ and $1/5.0 \times 10^7$ are observed for alleles A1 and A2, respectively.

Example 8

Cast-PCR is Able to Detect a Single Copy Mutant DNA in One Million Copies of Wild Type DNA In this example, the selectivity of cast-PCR, i.e., the ability of cast-PCR to detect a rare mutant DNA in an excess of wild type DNA, was determined.

Assays were performed using the general cast-PCR schema and reaction conditions indicated above, using various copy numbers of mutant KRAS-183AC plasmid DNA (1 copy to $1 \times 10^6$ copies) mixed with $1 \times 10^6$ copies of wild type KRAS-183AC plasmid DNA (see Table 1). Assay primers and probes were designed according to the sequences shown in FIGS. 11A-D, and cast-PCR reactions were performed using wild type or mutant ASP and corresponding MGB blocker probes.

Figure 8:
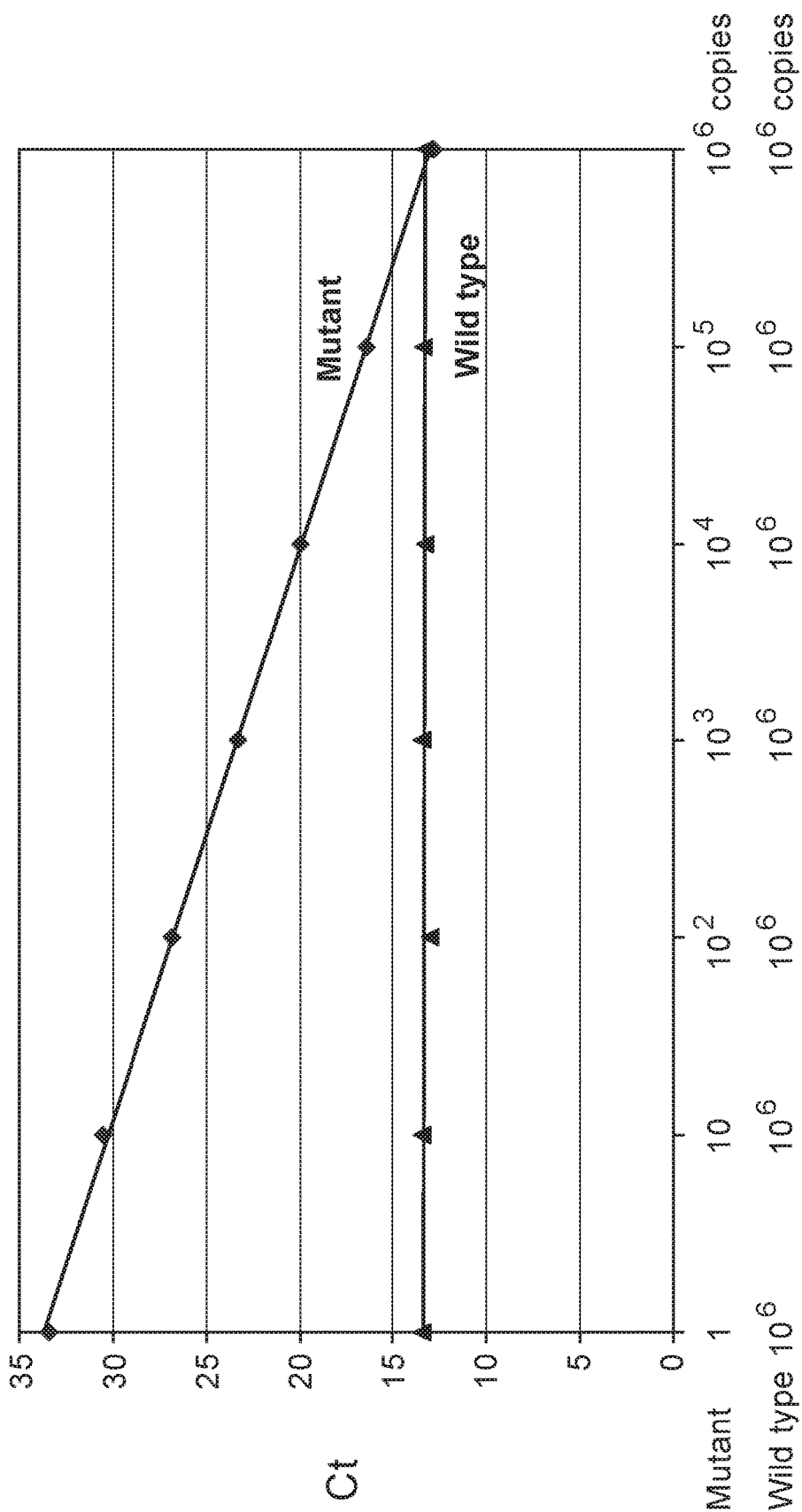
FIG. 8 depicts one exemplary embodiment using cast-PCR methods to detect a single copy of mutant DNA in $10^6$ copies of wild-type DNA.

FIG. 8 shows that cast-PCR is able to detect as little as one copy of a mutant DNA sequence, even when surrounded by a million-fold excess of a wild type sequence.

Example 9

Selectivity of Cast-PCR in Discriminating Tumor Cell DNA from Normal Cell DNA

In this example, the selectivity of cast-PCR was determined by performing assays on samples in which various amounts of tumor cell genomic DNA were mixed with or "spiked" into genomic DNA from normal cells. DNA samples were extracted using QIAmp DNA Mini Prep Kits (Qiagen). Wild type DNA was extracted from the SW48 cell line and mutant DNA was extracted the H1573 cell line.

The mutant DNA contained the KRAS-G12A mutation. The percentage of tumor cell DNA in the spiked samples varied from 0.5 to 100%. cast-PCR was used to detect the presence of tumor cell DNA when present in these percentages.

Assays were performed using the general cast-PCR schema and reaction conditions indicated above, using 30 ng of gDNA per reaction. Assay primers and probes were designed according to the sequences corresponding to KRAS-G12A SNP ID, as shown in FIGS. 11A-D.

Figure 9:
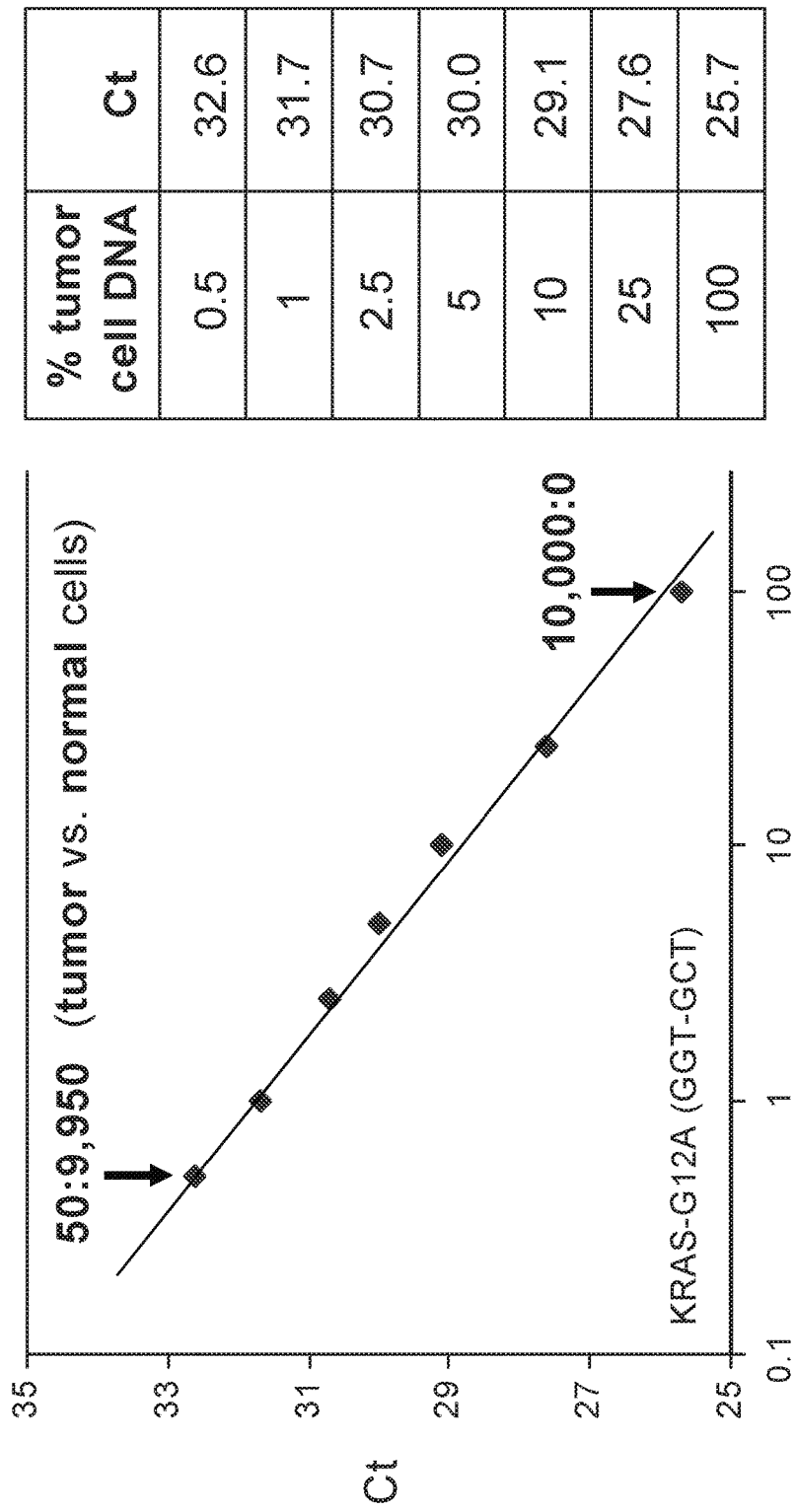
FIG. 9 depicts detection of the relative copy number of mutant samples (KRAS-G12A) spiked in wild type samples using cast-PCR methods.

As shown in FIG. 9, tumor cell DNA, even when present only at a level of 0.5% as compared to normal cell DNA, is easily detected using cast-PCR.

Example 10

Use of Cast-PCR to Detect Tumor Cells in Tumor Samples

In this example, cast-PCR was used to detect and determine the percentage of tumor cells in tumor samples.

Various normal and tumor samples were obtained and assayed by cast-PCR for the presence of a number of SNPs associated with cancer as shown in FIG. 10.

Assays were performed using the general cast-PCR schema and reaction conditions indicated above, using 5 ng of gDNA or 1.5 ng cDNA derived from either normal or tumor samples. Assay primers and probes corresponding to the SNPs shown in FIG. 10 were designed according to the sequences as shown in FIGS. 11A-D.

The results shown in FIG. 10 indicate that cast-PCR has a low false positive rate as indicated by the failure of cast-PCR to detect the presence of mutant cells in normal samples. In contrast, cast-PCR was able to provide a determination of the percentage of tumor cells in various tumor samples that ranged from just under 2% for a tumor sample containing the NRAS-183AT SNP to 80% for a sample containing the EGFR-2573TG SNP.

It is noted that, as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

The section headings used herein are for organizational purposes only and are not to be construed as limiting the subject matter described. All documents, or portions of documents, cited in this application, including but not limited to patents, patent applications, articles, books, and treatises are hereby expressly incorporated by reference in their entirety for any purpose. In the event that one or more of the incorporated documents defines a term that contradicts that term's definition in this application, this application controls.

All references cited herein, including patents, patent applications, papers, text books, and the like, and the references cited therein, to the extent that they are not already, are hereby incorporated by reference in their entirety. In the event that one or more of the incorporated literature and similar materials differs.

We claim:

1. A method for detecting a first allelic variant of a target sequence in a nucleic acid sample suspected of comprising at least a second allelic variant of the target sequence, comprising:
   a) forming a reaction mixture by combining:
      i. the nucleic acid sample;
      ii. a first allele-specific primer, wherein an allele-specific nucleotide portion of the first allele-specific primer is complementary to the first allelic variant of the target sequence;
      iii. a first allele-specific blocker probe that is complementary to a region of the target sequence comprising the second allelic variant, wherein said region encompasses a position corresponding to a binding position of the allele-specific nucleotide portion of the first allele-specific primer, and wherein the first allele-specific blocker probe comprises a minor groove binder;
      iv. a first locus-specific primer that is complementary to a region of the target sequence that is 3' from the first allelic variant and on the opposite strand; and
      v. a first detector probe;
   b) carrying out an amplification reaction on the reaction mixture using the first locus-specific primer and the first allele-specific primer to form a first amplicon; and
   c) detecting the first amplicon by detecting a change in a detectable property of the first detector probe, thereby detecting the first allelic variant of the target sequence in the nucleic acid sample.

2. The method of claim 1, further comprising using the change in a detectable property of the first detector probe to quantitate the first allelic variant.

3. A composition comprising:
   a) an allele-specific primer, wherein an allele-specific nucleotide portion of the allele-specific primer is complementary to a first nucleic acid molecule, the first nucleic acid molecule comprising a target allele;
   b) an allele-specific blocker probe that is complementary to a second nucleic acid molecule, the second nucleic acid molecule comprising an alternative allele, wherein the alternative allele corresponds to the same loci as the target allele, and wherein the first allele-specific blocker probe comprises a minor groove binder;
   c) a locus-specific detector probe complementary to the first nucleic acid molecule; and
   d) a locus-specific primer complementary to an extension product of the allele-specific primer.

4. A method for amplifying an allele-specific sequence, comprising:
   a) hybridizing an allele-specific primer to a first a nucleic acid molecule comprising a target allele;
   b) hybridizing an allele-specific blocker probe to a second nucleic acid molecule comprising an alternative allele, wherein the alternative allele corresponds to a same loci as the target allele, and wherein the allele-specific blocker probe comprises a minor groove binder;
   c) hybridizing a locus-specific detector probe to the first nucleic acid molecule;
   d) hybridizing a locus-specific primer to an extension product of the allele-specific primer; and
   e) PCR amplifying the target allele.

5. The method of claim 4, wherein the method has a specificity for amplifying the allele-specific sequence of at least two-fold.

6. The method of claim 4, wherein the allele-specific primer comprises a target-specific portion and an allele-specific nucleotide portion.

7. The method of claim 4, wherein the allele-specific primer comprises a tail.

8. The method of claim 7, wherein the tail is located at a 5' end of the allele-specific primer.

9. The method of claim 7, wherein the tail comprises repeated guanine (G) and cytosine (C) residues.

10. The method of claim 4, wherein a melting temperature ("Tm") of the allele-specific primer ranges from about 50° C. to 66° C.

11. The method of claim 4, wherein a concentration of the allele-specific primer is between about 20-900 nM.

12. The method of claim 6, wherein the allele-specific nucleotide portion is located at a 3' end of the allele-specific primer.

13. The method of claim 6, wherein the allele-specific nucleotide portion of the allele specific primer comprises a highly discriminating base.

14. The method of claim 4, wherein a 3' end of the allele-specific blocker probe is non-extendable.

15. The composition of claim 3, wherein the allele-specific primer comprises a target-specific portion and an allele-specific nucleotide portion.

16. The composition of claim 15, wherein the allele-specific nucleotide portion is located at a 3' end of the allele-specific primer.

17. The composition of claim 3, wherein the allele-specific primer comprises a tail, and the tail is located at a 5' end of the allele-specific primer.

18. The composition of claim 17, wherein the tail comprises repeated guanine (G) and cytosine (C) residues.

19. The composition of claim 3, wherein the allele-specific primer has a melting temperature ("Tm") of about 50° C. to 66° C.

20. The composition of claim 3, wherein the allele-specific primer has a concentration between about 20-900 nM.

21. The composition of claim 3, wherein a 3'-end of the allele-specific blocker probe is non-extendable.

* * * * *